US012161655B2

(12) United States Patent
Cynamon et al.

(10) Patent No.: US 12,161,655 B2
(45) Date of Patent: Dec. 10, 2024

(54) METHODS OF TREATING MYCOBACTERIAL INFECTIONS USING TETRACYCLINE COMPOUNDS

(71) Applicants: Paratek Pharmaceuticals, Inc., King Of Prussia, PA (US); United States Government as Represented by the Department of Veterans Affairs, Washington, DC (US)

(72) Inventors: Michael Henry Cynamon, Dewitt, NY (US); Michael P. Draper, Windham, NH (US); Judith N. Steenbergen, Newtown, PA (US); S. Ken Tanaka, Bellevue, WA (US)

(73) Assignees: Paratek Pharmaceuticals, Inc., Boston, MA (US); The United States Government as represented by the Department of Veterans Affairs, Washington, DC (US)

( * ) Notice: Subject to any disclaimer, the term of this patent is extended or adjusted under 35 U.S.C. 154(b) by 823 days.

(21) Appl. No.: 17/273,034

(22) PCT Filed: Sep. 3, 2019

(86) PCT No.: PCT/US2019/049368

§ 371 (c)(1),
(2) Date: Mar. 3, 2021

(87) PCT Pub. No.: WO2020/051151

PCT Pub. Date: Mar. 12, 2020

(65) Prior Publication Data

US 2021/0346408 A1 Nov. 11, 2021

Related U.S. Application Data

(60) Provisional application No. 62/760,131, filed on Nov. 13, 2018, provisional application No. 62/746,039,
(Continued)

(51) Int. Cl.
*A61K 31/65* (2006.01)
*A61P 31/06* (2006.01)

(52) U.S. Cl.
CPC .............. *A61K 31/65* (2013.01); *A61P 31/06* (2018.01)

(58) Field of Classification Search
CPC ................ A61K 31/65; A61K 31/5377; A61K 31/7048; A61K 45/06; A61K 2300/00;
(Continued)

(56) References Cited

U.S. PATENT DOCUMENTS 6,846,939 B2 1/2005 Nelson et al.
9,314,475 B2 4/2016 Johnston
2018/0016225 A1 1/2018 Levy et al.

FOREIGN PATENT DOCUMENTS

WO WO-2018051102 A1 * 3/2018 ........... A61K 31/155

OTHER PUBLICATIONS

Aziz et al., Teicoplanin—Tigecycline Combination Shows Synergy Against *Mycobacterium abscessus*. Front Microbiol. May 11, 2018;9:932, 8 pages.

(Continued)

*Primary Examiner* — Deborah D Carr
(74) *Attorney, Agent, or Firm* — McCarter & English, LLP; Jonathan M. Sparks; Yelena Margolin

(57) ABSTRACT

The present invention provides methods of treating mycobacterial infections or mycobacterial diseases by adminis-
(Continued)

tering a tetracycline compound, e.g., omadacycline, or a pharmaceutically acceptable salt thereof.

43 Claims, 4 Drawing Sheets

Related U.S. Application Data filed on Oct. 16, 2018, provisional application No. 62/731,410, filed on Sep. 14, 2018, provisional application No. 62/726,738, filed on Sep. 4, 2018.

(58) Field of Classification Search
CPC .......... A61P 31/06; A61P 31/04; A61P 31/08; A61P 11/00
See application file for complete search history.

(56) References Cited

OTHER PUBLICATIONS

Cynamon et al., In vitro activity of TP-271 against *Mycobacterium abscessus*, *Mycobacterium fortuitum*, and *Nocardia* species. Antimicrob Agents Chemother. Jul. 2012;56(7):3986-8.

Ferro et al., Tigecycline Is Highly Efficacious against *Mycobacterium abscessus* Pulmonary Disease. Antimicrob Agents Chemother. Apr. 22, 2016;60(5):2895-900.

Myojin et al., Chronic otitis media caused by *Mycobacterium abscessus* spp. massiliense treated with tigecycline in a 10-year-old child. Int J Infect Dis. Sep. 2018;74:10-12.

Pang et al., Drug Susceptibility of 33 Reference Strains of Slowly Growing *Mycobacteria* to 19 Antimicrobial Agents. Biomed Res Int. 2017;2017:1584658, 13 pages.

Pryjma et al., Acts in Synergy and Is Bactericidal with Frontline *Mycobacterium abscessus* Antibiotics Clarithromycin and Tigecycline, Suggesting a Potent Treatment Combination. Antimicrob Agents Chemother. Jul. 27, 2018;62(8):e00283-18, 10 pages.

Shoen et al., In Vitro Activities of Omadacycline against Rapidly Growing *Mycobacteria*. Antimicrob Agents Chemother. Apr. 25, 2019;63(5):e02522-18, 4 pages.

Wallace et al., Clinical experience in 52 patients with tigecycline-containing regimens for salvage treatment of *Mycobacterium abscessus* and *Mycobacterium chelonae* infections. J Antimicrob Chemother. Jul. 2014;69(7):1945-53.

International Search Report and Written Opinion for Application No. PCT/US2019/049368, dated Jan. 21, 2020, 13 pages.

Wallace et al., Comparison of the in vitro activity of the glycylcycline tigecycline (formerly GAR-936) with those of tetracycline, minocycline, and doxycycline against isolates of nontuberculous mycobacteria. Antimicrob Agents Chemother. Oct. 2002;46(10):3164-7.

Draper et al., Mechanism of action of the novel aminomethylcycline antibiotic omadacycline. Antimicrob Agents Chemother. 2014;58(3): 1279-83.

Falkinham, Challenges of NTM Drug Development. Front Microbiol. Jul. 18, 2018;9:1613, 7 pages.

Heidrich et al., The Novel Aminomethylcycline Omadacycline Has High Specificity for the Primary Tetracycline-Binding Site on the Bacterial Ribosome. Antibiotics (Basel). Sep. 22, 2016;5(4):32, 15 pages.

Helguera-Repetto et al., Differential macrophage response to slow- and fast-growing pathogenic mycobacteria. Biomed Res Int. 2014;2014:916521, 10 pages.

Montes-Worboys et al., Targeted delivery of amikacin into granuloma. Am J Respir Crit Care Med. Dec. 15, 2010;182(12): 1546-53.

Tzanis et al., Effect of Food on the Bioavailability of Omadacycline in Healthy Participants. J Clin Pharmacol. Mar. 2017;57(3):321-327.

MIlano et al., Omadacycline: development of a novel aminomethylcycline antibiotic for treating drug-resistant bacterial infections. Future Microbiol. Oct. 2016; 11:1421-1434.

Zhang et al., Amikacin Liposome Inhalation Suspension (ALIS) Penetrates Non-tuberculous Mycobacterial Biofilms and Enhances Amikacin Uptake Into Macrophages. Front Microbiol. May 16, 2018;9:915, 12 pages.

* cited by examiner

METHODS OF TREATING MYCOBACTERIAL INFECTIONS USING TETRACYCLINE COMPOUNDS

RELATED APPLICATIONS

This application is a 35 U.S.C. § 371 national stage filing of International Application No. PCT/US2019/049368, filed on Sep. 3, 2019, which claims priority to U.S. Provisional Patent Application No. 62/726,738, filed on Sep. 4, 2018; U.S. Provisional Patent Application No. 62/731,410, filed on Sep. 14, 2018; U.S. Provisional Patent Application No. 62/746,039, filed on Oct. 16, 2018; and U.S. Provisional Patent Application No. 62,760,131, filed on Nov. 13, 2018. The entire contents of each of the foregoing applications are hereby incorporated herein by reference.

GOVERNMENT SUPPORT

This invention was created in the performance of a Cooperative Research and Development Agreement with the Department of Veterans Affairs, an agency of the U.S. Government, which has certain rights in the invention.

INTRODUCTION

The genus *Mycobacterium* is currently known to include more than 180 bacterial species, many of which are known human pathogens. For example, this genus includes *M. tuberculosis*, the causative agent of tuberculosis, and *M. leprae*, the causative agent of leprosy. Other members of the genus *Mycobacterium*, which may be referred to, interchangeably or synonymously, as atypical mycobacteria, non-tuberculous mycobacteria (NTM) or mycobacteria other than tubercle bacilli (MOTT), can be opportunistic and at times deadly pathogens. For example, these organisms can produce localized disease in the lungs, lymph glands, skin, wounds or bone, and, occasionally, disseminated disease.

Mycobacterial infections are treated with antibiotics, or combinations of antibiotics, and the treatment times are usually long, e.g., lasting weeks, months or even years. For example, *Mycobacterium tuberculosis* infections are usually treated with isoniazid, rifampicin, ethambutol and pyrazinamide, and *Mycobacterium leprae* infections are usually treated with rifampicin, dapsone and clofazimine. Macrolide antibiotics, such as clarithromycin and azithromycin, are usually used, in combination with other antibiotics, for treating infections with NTM. For example, as described in Ryu et al., *Tuberc. Respir. Dis.* 2016, 79:74-84, the standard treatment of lung disease caused by an infection with NTM mycobacteria belonging to *Mycobacterium Avium* Complex (MAC) comprises administration of rifampicin, ethambutol and a macrolide antibiotic, such as azithromycin. Amikacin or streptomycin may also be added to the antibiotic regimen in case of a severe disease. In another example, lung disease that is caused by an infection with a mycobacterial species *Mycobacterium kansasii* includes administration of a macrolide antibiotic rifampicin and ethambutol. In yet another example, lung infections in cystic fibrosis patients due to *M. abscessus* complex typically require an oral macrolide, intravenous amikacin and one or more additional antibiotics such as cefoxitin, impenem or tigecycline (Floto et al., *Thorax* 2016 January; 71 Suppl 1:i1-22).

Antibiotics within the tetracycline family have also been tested for activity against mycobacteria. For example, Wallace et al., *Antimicrob. Agents Chemother.* 2002, 46(10):

3164-3167 describe comparing in vitro activity of tigecycline, tetracycline, minocycline and doxycycline against slow-growing NTM, such as *M. marinum, M. kansasii, M. xenopi* and *M. simiae*, and fast-growing NTM, such as *M. fortuitum, M. abscessus* and *M. chelonae*. Wallace et al. demonstrate that different tetracycline compounds display widely different activities against various strains of NTM. For example, minocycline, doxycycline and tetracycline demonstate a very low activity against strains of *M. abscessus*, while tigecycline demonstrates good activity against this species. In another example, minocycline was found to have higher activity than tigecycline against *M. marinum* and *M. kansasii.*

Tigecycline has been recognized as a promising antibiotic for treating mycobacterial infections. However, the use of tigecycline in clinic has been limited by the adverse effects associated with tigecycline, particularly the adverse gastrointestinal effects, such as nausea and vomiting. For example, Myojin et al., *International J. Infect. Diseases* 2018, 74:10-12 describe using tigecycline, in combination with clarithromycin and amikacin for treating mycobacterial otitis in a 10-year old boy. The patient required the use of an additional medication, ondansetron, in order to control nausea and vomiting that he experienced after the tigecycline infusion. In another example, Wallace et al., *J. Antimicrob. Chemother.* 2014, 69:1945-1953 describe clinical experience in 52 patients who received tigecycline-containing regimens to treat *M. abscessus* and *M. chelonae* infections. Wallace et al. report that "[t]here was considerable inter-individual variability in tigecycline dosing and it was clear that target doses were not achieved in most patients. Approximately half of the patients had dose reductions due to nausea, vomiting or anorexia." Wallace et al. also report that adjustments to dosages of tigecycline were made based on the level of tolerability, and that the use of antiemetics, such as ondansetron, was required to improve patient tolerability. Because many mycobacterial infections require administration of one or more antibiotics over a long term, e.g., months or even years, the utility of tigecycline for treating mycobacterial infections may be limited. Thus, safe and effective antibiotics for treating mycobacterial infections are needed.

SUMMARY OF THE INVENTION

The present invention is based on a surprising discovery that certain tetracycline compounds, e.g., omadacycline or a pharmaceutically acceptable salt thereof, may be particularly effective for treating or preventing mycobacterial infections. Omadacycline, which may also be referred to herein as OMC, PTK 0796 or Compound 1, which is sold under the brand name NUZYRA®, is a 9-aminomethyl tetracycline derivative that is currently in advanced clinical development for the treatment of various bacterial infections. Omadacycline is (4aS,5aR,12aS)-4,7-bis(dimethylamino)-3,10,12,12a-tetrahydroxy-9-((neopentylamino)methyl)-1,11-dioxo-1,4,4a,5,5a,6,11,12a-octahydrotetracene-2-carboxamide, or 9-[(2,2-dimethyl-propyl amino)-methyl]-minocycline, which is represented by formula (4):

(4)

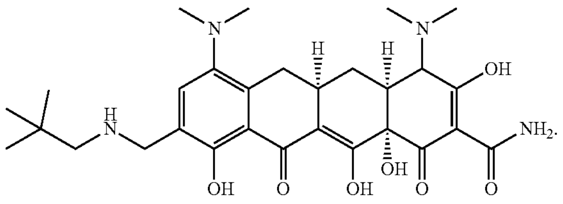

In some examples, omadacycline may also be represented by formula (5):

(5)

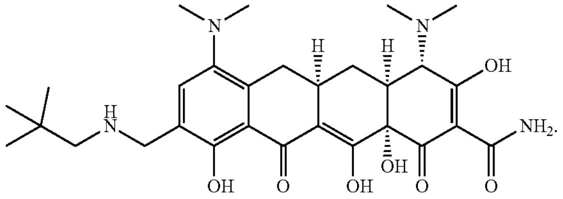

The present inventors have surprisingly discovered that omadacycline has promising activity against certain mycobacterial species, e.g., NTM, such as *Mycobacterium abscessus, Mycobacterium chelonae* and *Mycobacterium fortuitum*. It has also been surprisingly discovered that omadacycline, either alone or in combination with clarithromycin or linezolid, has promising activity against Bacille Calmette Guerin (BCG), an attenuated version of *Mycobacterium bovis*, which is a species that is closely related to *Mycobacterium tuberculosis.*

In addition, it has been demonstrated that administration of omadacycline to healthy volunteers resulted in higher omadacycline concentrations in the lungs, and, specifically, in epithelial lining fluid (ELF) and in alveolar cells (ACs), such as alveolar macrophages (AMs), than simultaneous omadacycline plasma concentrations. Infections with mycobacteria, e.g., NTM or *Mycobacterium tuberculosis*, often cause pulmonary disease in which mycobacteria may persist extracellularly in biofilms or intracellularly within macrophages and other cells in the infected host. Mycobacterial infections may also cause granulomatous inflammation and abscess formation, trapping the mycobacteria in granulomas. Thus, a tetracycline compound, e.g., omadacycline or a pharmaceutically acceptable salt thereof, that is capable of penetrating infected tissues, e.g., lungs, and infected cells, e.g., macrophages is particularly advantageous for treating mycobacterial infections. Also, migrating omadacycline-loaded macrophages may facilitate site-specific delivery of omadacycline into granulomas, thereby promoting clearance of the infecting mycobacteria.

Furthermore, omadacycline may be administered to a subject orally, e.g., once daily or twice daily, and administration of omadacycline is known to be associated with relatively few side effects, e.g., gastrointestinal side effects, such as nausea and/or vomiting. Thus, omadacycline is uniquely suited for the treatment of mycobacterial infections which often requires administration of an antibiotic agent for prolonged periods of time, e.g., weeks, months or even years. In contrast, tigecycline, which may only be administered intravenously, is often associated with significant side effects, such as nausea and vomiting. Thus, the utility of tigecycline for treating mycobacterial infections is very limited.

Accordingly, in some embodiments, the present invention provides a method of treating or preventing a mycobacterial infection in a subject in need thereof that comprises administering to the subject an effective amount of a tetracycline compound, or a pharmaceutically acceptable salt. ester or a prodrug thereof, wherein the tetracycline compound is represented by formula (1):

(1)

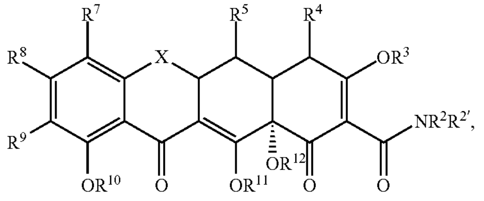

wherein:

X is $CHC(R^{13}Y'Y)$, $CR^{6'}R^{6}$, S, $NR^{6}$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino. arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ and $R^8$ are each independently hydrogen, hydroxyl, halogen. thiol, alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio. alkylsulfinyl, alkylsulfonyl, alkylamino, or an arylalkyl;

Y' and Y are each independently hydrogen, halogen, hydroxyl, cyano, sulfhydryl, amino. alkyl, alkenyl, alkynyl, alkoxy, alkylthio, alkylsulfinyl, alkylsulfonyl, alkylamino, or an arylalkyl; such that the mycobacterial infection in the subject is treated or prevented.

In some embodiments, $R^9$ is $—CH_2NR'R''$, wherein R' and R'' are each independently selected from the group consisting of hydrogen, alkyl, alkenyl, alkynyl, carbonyl, acyl, aryl, heteroaryl, cycloalkyl and cycloalkenyl groups; or wherein R' and R'' are joined together to form a ring.

In some embodiments, the tetracycline compound is represented by formula (2):

(2)

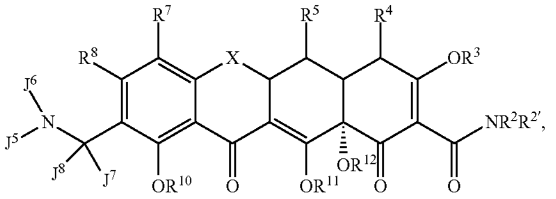

wherein:

$J^5$ and $J^6$ are each independently hydrogen, alkyl, alkenyl, alkynyl, aryl, sulfonyl, acyl, alkoxycarbonyl, alkaminocarbonyl, alkaminothiocarbonyl, substituted thiocarbonyl, substituted carbonyl, alkoxythiocarbonyl, or linked to form a ring; and $J^7$ and $J^8$ are each alkyl, halogen, or hydrogen.

In some embodiments, X is $CR^{6'}R^6$, and wherein $R^6$ and $R^{6'}$ are both hydrogen.

In some embodiments, $R^4$ is $NR^{4'}R^{4''}$, and $R^{4'}$ and $R^{4''}$ are each independently alkyl.

In some embodiments, $R^7$ is dialkylamino.

In some embodiments, the tetracycline compound is represented by formula (3):

(3)

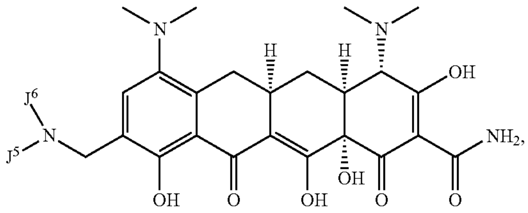

wherein $J^5$ is alkyl; and $J^6$ is hydrogen.

In some embodiments. tetracycline compound is omadacycline represented by formula (4):

(4)

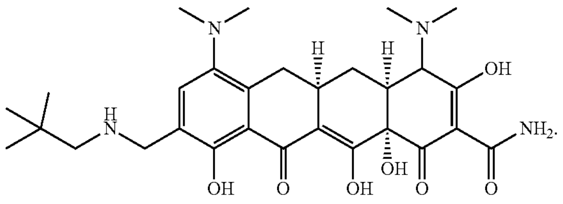

In a further embodiment, omadacycline is represented by formula (5):

(5)

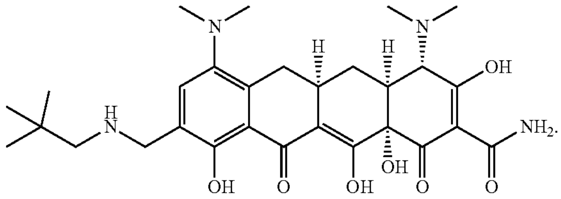

In some embodiments, the present invention provides a method of treating or preventing a mycobacterial infection in a subject in need thereof that comprises administering to the subject an effective amount of omadacycline, or a pharmaceutically acceptable salt, ester or a prodrug thereof, wherein omadacycline is represented by formula (4):

(4)

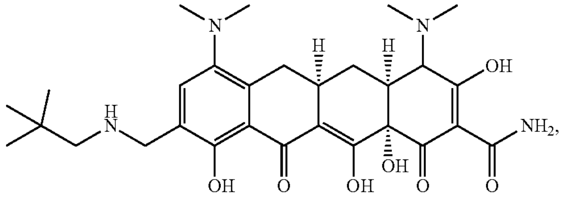

such that the mycobacterial infection in the subject is treated or prevented.

In a further embodiment, omadacycline is represented by formula (5):

(5)

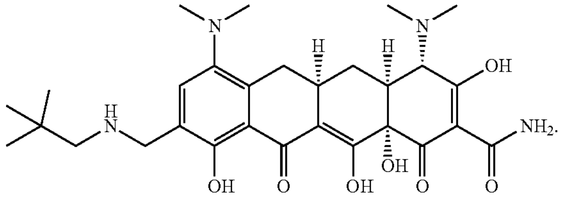

In some aspects, the mycobacterial infection is caused by a slow-growing *Mycobacterium.*

In some aspects, the slow-growing *Mycobacterium* belongs to *Terrae* clade. In further aspects, the slow-growing *Mycobacterium* belongs to a mycobacterial species selected from the group consisting of the following species: *M. terrae, M. algericus, M. arupensis, M. engbaekii, M. heraklionensis, M. hiberniae, M. icosiumassiliensis, M. kumamotonensis, M. longobardus, M. minnesotensis, M. nonchromogenicus, M. paraterrae, M. senuense, M. sinensis* and *M. virginiensis.*

In some embodiments. the slow-growing *Mycobacterium* belongs to *Triviale* clade. In further embodiments, the slow-growing *Mycobacterium* belongs to a mycobacterial species selected from the group consisting of the following species: *M. trivialis, M. koreensis* and *M. parakoreensis.*

In some embodiments, the slow-growing *Mycobacterium* belongs to the Tuberculosis-*Simiae* clade. In further embodiments, the slow-growing *Mycobacterium* belongs to a mycobacterial species selected from the group consisting of the following species: *M. tuberculosis, M. tuberculosis* subsp.

*tuberculosis, M. africanum, M. alsense, M. angelicum, M. arosiense, M. asiaticum, M. avium, M. avium* subsp. *avium, M. avium* subsp. *paratuberculosis, M. avium* subsp. *silvaticum, M. avium* subsp. *hominissuis, M. bohemicum, M. botniense, M. bouchedurhonense, M. bourgelatii, M. bovis, M. bovis* subsp. *bovis, M. bovis* subsp. *caprae, M. branderi, M. canettii, M. caprae, M. celatum, M. chimaera, M. colombiense, M. conspicuum, M. cookii, M. europaeum, M. florentinum, M. fragae, M. gastri, M. genavsnse, M. gordonae, M. haemophilum, M. heckshornense, M. heidelbergense, M. indicus pranii, M. interjectum, M. intermedium, M. intracellulare, M. kansasii, M. kubicae, M. kyorinense, M. lacus, M. lentiflavum, M. leprae, M. lepraemurium, M. lepromatosis, M. liflandii, M. malmoense, M. mantenii, M. marinum, M. marseillense, M. microti, M. monteriorense, M. mungi, M. nebraskense, M. novomagense, M. orygis, M. palustre, M. paraense, M. parraffinicum, M. paragordonae, M. paraintracellulare, M. parascrofulaceum, M. paraseculense, M. parmense, M. perscum, M. pinnipedii, M. pseudoshotsii, M. riyadhense, M. saskatchewanense, M. scrofulaceum, M. seculense, M. sherrisii, M. shimoidei, M. shinjukuense, M. shottsii, M. simiae, M. stomatepiae, M. szulgai, M. timonense, M. triplex, M. ulcerans, M. xenopi* and *M. yongonense.*

In some embodiments, the slow-growing *Mycobacterium* belongs to a *Mycobacterium tuberculosis* complex (MTBC). In further embodiments, the slow-growing *Mycobacterium* belongs to a mycobacterial species selected from the group consisting of the following species: *M. africanum, M. bovis, M. bovis BCG, M. canetti, M. caprae, M. microti, M. mungi, M. orygis, M. pinnipedii, M. suricattae* and *M. tuberculosis*. In one further aspect, the slow-growing *Mycobacterium* belongs to a mycobacterial species *M. tuberculosis.*

In some embodiments, the slow-growing *Mycobacterium* is a nontuberculous *Mycobacterium* (NTM). In some aspects, the NTM belongs to a *Mycobacterium avium* complex (MAC). In further aspects, the NTM belongs to a mycobacterial species selected from the group consisting of the following species: *M. avium, M. avium paratuberculosis, M. avium silvaticum, M. avium "hominissuis", M. colombiense, M. chimaera, M. indicus pranii* and *M. intracellulare.*

In some embodiments, the mycobacterial infection is caused by a rapid-growing *Mycobacterium*. In some aspects, the rapid-growing *Mycobacterium* is NTM. In further aspects, the rapid-growing *Mycobacterium* belongs to an *Abscessus*-*Chelonae* clade. In some examples, the rapid-growing *Mycobacterium* belongs to a mycobacterial species selected from the group consisting of the following species: *M. abscessus, M. abscessus* subsp. *abscessus, M. abscessus* subsp. *bolletii, M. abscessus* subsp. *massiliense, M. chelonae, M. chelonae* subsp. *chelonae, M. immunogenum, M. salmoniphilum, M. franklinii* and *M. saopaulense.*

In one aspect, the rapid-growing *Mycobacterium* belongs to a mycobacterial species *M. abscessus*. In one aspect, the rapid-growing *Mycobacterium* belongs to a mycobacterial species *M. chelonae.*

In some embodiments, the rapid-growing *Mycobacterium* belongs to a Fortuitum-Vaccae clade. In further embodiments, the rapid-growing *Mycobacterium* belongs to a mycobacterial species selected from the group consisting of the following species: *M. fortuitum, M. fortuitum* subsp. *fortuitum, M. fortuitum* subsp. *acetamidolyticum, M. acapulcense, M. agri, M. aichiense, M. alvei, M. anyangense, M. arabiense, M. arcueilence, M. aromaticivorans, M. aubagnense, M. aurum, M. austroafrinacum, M. bacteremicum, M. boenickei, M. brisnanense, M. brumae, M. canariasense,*

*M. celeriflavum, M. chitae, M. chlorophenolicum, M. chubuense, M. conceprionense, M. confluentis, M. cosmeticum, M. crocinum, M. diernhoferi, M. doricum, M. duvalii, M. elephantis, M. fallax, M. facinogenes, M. flavescens, M. fluoranthenivorans, M. frederikspergense, M. gadium, M. gilvum, M. goodii, M. hassiacum, M. helvum, M. hippocampi, M. hodieri, M. holsaticum, M. houstonense, M. insubricum, M. iranicum, M. komanii, M. komossense, M. litorale, M. llatzerense, M. lutetiense, M. madagascariense, M. mageritense, M. malmesburyense, M. monacense, M. montmartrense, M. moriokaense, M. mucogenicum, M. murale, M. neoaurum, M. neworleansense, M. novocastrense, M. obuense, M. oryzae, M. pallens, M. parafortuitum, M. peregrinum, M. phlei, M. phocaicum, M. porcinum, M. ponferae, M. psychrotolerans, M. pulvens, M. pyrenivorans, M. rhodesiae, M. rufum, M. rutilum, M. sarraceniae, M. sediminis, M. senegalense, M. septicum, M. setense, M. smegmatis, M. sphagni, M. thermoresistibile, M. tokaiense, M. tusciae, M. vaccae, M. vanbaalenii, M. vulneris* and *M. wolinskyi*. In a further embodiment, the rapid-growing *Mycobacterium* belongs to a mycobacterial species *M. fortuitum.*

In some embodiments, the mycobacterial infection is in the lungs of the subject.

In some embodiments, the subject additionally has a disease of the lungs. In further embodiments, the disease of the lungs is selected from the group consisting of chronic obstructive pulmonary disease (COPD), an occupational lung disease, tuberculosis, bronchiectasis, cystic fibrosis and alpha 1-antitrypsin deficiency. In some aspects, the subject has undergone lung transplantation.

In some embodiments, the mycobacterial infection is in a lymph node of the subject. In some embodiments, the mycobacterial infection is an osteoarticular infection. In some embodiments, the mycobacterial infection is in a joint or a bone of the subject. In some embodiments, the mycobacterial infection is a skin or a soft tissue infection (SSTI). In some embodiments, the mycobacterial infection causes a disease selected from the group consisting of swimming pool granuloma and Buruli ulcer.

In some aspects, the mycobacterial infection involves a foreign object disposed in the subject. In further aspects, the foreign object is selected from the group consisting of a medical device, an implant and a tattoo ink. In some embodiments, the medical device is a cardiac pacemaker. In some embodiments, the implant is selected from the group consisting of a cardiovascular implant, an orthopedic implant and a cosmetic implant. In some embodiments, the cardiovascular implant is a heart valve. In some embodiments, the orthopedic implant is selected from the group consisting of a pin, a rod, a screw and a plate. In some embodiments, the cosmetic implant is selected from the group consisting of a breast implant, a nose prosthesis and an injectable filler.

In some aspects, the present invention also provides a method of treating or preventing a mycobacterial disease in a subject in need thereof that comprises administering to the subject an effective amount of a tetracycline compound, or a pharmaceutically acceptable salt, ester or a prodrug thereof, wherein the tetracycline compound is represented by formula (1):

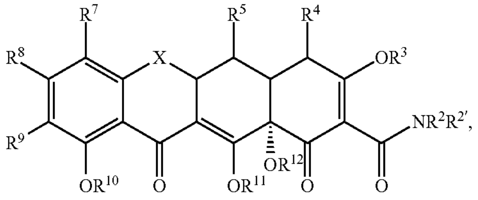

(1)

wherein:

- X is $CHC(R^{13}Y'Y)$, $CR^{6'}R^6$, S, $NR^6$, or O;
- $R^4$ is $NR^{4'}R^{4''}$, alkyl, alkenyl, alkynyl, aryl, hydroxyl, halogen, or hydrogen:
- $R^2$, $R^{4'}$, $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
- $R^{2'}$, $R^3$, $R^{10}$, $R^{11}$ and $R^{12}$ are each hydrogen or a pro-drug moiety;
- $R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
- $R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
- $R^7$ and $R^8$ are each independently hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
- $R^9$ is aminoalkyl;
- $R^{13}$ is hydrogen, hydroxy, alkyl, alkenyl, alkynyl, alkoxy, alkylthio, alkylsulfinyl, alkylsulfonyl, alkylamino, or an arylalkyl:
- Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that the mycobacterial disease in the subject is treated or prevented.

In some aspects, the present invention also provides a method of controlling or reducing the advancement, severity or effects of a mycobacterial disease in a subject in need thereof that comprises administering to the subject an effective amount of a tetracycline compound, or a pharmaceutically acceptable salt, ester or a prodrug thereof, wherein the tetracycline compound is represented by formula (1):

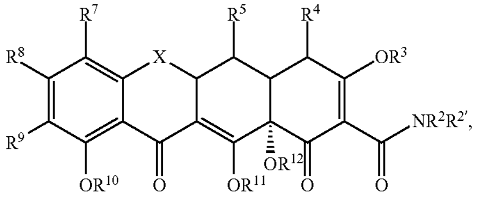

(1)

wherein:

- X is $CHC(R^{13}Y'Y)$, $CR^{6'}R^6$, S, $NR^6$, or O;
- $R^4$ is $NR^{4'}R^{4''}$, alkyl, alkenyl, alkynyl, aryl, hydroxyl, halogen, or hydrogen;
- $R^2$, $R^{4'}$, $R^{4''}$ are each independently hydrogen, alkyl, alkenyl, alkynyl, alkoxy. alkylthio, alkylsulfinyl, alkylsulfonyl, alkylamino, arylalkyl, aryl, heterocyclic, heteroaromatic or a prodrug moiety;
- $R^{2'}$, $R^3$, $R^{10}$, $R^{11}$ and $R^{12}$ are each hydrogen or a pro-drug moiety;
- $R^5$ is hydroxyl, hydrogen, thiol, alkanoyl, aroyl, alkaroyl, aryl, heteroaromatic, alkyl. alkenyl, alkynyl, alkoxy, alkylthio, alkylsulfinyl, alkylsulfonyl, alkylamino. arylalkyl, alkyl carbonyloxy, or aryl carbonyloxy;
- $R^6$ and $R^{6'}$ are each independently hydrogen, methylene, absent, hydroxyl, halogen. thiol, alkyl, alkenyl, alkynyl, aryl, alkoxy, alkylthio, alkylsulfinyl, alkylsulfonyl, alkylamino, or an arylalkyl;
- $R^7$ and $R^8$ are each independently hydrogen, hydroxyl, halogen. thiol, alkyl, alkenyl, alkynyl, aryl, alkoxy, alkylthio, alkylsulfinyl, alkylsulfonyl, alkylamino, or an arylalkyl;
- $R^9$ is aminoalkyl;
- $R^{13}$ is hydrogen, hydroxy, alkyl, alkenyl, alkynyl, alkoxy, alkylthio. alkylsulfinyl. alkylsulfonyl, alkylamino, or an arylalkyl;
- Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that the mycobacterial disease in the subject is controlled, or the advancement, severity or effects of the mycobacterial disease in the subject are reduced.

In some embodiments, $R^9$ is $—CH_2NR'R''$, wherein R' and R'' are each independently selected from the group consisting of hydrogen, alkyl, alkenyl, alkynyl, carbonyl, acyl, aryl, heteroaryl, cycloalkyl and cycloalkenyl groups; or wherein R' and R'' are joined together to form a ring.

In some aspects, the tetracycline compound is represented by formula (2):

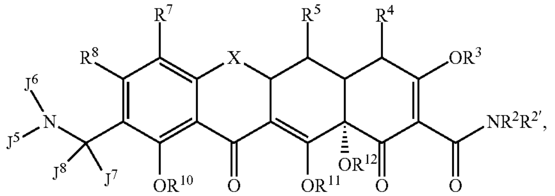

(2)

wherein:

$J^5$ and $J^6$ are each independently hydrogen. alkyl, alkenyl, alkynyl, aryl, sulfonyl, acyl. alkoxycarbonyl, alkaminocarbonyl, alkaminothiocarbonyl, substituted thiocarbonyl. substituted carbonyl, alkoxythiocarbonyl, or linked to form a ring; and $J^7$ and $J^8$ are each alkyl, halogen, or hydrogen.

In some aspects, X is $CR^{6'}R^6$ and wherein $R^6$ and $R^{6'}$ are both hydrogen.

In some aspects, $R^4$ is $NR^{4'}R^{4''}$, and $R^{4'}$ and $R^{4''}$ are each independently alkyl.

In some embodiments, $R^7$ is dialkylamino.

In some embodiments, the tetracycline compound is represented by formula (3):

(3)

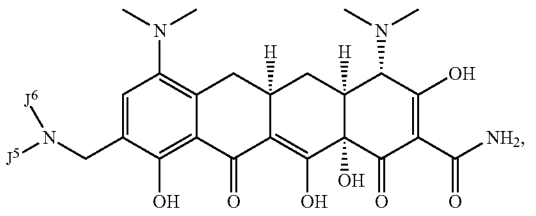

wherein $J^5$ is alkyl; and $J^6$ is hydrogen.

In some aspects, the tetracycline compound is omadacycline represented by formula (4):

(4)

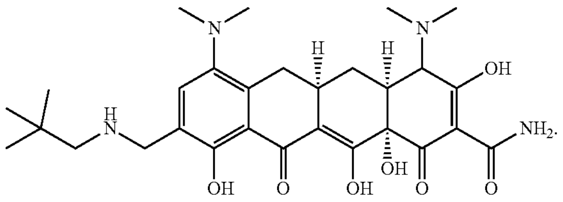

In one further aspect, omadacycline is represented by formula (5):

(5)

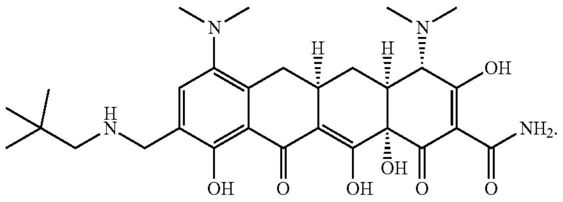

In some embodiments, the present invention also provides a method of treating or preventing a mycobacterial disease in a subject in need thereof that comprises administering to the subject an effective amount of omadacycline, or a pharmaceutically acceptable salt, ester or a prodrug thereof, wherein omadacycline is represented by formula (4):

(4)

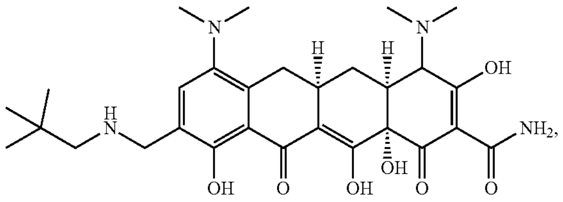

such that the mycobacterial disease in the subject is treated or prevented.

In some aspects, the present invention also provides a method of controlling or reducing the advancement, severity or effects of a mycobacterial disease in a subject in need thereof that comprises administering to the subject an effective amount of omadacycline, or a pharmaceutically acceptable salt, ester or a prodrug thereof, wherein omadacycline is (4)

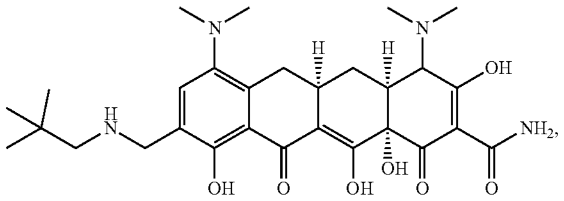

such that the mycobacterial disease in the subject is controlled, or the advancement, severity or effects of the mycobacterial disease in the subject are reduced.

In some aspects, omadacycline is represented by formula (5):

(5)

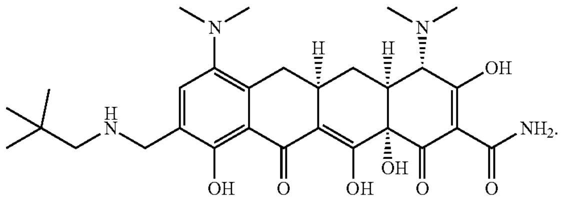

In some embodiments, the mycobacterial disease is caused by an infection with a slow-growing *Mycobacterium*. In further embodiments, the slow-growing *Mycobacterium* belongs to a *Mycobacterium tuberculosis* complex (MTBC). In some aspects, the slow-growing *Mycobacterium* belongs to a mycobacterial species *M. tuberculosis*. In one aspect, the mycobacterial disease is tuberculosis.

In some embodiments, the mycobacterial disease is caused by an infection with a rapid-growing *Mycobacterium*.

In some aspects, the mycobacterial disease is caused by an infection with NTM. In some aspects, the NTM belongs to a mycobacterial species selected from the group consisting of the following species: *M. avium, M. kansasii, M. scrofulaceum, M. xenopi, M. simiae, M. habana, M. szulgai, M. fortuitum, M. vaccae, M. malmoense, M. heckeshornense, M. chelonae and M. abscessus*. In some aspects, the NTM belongs to a mycobacterial species selected from the group consisting of the following species: *M. abscessus, M. chelonae* and *M. fortuitum*.

In some embodiments, the mycobacterial disease is selected from the group consisting of tuberculosis, leprosy, a pulmonary disease, lymphadenitis, a skin disease, an eye disease, a soft tissue disease, a bone disease, a fish tank granuloma and a Buruli ulcer. In further embodiments, the pulmonary disease is selected from the group consisting of bronchiectasis and pulmonary infection.

In some aspects, the mycobacterial disease is associated with a mycobacterial infection in a lymph node, a joint, a bone, a skin, a soft tissue of the subject.

In some embodiments, the mycobacterial disease is associated with a mycobacterial infection involving a foreign object disposed in the subject. In further embodiments, the foreign object is selected from the group consisting of a medical device, an implant and a tattoo ink.

In further aspects, the medical device is a cardiac pacemaker. In further aspects, the implant is selected from the group consisting of a cardiovascular implant, an orthopedic implant and a cosmetic implant. In further aspects, the cardiovascular implant is a heart valve. In further aspects, the orthopedic implant is selected from the group consisting of a pin, a rod, a screw and a plate. In further aspects, the cosmetic implant is selected from the group consisting of a breast implant, a nose prosthesis and an injectable filler.

In some embodiments, the present invention also provides a method of treating or preventing tuberculosis in a subject in need thereof that comprises administering to the subject an effective amount of a tetracycline compound, or a pharmaceutically acceptable salt, estr or a prodrug thereof, wherein the tetracycline compound is represented by formula (1):

(1)

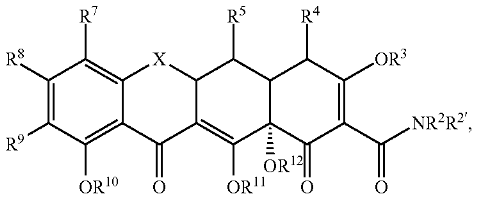

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy. alkylthio, alkylsulfinyl, alkylsulfonyl, alkylamino, arylalkyl, aryl, heterocyclic, heteroaromatic or a prodrug moiety;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio. alkylsulfinyl, alkylsulfonyl, alkylamino, or an arylalkyl;

$R^7$ and $R^8$ are each independently hydrogen, hydroxyl, halogen, thiol. alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano. sulfhydryl. amino, alkyl, alkenyl, alkynyl, alkoxy, alkylthio, alkylsulfinyl, alkylsulfonyl, alkylamino, or an arylalkyl; such that tuberculosis in the subject is treated or prevented.

In some embodiments, the present invention also provides a method of controlling or reducing the advancement, severity or effects of tuberculosis in a subject in need thereof that comprises administering to the subject an effective amount of a tetracycline compound, or a pharmaceutically acceptable salt, ester or a prodrug thereof, wherein the tetracycline compound is represented by formula (1):

(1)

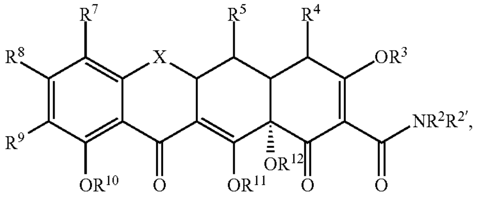

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety:

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio. alkylsulfinyl, alkylsulfonyl, alkylamino, or an arylalkyl;

$R^7$ and $R^8$ are each independently hydrogen, hydroxyl, halogen, thiol. alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano. sulfhydryl. amino, alkyl, alkenyl, alkynyl, alkoxy, alkylthio, alkylsulfinyl, alkylsulfonyl, alkylamino, or an arylalkyl; such that tuberculosis in the subject is controlled, or the advancement, severity or effects of tuberculosis in the subject are reduced.

In some embodiments, the present invention also provides a method of treating or preventing leprosy in a subject in need thereof that comprises administering to the subject an effective amount of a tetracycline compound, or a pharmaceutically acceptable salt, ester or a prodrug thereof, wherein the tetracycline compound is represented by formula (1):

(1)

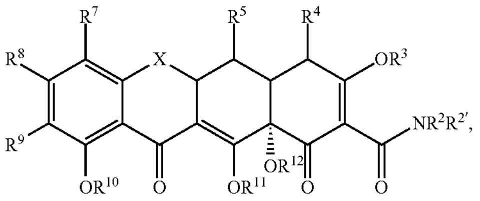

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ and $R^8$ are each independently hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy. alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that leprosy in the subject is treated or prevented.

In some embodiments, the present invention also provides a method of controlling or reducing the advancement, severity or effects of leprosy in a subject in need thereof that comprises administering to the subject an effective amount of a tetracycline compound, or a pharmaceutically acceptable salt, ester or a prodrug thereof, wherein the tetracycline compound is represented by formula (1):

(1)

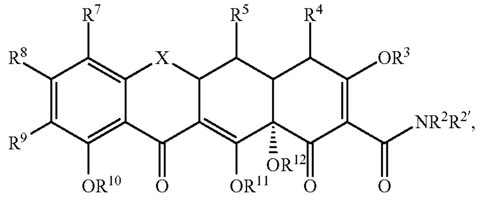

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy. alkylthio, alkylsulfinyl, alkylsulfonyl, alkylamino, arylalkyl, aryl, heterocyclic. heteroaromatic or a prodrug moiety;

$R^{2'}$, $R^3$, $R^{10}$, $R^{11}$ and $R^{12}$ are each hydrogen or a pro-drug moiety;

$R^5$ is hydroxyl, hydrogen, thiol. alkanoyl, aroyl, alkaroyl, aryl, heteroaromatic, alkyl. alkenyl, alkynyl, alkoxy, alkylthio. alkylsulfinyl, alkylsulfonyl, alkylamino. arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ and $R^8$ are each independently hydrogen, hydroxyl, halogen. thiol, alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio. alkylsulfinyl. alkylsulfonyl, alkylamino, or an arylalkyl;

Y' and Y are each independently hydrogen, halogen, hydroxyl, cyano, sulfhydryl, amino. alkyl, alkenyl, alkynyl, alkoxy. alkylthio, alkylsulfinyl, alkylsulfonyl, alkylamino, or an arylalkyl; such that leprosy in the subject is controlled, or the advancement, severity or effects of leprosy in the subject are reduced.

In some embodiments, the present invention also provides a method of treating or preventing bronchiectasis in a subject in need thereof that comprises administering to the subject an effective amount of a tetracycline compound, or a pharmaceutically acceptable salt, ester or a prodrug thereof, wherein the tetracycline compound is represented by formula (1):

(1)

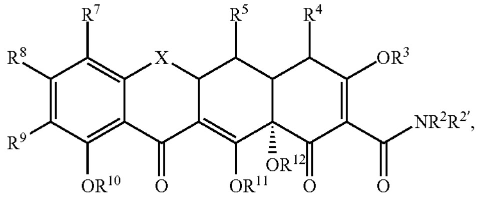

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic. heteroaromatic or a prodrug moiety:

$R^{2'}$, $R^3$, $R^{10}$, $R^{11}$ and $R^{12}$ are each hydrogen or a pro-drug moiety;

$R^5$ is hydroxyl, hydrogen, thiol. alkanoyl, aroyl, alkaroyl, aryl, heteroaromatic, alkyl, alkenyl, alkynyl, alkoxy. alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen. thiol, alkyl, alkenyl, alkynyl, aryl, alkoxy, alkylthio, alkylsulfinyl, alkylsulfonyl, alkylamino. or an arylalkyl;

$R^7$ and $R^8$ are each independently hydrogen, hydroxyl, halogen, thiol. alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that bronchiectasis in the subject is treated or prevented.

In some embodiments, the present invention also provides a method of controlling or reducing the advancement, severity or effects of bronchiectasis in a subject in need thereof that comprises administering to the subject an effective amount of a tetracycline compound, or a pharmaceutically acceptable salt, ester or a prodrug thereof, wherein the tetracycline compound is represented by formula (1):

(1)

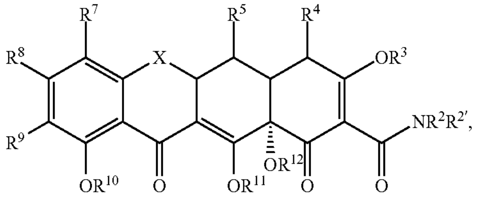

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino. arylalkyl, aryl, heterocyclic, heteroaromatic or a prodrug moiety;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino. or an arylalkyl;

$R^7$ and $R^8$ are each independently hydrogen, hydroxyl, halogen. thiol, alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that bronchiectasis in the subject is controlled, or the advancement, severity or effects of bronchiectasis in the subject are reduced.

In some embodiments, the present invention also provides a method of treating or preventing cavitary lung disease in a subject in need thereof that comprises administering to the subject an effective amount of a tetracycline compound, or a pharmaceutically acceptable salt, ester or a prodrug thereof, wherein the tetracycline compound is represented by formula (1):

(1)

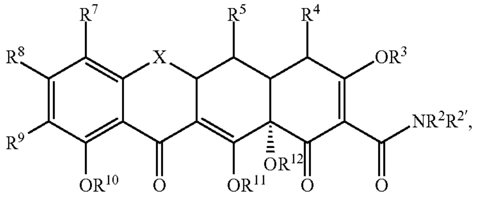

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety:

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy. alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio. alkylsulfinyl, alkylsulfonyl, alkylamino, or an arylalkyl;

$R^7$ and $R^8$ are each independently hydrogen, hydroxyl, halogen, thiol. alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano. sulfhydryl. amino, alkyl, alkenyl, alkynyl, alkoxy, alkylthio, alkylsulfinyl, alkylsulfonyl, alkylamino, or an arylalkyl; such that cavitary lung disease in the subject is treated or prevented.

In some embodiments, the present invention also provides a method of controlling or reducing the advancement, severity or effects of cavitary lung disease in a subject in need thereof that comprises administering to the subject an effective amount of a tetracycline compound, or a pharmaceutically acceptable salt, ester or a prodrug thereof, wherein the tetracycline compound is represented by formula (1):

(1)

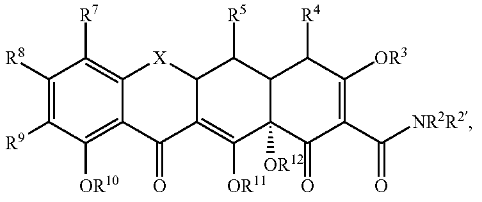

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino. arylalkyl, aryl, heterocyclic, heteroaromatic or a prodrug moiety;

$R^2$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy. alkylthio, alkylsulfinyl, alkylsulfonyl, alkylamino, or an arylalkyl;

$R^7$ and $R^8$ are each independently hydrogen, hydroxyl, halogen, thiol, alkyl, alkenyl, alkynyl, aryl, alkoxy. alkylthio, alkylsulfinyl, alkylsulfonyl, alkylamino, or an arylalkyl;

$R^9$ is aminoalkyl;

$R^{13}$ is hydrogen, hydroxy. alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that cavitary lung disease in the subject is controlled, or the advancement, severity or effects of cavitary lung disease in the subject are reduced.

In some embodiments, the present invention also provides a method of treating or preventing lymphadenitis in a subject in need thereof that comprises administering to the subject an effective amount of a tetracycline compound, or a pharmaceutically acceptable salt, ester or a prodrug thereof, wherein the tetracycline compound is represented by formula (1):

(1)

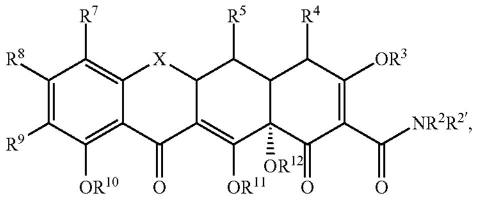

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{2'}$, $R^3$, $R^{10}$, $R^{11}$ and $R^{12}$ are each hydrogen or a pro-drug moiety;

$R^5$ is hydroxyl, hydrogen, thiol. alkanoyl, aroyl, alkaroyl, aryl, heteroaromatic, alkyl, alkenyl, alkynyl, alkoxy. alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen. thiol, alkyl, alkenyl, alkynyl, aryl, alkoxy, alkylthio, alkylsulfinyl, alkylsulfonyl, alkylamino. or an arylalkyl;

$R^7$ and $R^8$ are each independently hydrogen, hydroxyl, halogen, thiol. alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that lymphadenitis in the subject is treated or prevented.

In some embodiments, the present invention also provides a method of controlling or reducing the advancement, severity or effects of lymphadenitis in a subject in need thereof that comprises administering to the subject an effective amount of a tetracycline compound, or a pharmaceutically acceptable salt, ester or a prodrug thereof, wherein the tetracycline compound is represented by formula (1):

(1)

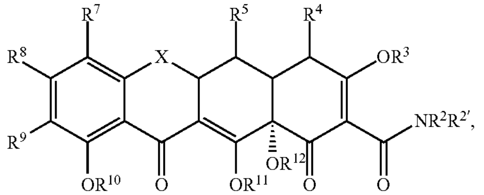

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino. arylalkyl, aryl, heterocyclic, heteroaromatic or a prodrug moiety;

$R^2$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino. or an arylalkyl;

$R^7$ and $R^8$ are each independently hydrogen, hydroxyl, halogen. thiol, alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that lymphadenitis in the subject is controlled, or the advancement, severity or effects of lymphadenitis in the subject are reduced.

In some embodiments, the present invention also provides a method of treating or preventing a soft tissue disease in a subject in need thereof that comprises administering to the subject an effective amount of a tetracycline compound, or a pharmaceutically acceptable salt, ester or a prodrug thereof, wherein the tetracycline compound is represented by formula (1):

(1)

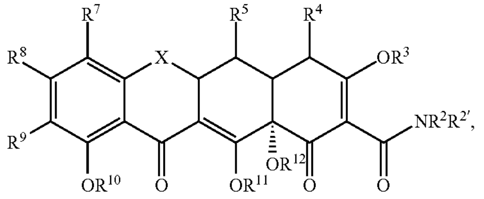

wherein:

X is CHC($R^{13}$Y'Y), $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino. arylalkyl, aryl, heterocyclic, heteroaromatic or a prodrug moiety;

$R^{2'}$, $R^3$, $R^{10}$, $R^{11}$, and $R^{12}$ are each hydrogen or a pro-drug moiety;

$R^5$ is hydroxyl, hydrogen, thiol, alkanoyl, aroyl, alkaroyl, aryl, heteroaromatic, alkyl. alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy. alkylthio, alkylsulfinyl, alkylsulfonyl, alkylamino, or an arylalkyl;

$R^7$ and $R^8$ are each independently hydrogen, hydroxyl, halogen, thiol. alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy. alkyl, alkenyl, alkynyl, alkoxy, alkylthio, alkylsulfinyl, alkylsulfonyl, alkylamino, or an arylalkyl:

Y' and Y are each independently hydrogen, halogen, hydroxyl, cyano. sulfhydryl. amino, alkyl, alkenyl, alkynyl, alkoxy, alkylthio, alkylsulfinyl, alkylsulfonyl, alkylamino, or an arylalkyl; such that the soft tissue disease in the subject is treated or prevented.

In some embodiments, the present invention also provides a method of controlling or reducing the advancement, severity or effects of a soft tissue disease in a subject in need thereof that comprises administering to the subject an effective amount of a tetracycline compound, or a pharmaceutically acceptable salt, ester or a prodrug thereof, wherein the tetracycline compound is represented by formula (1):

(1)

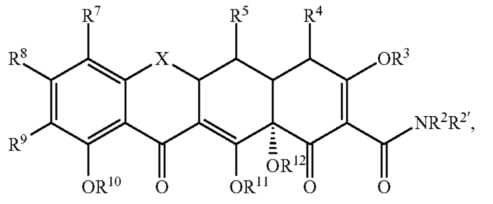

wherein:

X is CHC($R^{13}$Y'Y), $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic. heteroaromatic or a prodrug moiety:

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic. alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and R' are each independently hydrogen, methylene, absent, hydroxyl, halogen, thiol, alkyl, alkenyl, alkynyl, aryl, alkoxy. alkylthio, alkylsulfinyl, alkylsulfonyl, alkylamino, or an arylalkyl;

$R^7$ and $R^8$ are each independently hydrogen, hydroxyl, halogen, thiol, alkyl, alkenyl, alkynyl, aryl, alkoxy. alkylthio, alkylsulfinyl, alkylsulfonyl, alkylamino, or an arylalkyl;

$R^9$ is aminoalkyl;

$R^{13}$ is hydrogen, hydroxy. alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that the soft tissue disease in the subject is controlled, or the advancement, severity or effects of the soft tissue disease in the subject are reduced.

In further embodiments, the soft tissue disease is a skin disease, e.g., cellulitis.

In some embodiments, the present invention also provides a method of treating or preventing aquarium granuloma in a subject in need thereof that comprises administering to the subject an effective amount of a tetracycline compound, or a pharmaceutically acceptable salt, ester or a prodrug thereof, wherein the tetracycline compound is represented by formula (1):

(1)

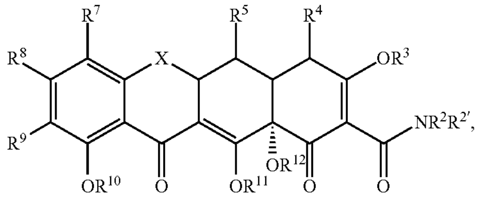

wherein:

X is CHC($R^{13}$Y'Y), $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy. alkylthio, alkylsulfinyl, alkylsulfonyl, alkylamino, arylalkyl, aryl, heterocyclic, heteroaromatic or a prodrug moiety:

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy. alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio. alkylsulfinyl, alkylsulfonyl, alkylamino, or an arylalkyl;

$R^7$ and $R^8$ are each independently hydrogen, hydroxyl, halogen, thiol. alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano. sulfhydryl. amino, alkyl, alkenyl, alkynyl, alkoxy, alkylthio, alkylsulfinyl, alkylsulfonyl, alkylamino, or an arylalkyl; such that aquarium granuloma in the subject is treated or prevented.

In some embodiments, the present invention also provides a method of controlling or reducing the advancement, severity or effects of aquarium granuloma in a subject in need thereof that comprises administering to the subject an effective amount of a tetracycline compound, or a pharmaceutically acceptable salt, ester or a prodrug thereof, wherein the tetracycline compound is represented by formula (1):

(1)

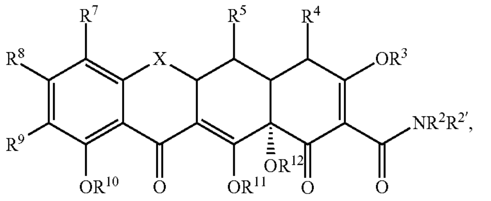

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino. arylalkyl, aryl, heterocyclic, heteroaromatic or a prodrug moiety;

$R^2$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino. or an arylalkyl;

$R^7$ and $R^8$ are each independently hydrogen, hydroxyl, halogen. thiol, alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; the that aquarium granuloma in the subject is controlled, or the advancement, severity or effects of aquarium granuloma in the subject are reduced.

In some embodiments, the present invention also provides a method of treating or preventing Buruli ulcer in a subject in need thereof that comprises administering to the subject an effective amount of a tetracycline compound, or a pharmaceutically acceptable salt, ester or a prodrug thereof, wherein the tetracycline compound is represented by formula (1):

(1)

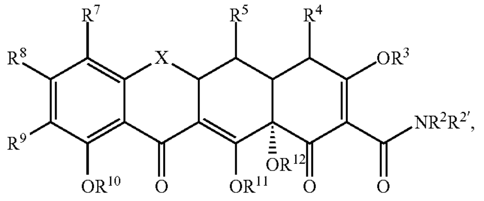

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy. alkylthio, alkylsulfinyl, alkylsulfonyl, alkylamino, arylalkyl, aryl, heterocyclic. heteroaromatic or a prodrug moiety;

$R^2$, $R^3$, $R^{10}$, $R^{11}$ and $R^{12}$ are each hydrogen or a pro-drug moiety;

$R^5$ is hydroxyl, hydrogen, thiol. alkanoyl, aroyl, alkaroyl, aryl, heteroaromatic, alkyl. alkenyl, alkynyl, alkoxy, alkylthio. alkylsulfinyl, alkylsulfonyl, alkylamino. arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ and $R^8$ are each independently hydrogen, hydroxyl, halogen. thiol, alkyl, alkenyl. alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy. alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that Buruli ulcer in the subject is treated or prevented.

In some embodiments, the present invention also provides a method of controlling or reducing the advancement, severity or effects of Buruli ulcer in a subject in need thereof that comprises administering to the subject an effective amount of a tetracycline compound, or a pharmaceutically acceptable salt, ester or a prodrug thereof, wherein the tetracycline compound is represented by formula (1):

(1)

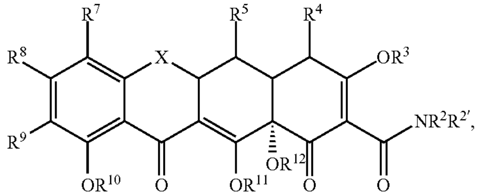

wherein:

X is $CHC(R^{13}Y'Y)$, $CR^6R''$, S, $NR^6$, or O;

$R^4$ is $NR^4R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy. alkylthio, alkylsulfinyl, alkylsulfonyl, alkylamino, arylalkyl, aryl, heterocyclic, heteroaromatic or a prodrug moiety:

$R^2$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ and $R^8$ are each independently hydrogen, hydroxyl, halogen. thiol, alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio. alkylsulfinyl. alkylsulfonyl, alkylamino, or an arylalkyl;

Y' and Y are each independently hydrogen, halogen, hydroxyl, cyano, sulfhydryl, amino. alkyl, alkenyl, alkynyl, alkoxy. alkylthio, alkylsulfinyl, alkylsulfonyl, alkylamino, or an arylalkyl; such that Buruli ulcer in the subject is controlled, or the advancement, severity or effects of Buruli ulcer in the subject are reduced.

In some embodiments, the present invention also provides a method of treating or preventing an eye disease in a subject in need thereof that comprises administering to the subject an effective amount of a tetracycline compound, or a pharmaceutically acceptable salt, ester or a prodrug thereof, wherein the tetracycline compound is represented by formula (1):

(1)

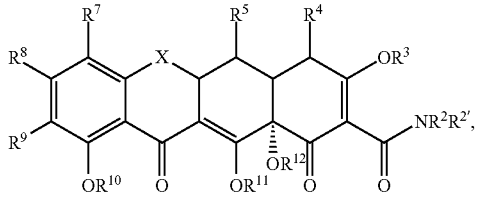

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic. heteroaromatic or a prodrug moiety:

$R^{2'}$, $R^3$, $R^{10}$, $R^{11}$ and $R^{12}$ are each hydrogen or a pro-drug moiety;

$R^5$ is hydroxyl, hydrogen, thiol. alkanoyl, aroyl, alkaroyl, aryl, heteroaromatic, alkyl, alkenyl, alkynyl, alkoxy. alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen. thiol, alkyl, alkenyl, alkynyl, aryl, alkoxy, alkylthio, alkylsulfinyl, alkylsulfonyl, alkylamino. or an arylalkyl;

$R^7$ and $R^8$ are each independently hydrogen, hydroxyl, halogen, thiol. alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that the eye disease in the subject is treated or prevented.

In some embodiments, the present invention also provides a method of controlling or reducing the advancement, severity or effects of an eye disease in a subject in need thereof that comprises administering to the subject an effective amount of a tetracycline compound, or a pharmaceutically acceptable salt, ester or a prodrug thereof, wherein the tetracycline compound is represented by formula (1):

(1)

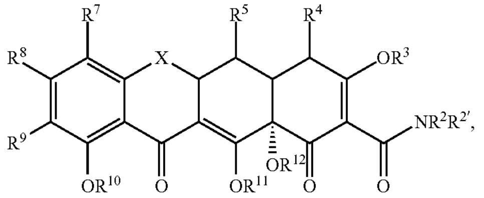

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino. arylalkyl, aryl, heterocyclic, heteroaromatic or a prodrug moiety;

$R^2$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino. or an arylalkyl;

$R^7$ and $R^8$ are each independently hydrogen, hydroxyl, halogen. thiol, alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that the eye disease in the subject is controlled, or the advancement, severity or effects of the eye disease in the subject are reduced.

In some embodiments, the present invention also provides a method of treating or preventing a bone disease in a subject in need thereof that comprises administering to the subject an effective amount of a tetracycline compound, or a pharmaceutically acceptable salt, ester or a prodrug thereof, wherein the tetracycline compound is represented by formula (1):

(1)

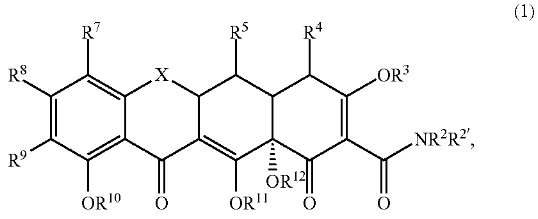

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy. alkylthio, alkylsulfinyl, alkylsulfonyl, alkylamino, arylalkyl, aryl, heterocyclic. heteroaromatic or a prodrug moiety;

$R^2$, $R^3$, $R^{10}$, $R^{11}$ and $R^{12}$ are each hydrogen or a pro-drug moiety;

$R^5$ is hydroxyl, hydrogen, thiol. alkanoyl, aroyl, alkaroyl, aryl, heteroaromatic, alkyl. alkenyl, alkynyl, alkoxy, alkylthio. alkylsulfinyl, alkylsulfonyl, alkylamino. arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ and $R^8$ are each independently hydrogen, hydroxyl, halogen. thiol, alkyl, alkenyl. alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy. alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that the bone disease in the subject is treated or prevented.

In some embodiments, the present invention also provides a method of controlling or reducing the advancement, severity or effects of a bone disease in a subject in need thereof that comprises administering to the subject an effective amount of a tetracycline compound, or a pharmaceutically acceptable salt, ester or a prodrug thereof, wherein the tetracycline compound is represented by formula (1):

(1)

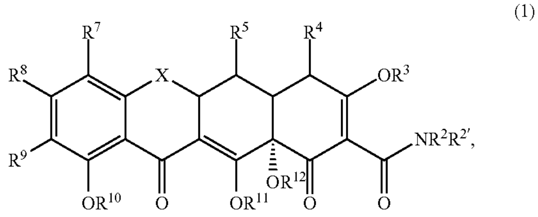

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy. alkylthio, alkylsulfinyl, alkylsulfonyl, alkylamino, arylalkyl, aryl, heterocyclic, heteroaromatic or a prodrug moiety:

$R^2$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ and $R^8$ are each independently hydrogen, hydroxyl, halogen. thiol, alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio. alkylsulfinyl. alkylsulfonyl, alkylamino, or an arylalkyl;

Y' and Y are each independently hydrogen, halogen, hydroxyl, cyano, sulfhydryl, amino. alkyl, alkenyl, alkynyl, alkoxy. alkylthio, alkylsulfinyl, alkylsulfonyl, alkylamino, or an arylalkyl; the that the bone disease in the subject is controlled, or the advancement, severity or effects of the bone disease in the subject are reduced.

In some embodiments, the present invention also provides a method of treating a subject with a lung disease that comprises administering to the subject an effective amount of a tetracycline compound, or a pharmaceutically acceptable salt, ester or a prodrug thereof, wherein the tetracycline compound is represented by formula (1):

(1)

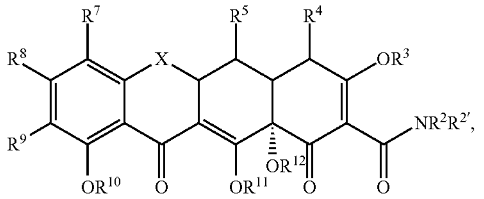

wherein:

X is $CHC(R^{13}Y'Y)$, $CR^{6'}R^6$, S, $NR^6$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic. heteroaromatic or a prodrug moiety:

$R^{2'}$, $R^3$, $R^{10}$, $R^{11}$ and $R^{12}$ are each hydrogen or a pro-drug moiety;

$R^5$ is hydroxyl, hydrogen, thiol. alkanoyl, aroyl, alkaroyl, aryl, heteroaromatic, alkyl, alkenyl, alkynyl, alkoxy. alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen. thiol, alkyl, alkenyl, alkynyl, aryl, alkoxy, alkylthio, alkylsulfinyl, alkylsulfonyl, alkylamino. or an arylalkyl;

$R^7$ and $R^8$ are each independently hydrogen, hydroxyl, halogen, thiol. alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that the subject is treated.

In further embodiments, the lung disease is selected from the group consisting of cystic fibrosis, chronic obstructive pulmonary disease (COPD), an occupational lung disease, bronchiectasis, cavitary lung disease, primary ciliary dyskinesia, allergic bronchopulmonary aspergillosis, alpha 1 antitrypsin deficiency, pneumoconiosis, interstitial lung disease, chronic aspiration syndrome and pulmonary alveolar proteinosis.

In one further embodiment, the lung disease is cystic fibrosis. In another further embodiment, the lung disease is COPD. In yet another further embodiment, the lung disease is bronchiectasis. In yet another embodiment, the lung disease is cavitary lung disease. In yet another further embodiment, the lung disease is alpha 1 antitrypsin deficiency.

In some embodiments, the present invention also provides a method of treating a subject with an immunosuppressed condition that comprises administering to the subject an effective amount of a tetracycline compound, or a pharmaceutically acceptable salt, ester or a prodrug thereof, wherein the tetracycline compound is represented by formula (1):

(1)

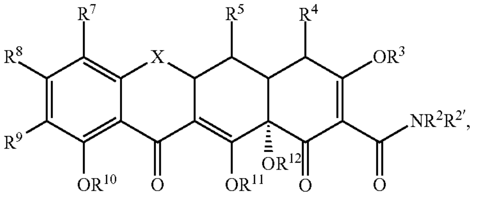

wherein:

X is $CHC(R^{13}Y'Y)$, $CR^{6'}R^{6}$, S, $NR^{6}$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino. arylalkyl, aryl, heterocyclic, heteroaromatic or a prodrug moiety;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl. alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene. absent, hydroxyl, halogen, thiol, alkyl, alkenyl, alkynyl, aryl, alkoxy. alkylthio, alkylsulfinyl, alkylsulfonyl, alkylamino, or an arylalkyl;

$R^7$ and $R^8$ are each independently hydrogen, hydroxyl, halogen. thiol, alkyl, alkenyl, alkynyl, aryl, alkoxy, alkylthio, alkylsulfinyl, alkylsulfonyl, alkylamino, or an arylalkyl;

$R^9$ is aminoalkyl;

$R^{13}$ is hydrogen, hydroxy. alkyl, alkenyl, alkynyl, alkoxy, alkylthio, alkylsulfinyl, alkylsulfonyl, alkylamino, or an arylalkyl:

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; such that the subject is treated.

In one further aspect, the immunosuppressed condition is associated with an HIV infection or AIDS. In another further aspect, the immunosuppressed condition is associated with administration of an immunosuppressive medication. In yet another further aspect, the immunosuppressive medication is administered as a part of anti-cancer therapy. In yet another further aspect, the immunosuppressive medication is administered as an immunosuppressive therapy after organ transplant.

In one aspect, the immunosuppressed condition is a genetic disorder resulting in an immunological defect. In a further aspect, the genetic disorder resulting in an immunological defect comprises a genetic defect in interferon-γ receptor or in interleukin-12.

In some embodiment, $R^9$ is $—CH_2NR'R''$, wherein R' and R'' are each independently selected from the group consisting of hydrogen, alkyl, alkenyl, alkynyl, carbonyl, acyl, aryl, heteroaryl, cycloalkyl and cycloalkenyl groups; or wherein R' and R'' are joined together to form a ring.

In some embodiments, the tetracycline compound is represented by formula (2):

(2)

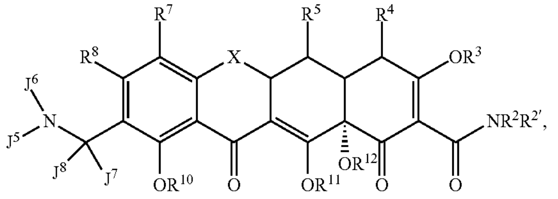

wherein:

$J^5$ and $J^6$ are each independently hydrogen, alkyl, alkenyl, alkynyl, aryl, sulfonyl, acyl, alkoxycarbonyl, alkaminocarbonyl, alkaminothiocarbonyl, substituted thiocarbonyl, substituted carbonyl, alkoxythiocarbonyl, or linked to form a ring; and $J^7$ and $J^8$ are each alkyl, halogen, or hydrogen.

In some aspects. X is $CR^{6'}R^{6}$, and wherein $R^6$ and $R^{6'}$ are both hydrogen.

In some aspects, $R^4$ is $NR^{4'}R^{4''}$, and $R^{4'}$ and $R^{4''}$ are each independently alkyl.

In some aspects, $R^7$ is dialkylamino.

In some embodiments, the tetracycline compound is represented by formula (3):

(3)

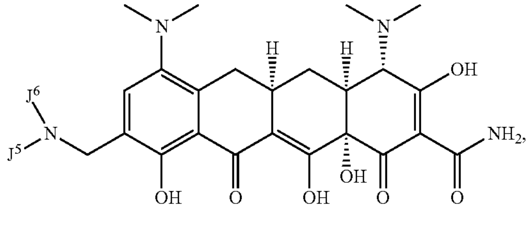

wherein $J^5$ is alkyl; and $J^6$ is hydrogen.

In some embodiments, the tetracycline compound is omadacycline represented by formula (4):

(4)

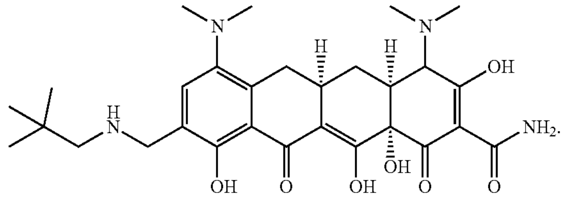

In a further embodiment, omadacycline is represented by formula (5):

(5)

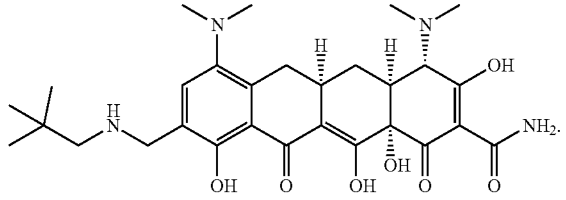

In some embodiments, the present invention also provides a method of treating or preventing tuberculosis in a subject in need thereof that comprises administering to the subject an effective amount of omadacycline, or a pharmaceutically acceptable salt, ester or a prodrug thereof, wherein omadacycline is represented by formula (4):

(4)

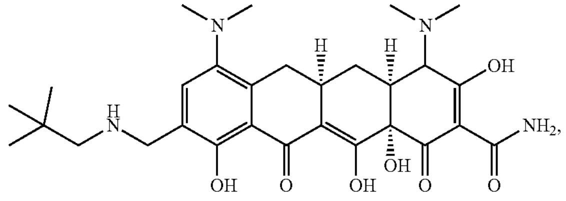

such that tuberculosis in the subject is treated or prevented.

In some embodiments, the present invention also provides a method of controlling or reducing the advancement, severity or effects of tuberculosis in a subject in need thereof that comprises administering to the subject an effective amount of omadacycline, or a pharmaceutically acceptable salt, ester or a prodrug thereof, wherein omadacycline is (4)

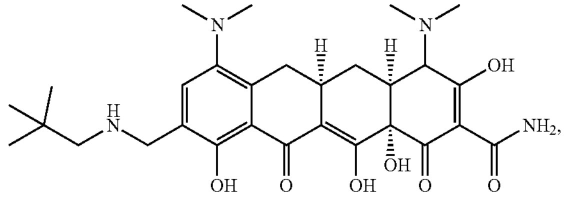

such that tuberculosis in the subject is controlled, or the advancement, severity or effects of tuberculosis in the subject are reduced.

In some aspects, the present invention also provides a method of treating or preventing leprosy in a subject in need thereof that comprises administering to the subject an effective amount of omadacycline, or a pharmaceutically acceptable salt, ester or a prodrug thereof, wherein omadacycline is represented by formula (4):

(4)

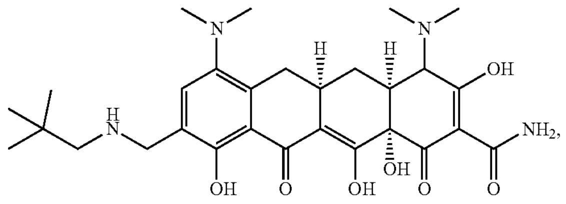

such that leprosy in the subject is treated or prevented.

In some embodiments, the present invention also provides a method of controlling or reducing the advancement, severity or effects of leprosy in a subject in need thereof that comprises administering to the subject an effective amount of omadacycline, or a pharmaceutically acceptable salt, ester or a prodrug thereof, wherein omadacycline is (4)

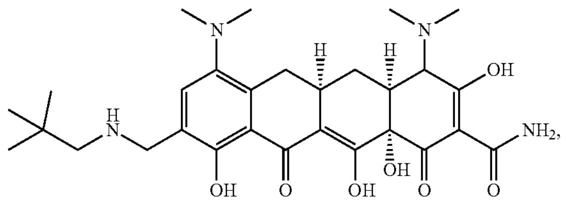

such that leprosy in the subject is controlled, or the advancement, severity or effects of leprosy in the subject are reduced.

In some embodiments, the present invention also provides a method of treating or preventing bronchiectasis in a subject in need thereof that comprises administering to the subject an effective amount of omadacycline, or a pharmaceutically acceptable salt, ester or a prodrug thereof, wherein omadacycline is represented by formula (4):

(4)

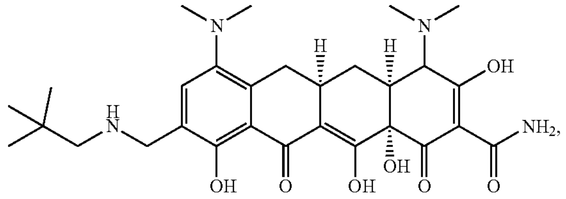

such that bronchiectasis in the subject is treated or prevented.

In some aspects, the present invention also provides a method of controlling or reducing the advancement, severity or effects of bronchiectasis in a subject in need thereof that comprises administering to the subject an effective amount of omadacycline, or a pharmaceutically acceptable salt, ester or a prodrug thereof, wherein omadacycline is (4)

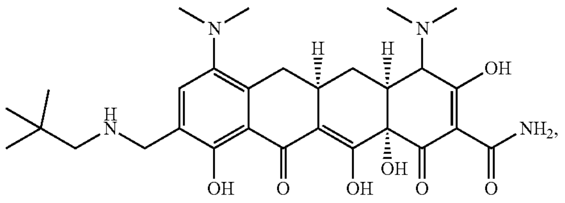

such that bronchiectasis in the subject is controlled, or the advancement, severity or effects of bronchiectasis in the subject are reduced.

In some embodiments, the present invention also provides a method of treating or preventing cavitary lung disease in a subject in need thereof that comprises administering to the subject an effective amount of omadacycline, or a pharmaceutically acceptable salt, ester or a prodrug thereof, wherein omadacycline is represented by formula (4):

(4)

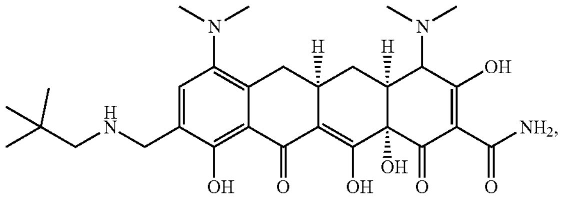

such that cavitary lung disease in the subject is treated or prevented.

In some embodiments, the present invention also provides a method of controlling or reducing the advancement, severity or effects of cavitary lung disease in a subject in need thereof that comprises administering to the subject an effective amount of omadacycline, or a pharmaceutically acceptable salt, ester or a prodrug thereof, wherein omadacycline is (4)

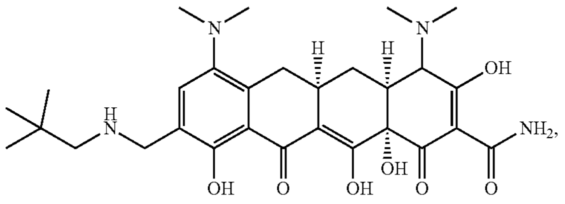

such that cavitary lung disease in the subject is controlled, or the advancement, severity or effects of cavitary lung disease in the subject are reduced.

In some aspects, the present invention also provides a method of treating or preventing lymphadenitis in a subject in need thereof that comprises administering to the subject an effective amount of omadacycline, or a pharmaceutically acceptable salt, ester or a prodrug thereof, wherein omadacycline is represented by formula (4):

(4)

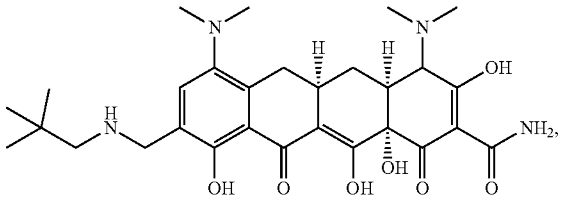

such that lymphadenitis in the subject is treated or prevented.

In some embodiments, the present invention also provides a method of controlling or reducing the advancement, severity or effects of lymphadenitis in a subject in need thereof that comprises administering to the subject an effective amount of omadacycline, or a pharmaceutically acceptable salt, ester or a prodrug thereof, wherein omadacycline is (4)

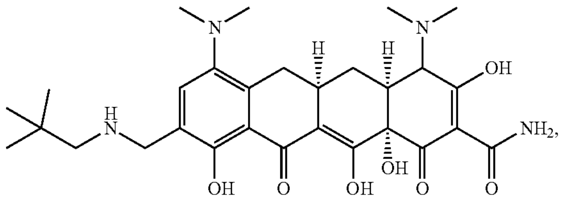

such that lymphadenitis in the subject is controlled, or the advancement, severity or effects of lymphadenitis in the subject are reduced.

In some aspects, the present invention also provides a method of treating or preventing a soft tissue disease in a subject in need thereof that comprises administering to the subject an effective amount of omadacycline, or a pharmaceutically acceptable salt, ester or a prodrug thereof, wherein omadacycline is represented by formula (4):

(4)

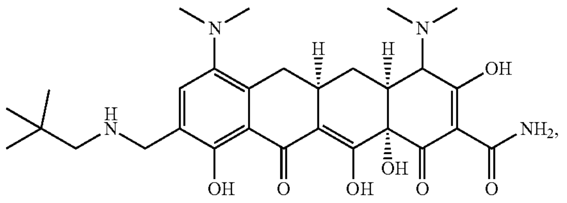

such that the soft tissue disease in the subject is treated or prevented.

In some aspects, the present invention also provides a method of controlling or reducing the advancement, severity or effects of a soft tissue disease in a subject in need thereof that comprises administering to the subject an effective amount of omadacycline, or a pharmaceutically acceptable salt, ester or a prodrug thereof, wherein omadacycline is (4)

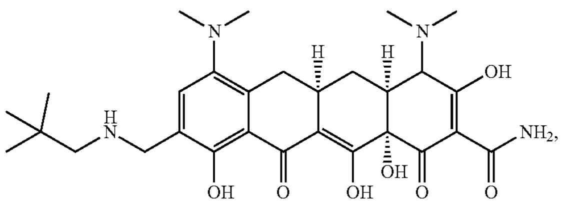

such that the soft tissue disease in the subject is controlled, or the advancement, severity or effects of the soft tissue disease in the subject are reduced.

In further embodiments, the soft tissue disease is a skin disease, e.g., cellulitis.

In some embodiments, the present invention also provides a method of treating or preventing aquarium granuloma in a subject in need thereof that comprises administering to the subject an effective amount of omadacycline, or a pharmaceutically acceptable salt, ester or a prodrug thereof, wherein omadacycline is represented by formula (4):

(4)

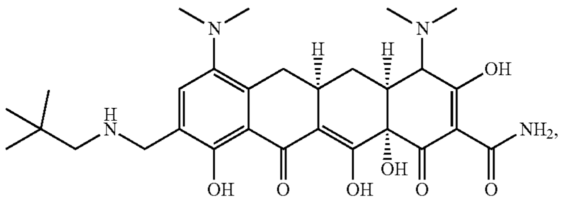

such that aquarium granuloma in the subject is treated or prevented.

In some embodiments, the present invention also provides a method of controlling or reducing the advancement, severity or effects of aquarium granuloma in a subject in need thereof that comprises administering to the subject an effective amount of omadacycline, or a pharmaceutically acceptable salt, ester or a prodrug thereof, wherein omadacycline is (4)

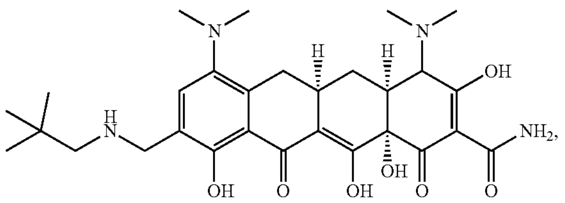

such that aquarium granuloma in the subject is controlled, or the advancement, severity or effects of aquarium granuloma in the subject are reduced.

In some aspects, the present invention also provides a method of treating or preventing Buruli ulcer in a subject in need thereof that comprises administering to the subject an effective amount of omadacycline, or a pharmaceutically acceptable salt, ester or a prodrug thereof, wherein omadacycline is represented by formula (4):

(4)

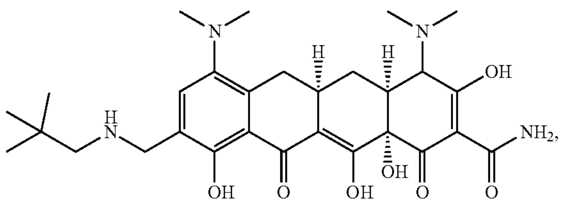

such that Buruli ulcer in the subject is treated or prevented.

In some embodiments, the present invention also provides a method of controlling or reducing the advancement, severity or effects of Buruli ulcer in a subject in need thereof that comprises administering to the subject an effective amount of omadacycline, or a pharmaceutically acceptable salt, ester or a prodrug thereof, wherein omadacycline is (4)

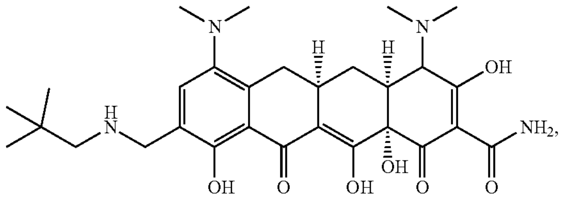

such that Buruli ulcer in the subject is controlled, or the advancement, severity or effects of Buruli ulcer in the subject are reduced.

In some embodiments, the present invention also provides a method of treating or preventing an eye disease in a subject in need thereof that comprises administering to the subject an effective amount of omadacycline, or a pharmaceutically acceptable salt, ester or a prodrug thereof, wherein omadacycline is represented by formula (4):

(4)

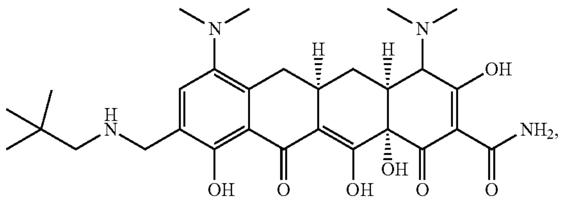

such that the eye disease in the subject is treated or prevented.

In some embodiments, the present invention also provides a method of controlling or reducing the advancement, severity or effects of an eye disease in a subject in need thereof that comprises administering to the subject an effective amount of omadacycline, or a pharmaceutically acceptable salt, ester or a prodrug thereof, wherein omadacycline is (4)

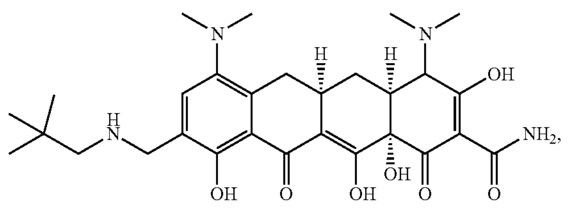

such that the eye disease in the subject is controlled, or the advancement, severity or effects of the eye disease in the subject are reduced.

In some embodiments, the present invention also provides a method of treating or preventing a bone disease in a subject in need thereof that comprises administering to the subject an effective amount of omadacycline, or a pharmaceutically acceptable salt, ester or a prodrug thereof, wherein omadacycline is represented by formula (4):

(4)

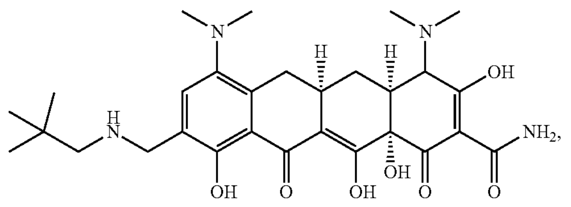

such that he bone disease in the subject is treated or prevented.

In some embodiments, the present invention also provides a method of controlling or reducing the advancement, severity or effects of a bone disease in a subject in need thereof that comprises administering to the subject an effective amount of omadacycline, or a pharmaceutically acceptable salt, ester or a prodrug thereof, wherein omadacycline is (4)

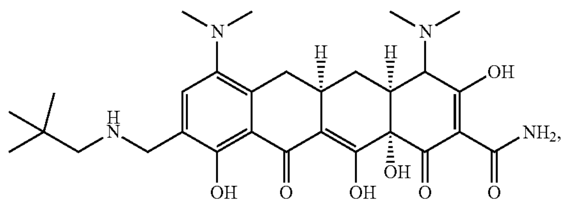

such that the bone disease in the subject is controlled, or the advancement, severity or effects of the bone disease in the subject are reduced.

In some embodiments, the present invention also provides a method of treating a subject with a lung disease that comprise administering to the subject an effective amount of omadacycline, or a pharmaceutically acceptable salt, ester or a prodrug thereof, wherein omadacycline is represented by formula (4):

(4)

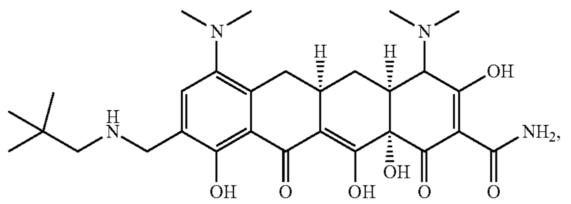

such that the subject is treated.

In some embodiments, the lung disease is selected from the group consisting of cystic fibrosis, chronic obstructive pulmonary disease (COPD), an occupational lung disease, bronchiectasis, cavitary lung disease, primary ciliary dyskinesia, allergic bronchopulmonary aspergillosis, alpha 1 antitrypsin deficiency, pneumoconiosis, interstitial lung disease, chronic aspiration syndrome and pulmonary alveolar proteinosis.

In one aspect, the lung disease is cystic fibrosis. In another aspect, the lung disease is COPD. In yet another aspect, the lung disease is bronchiectasis. In yet another aspect, the lung disease is cavitary lung disease. In yet another aspect, the lung disease is alpha 1 antitrypsin deficiency.

In some embodiments, the present invention also provides a method of treating a subject with an immunosuppressed condition that comprises administering to the subject an effective amount of omadacycline, or a pharmaceutically acceptable salt, ester or a prodrug thereof, wherein omadacycline is represented by formula (4):

(4)

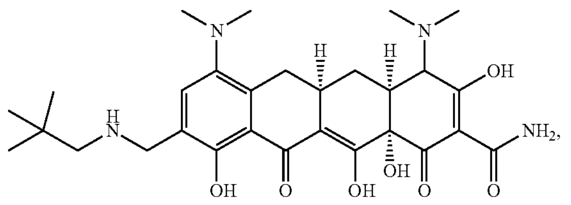

such that the subject is treated.

In some aspects, the immunosuppressed condition is associated with an HIV infection or AIDS. In other aspects, the immunosuppressed condition is associated with administration of an immunosuppressive medication. In other aspects, the immunosuppressive medication is administered as a part of anti-cancer therapy. In other aspects, the immunosuppressive medication is administered as an immunosuppressive therapy after organ transplant.

In some embodiments, the immunosuppressed condition is a genetic disorder resulting in an immunological defect, e.g., an immunological defect comprising a genetic defect in interferon-γ receptor or in interleukin-12.

In some embodiments, omadacycline is represented by formula (5):

(5)

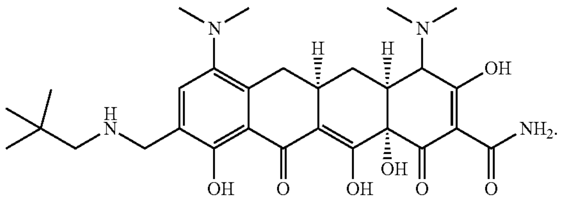

In some aspects, the tetracycline compound, or a pharmaceutically acceptable salt, ester or a prodrug thereof, is administered as a monotherapy.

In other embodiments, the tetracycline compound, or a pharmaceutically acceptable salt, ester or a prodrug thereof, is administered in combination with at least one additional anti-mycobacterial agent. In further aspects, the at least one additional anti-mycobacterial agent is selected from the group consisting of diarylquinolone, rifapentine, rifalazil, a nitroimidazole, a benzothiazinone, capreomycin, clofazimine, cycloserine, dapsone, a thiocarbamide, ethambutol, DC-159a, a nitrobenzthiazole, sutezolid (PNU-100480), AZD-5847, posizolid (AZD-2563), para-aminosalicylic acid, SQ-109, SQ-609, a capuramycin, a caprazene nucleoside, an isothiazoloquinolone, thioridazine, thiacetazone, dirithromycin, roxithromycin, telithromycin, azithromycin, clarithromycin, erythromycin, amikacin, kanamycin, streptomycin, levofloxacin, moxifloxacin, gatifloxacin, linezolid, rifalazil, imipenem, meropenem, clavulanate and isoniazid.

In some aspects, the tetracycline compound, or a pharmaceutically acceptable salt, ester or a prodrug thereof, is administered for a period of time lasting from about 1 week to about 12 weeks. In some aspects, the tetracycline compound, or a pharmaceutically acceptable salt, ester or a prodrug thereof, is administered for a period of time lasting from about 1 month to about 24 months. In other aspects, the tetracycline compound, or a pharmaceutically acceptable salt, ester or a prodrug thereof, is administered for a period of time of more than 24 months.

In some embodiments, the tetracycline compound, or a pharmaceutically acceptable salt, ester or a prodrug thereof, is administered parenterally, orally, topically or via an aerosol. In some aspects, the tetracycline compound, or a pharmaceutically acceptable salt, ester or a prodrug thereof, is administered parenterally, e.g., intravenously. In some aspects, the tetracycline compound, or a pharmaceutically acceptable salt, ester or a prodrug thereof, is administered intravenously at a dose of about 100 to about 300 mg. In further aspects, the tetracycline compound, or a pharmaceutically acceptable salt, ester or a prodrug thereof, is administered intravenously at a dose of about 100 mg, about 150 mg, about 200 mg, about 250 mg or about 300 mg.

In some embodiments, the tetracycline compound, or a pharmaceutically acceptable salt, ester or a prodrug thereof, is administered orally. In some embodiments, the tetracycline compound, or a pharmaceutically acceptable salt, ester or a prodrug thereof, is administered orally at a dose of about 150 to about 600 mg. In further aspects, the tetracycline compound, or a pharmaceutically acceptable salt, ester or a prodrug thereof, is administered orally at a dose of about 150, about 300 mg, about 450 mg or about 600 mg.

In some embodiments, the tetracycline compound, or a pharmaceutically acceptable salt, ester or a prodrug thereof, is administered via an aerosol. In some embodiments, administration of the tetracycline compound, or a pharmaceutically acceptable salt, ester or a prodrug thereof, via an aerosol comprises the use of an aerosol dispenser comprising tetracycline compound, or a pharmaceutically acceptable salt, ester or a prodrug thereof at a dose of about 1 mg to about 1000 mg. In further embodiments, the aerosol dispenser comprises tetracycline compound, or a pharmaceutically acceptable salt, ester or a prodrug thereof, at a dose of about 1 mg, about 5 mg, about 10 mg, about 30 mg, about 50 mg, about 80 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg or about 1000 mg.

In some aspects, the tetracycline compound, or a pharmaceutically acceptable salt, ester or a prodrug thereof, is administered topically by applying to an affected area pharmaceutical composition adapted for topical administration comprising tetracycline compound, or a pharmaceutically acceptable salt, ester or a prodrug thereof.

In some aspects, the pharmaceutical composition comprises the tetracycline compound, or a pharmaceutically acceptable salt, ester or a prodrug thereof, at a concentration of about 0.01% to about 20% w/v, based on the volume of the composition. In some aspects, the pharmaceutical composition comprises the tetracycline compound, or a pharmaceutically acceptable salt, ester or a prodrug thereof, at a concentration of about 0.01% w/v, about 0.05% w/v, about 0.1% w/v, about 0.5% w/v, about 1% w/v, about 5% w/v, about 10% w/v, about 15% w/v or about 20% w/v.

In some embodiments, the pharmaceutical composition comprises the tetracycline compound, or a pharmaceutically acceptable salt, ester or a prodrug thereof, at a concentration of about 0.01% to about 20% w/w, based on the volume of the composition. In some embodiments, the pharmaceutical composition comprises the tetracycline compound, or a pharmaceutically acceptable salt, ester or a prodrug thereof, at a concentration of about 0.01% w/w, about 0.05% w/w, about 0.1% w/w, about 0.5% w/w, about 1% w/w, about 5% w/w, about 10% w/w, about 15% w/w or about 20% w/w.

In some embodiments, administration of the tetracycline compound, or a pharmaceutically acceptable salt, ester or a prodrug thereof, comprises administering one or more loading doses of the tetracycline compound, or a pharmaceutically acceptable salt, ester or a prodrug thereof, followed by one or more maintenance doses of the tetracycline compound, or a pharmaceutically acceptable salt, ester or a prodrug thereof.

In some aspects, the loading dose is an intravenous dose or an oral dose. In further aspects, the loading dose is an intravenous daily dose of about 200 mg or an oral daily dose of about 450 mg. In some aspects, the maintenance dose is an intravenous daily dose of about 100 mg or an oral daily dose of about 300 mg.

In some embodiments, administration of the tetracycline compound, or a pharmaceutically acceptable salt, ester or a prodrug thereof, comprises administering the same dose of tetracycline compound, or a pharmaceutically acceptable salt, ester or a prodrug thereof, throughout the treatment period.

In some embodiments, the subject is immunocompetent. In other embodiments, the subject is immunocompromised.

In some embodiments, the subject is a mammal. In further embodiments, the mammal is selected from the group consisting of a human, a nonhuman primate, a cow, a sheep, a pig, a goat, a horse, a dog, a cat, a mouse, a rat and a guinea pig. In a specific embodiment, the subject is a human.

In some embodiments, the subject has been determined to have a mycobacterial infection.

In some embodiments, methods of the present invention further comprise determining that the subject has a mycobacterial infection prior to administering the tetracycline compound, or a pharmaceutically acceptable salt, ester or a prodrug thereof, to the subject.

BRIEF DESCRIPTION OF THE DRAWINGS

FIG. 1, Panel B is a graph showing concentration- and time-dependent bactericidal activity of tigecycline towards *M. abscessus* subsp. *abscessus*.

DETAILED DESCRIPTION OF THE INVENTION

Figure 1:
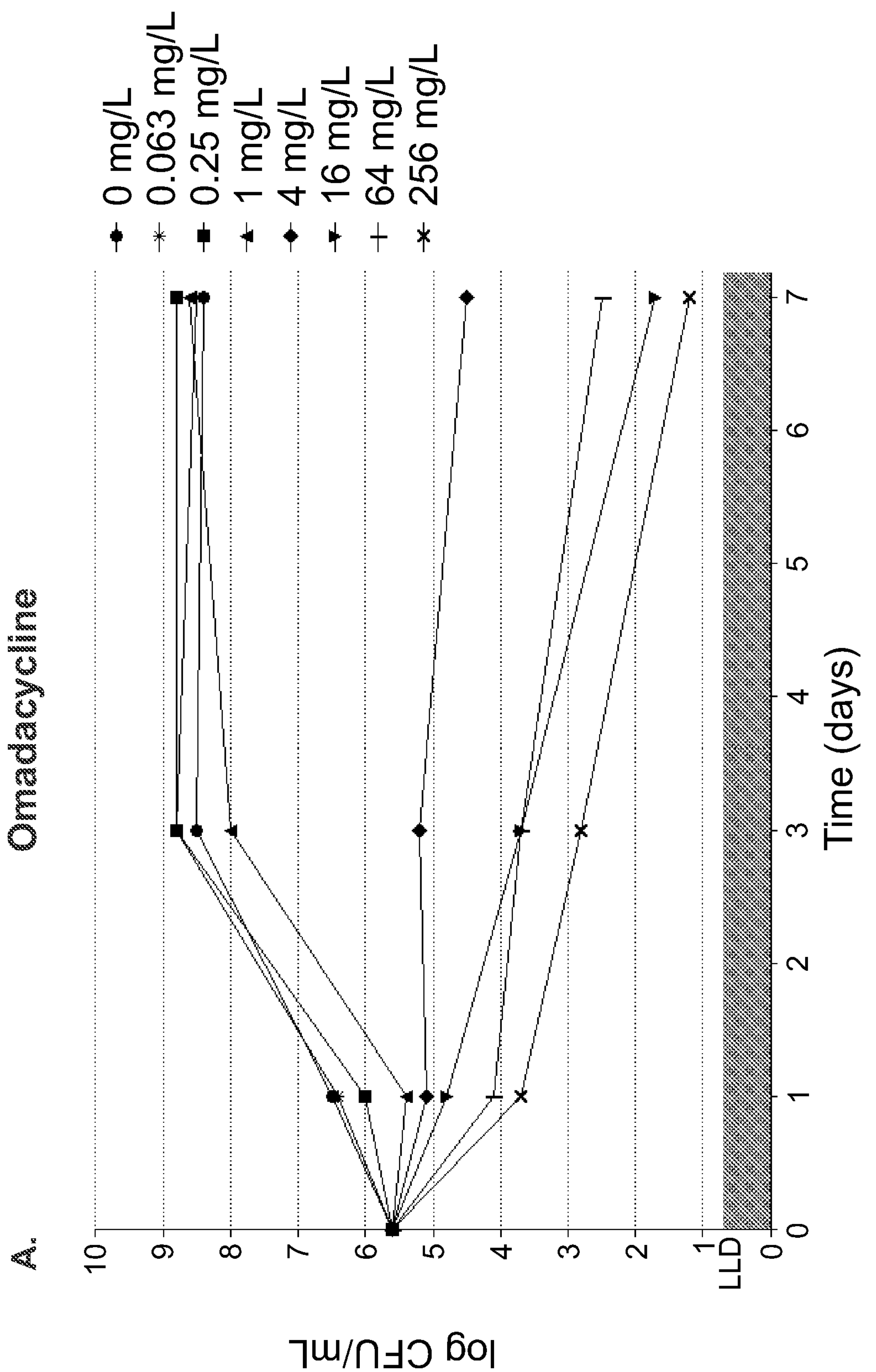
FIG. 1, Panel A is a graph showing concentration- and time-dependent bactericidal activity of omadacycline towards *M. abscessus* subsp. *abscessus*.
Figure 1:
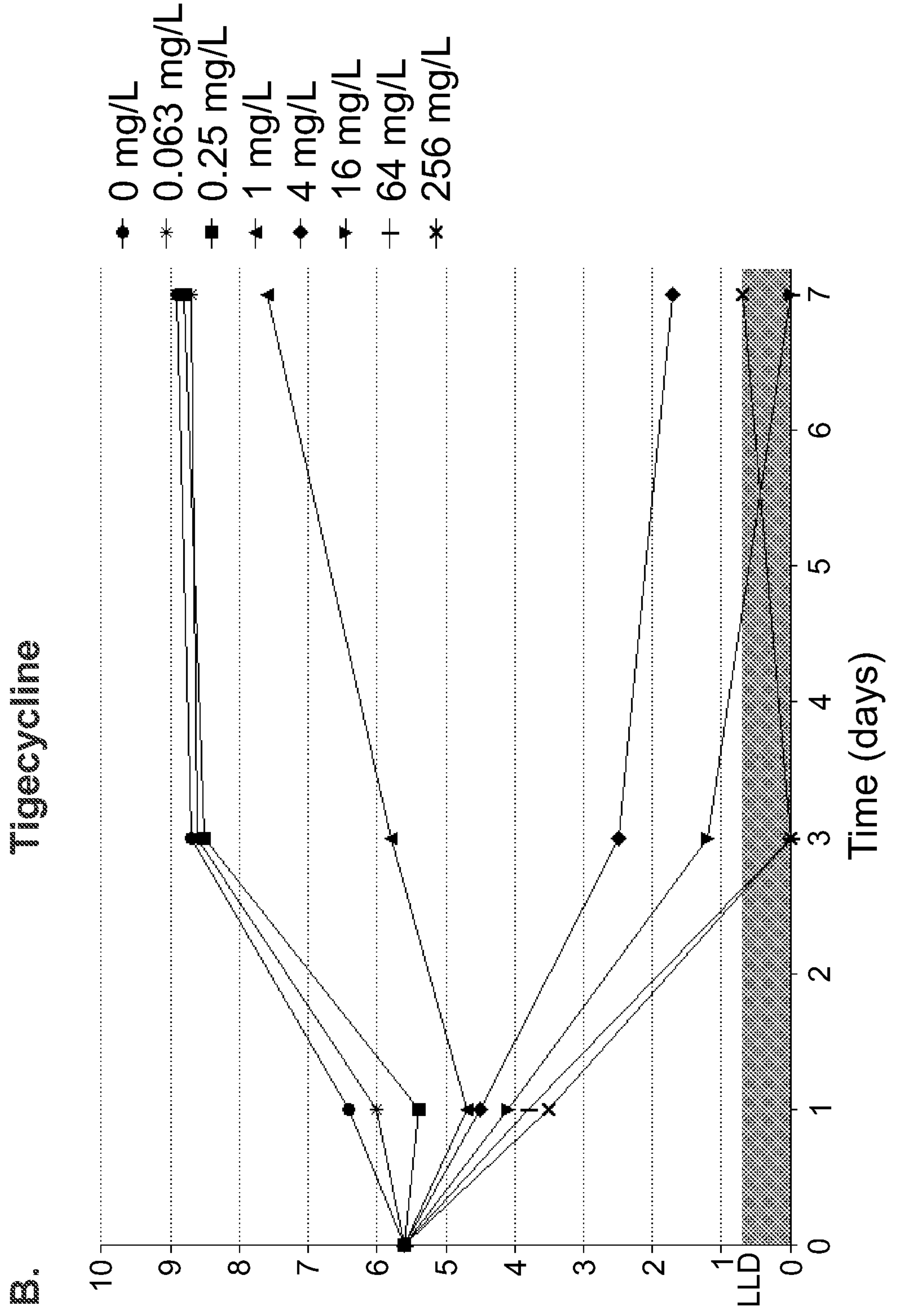

Methods of Treating or Preventing Mycobacterial Infections

The present invention provides methods of treating or preventing a mycobacterial infection or treating or preventing a mycobacterial disease in a subject in need thereof. The methods of treating or preventing a mycobacterial infection comprise administering to the subject an effective amount of a tetracycline compound, or a pharmaceutically acceptable salt, ester or a prodrug thereof, wherein the tetracycline compound is represented by formula (1):

(1)

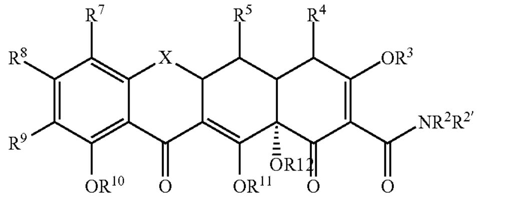

wherein:

X is $CHC(R^{13}Y'Y)$, $CR^{6'}R^{6}$, S, $NR^{6}$, or O;

$R^4$ is $NR^{4'}R^{4''}$, alkyl, alkenyl, alkynyl, aryl, hydroxyl, halogen, or hydrogen;

$R^2$, $R^{4'}$, $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl. alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene. absent, hydroxyl, halogen. thiol, alkyl, alkenyl, alkynyl, aryl, alkoxy. alkylthio, alkylsulfinyl, alkylsulfonyl, alkylamino, or an arylalkyl;

$R^7$ and $R^8$ are each independently hydrogen, hydroxyl, halogen. thiol, alkyl, alkenyl. alkynyl, aryl, alkoxy. alkylthio, alkylsulfinyl, alkylsulfonyl, alkylamino, or an arylalkyl;

$R^9$ is aminoalkyl;

$R^{13}$ is hydrogen, hydroxy. alkyl, alkenyl, alkynyl, alkoxy, alkylthio, alkylsulfinyl, alkylsulfonyl, alkylamino, or an arylalkyl:

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, such that a mycobacterial infection or a mycobacterial disease in the subject is treated or prevented.

In some examples, $R^9$ is aminomethyl, e.g., $-CH_2NR'R''$. In some examples, each of R' and R" of the aminomethyl moiety may be independently selected from the group consisting of hydrogen, alkyl, alkenyl, alkynyl, carbonyl, acyl, aryl, heteroaryl, cycloalkyl or cycloalkenyl groups, or wherein R' and R" may be joined together to form a ring, e.g., cycloalkyl, cycloalkenyl or aryl.

In some examples, R' of the aminomethyl moiety is hydrogen and R" of the aminomethyl moiety is alkyl, cycloalkyl or cycloalkenyl. In further examples, R" is a cyclopropyl, cyclobutyl, cyclopentyl or cyclohexyl. In other further examples, R" is alkyl, e.g., alkyl substituted with methyl, ethyl, isopropyl or tert-butyl.

In some examples, R' and R" of the aminomethyl moiety are joined together to form a ring, e.g., a cycloalkyl moiety, such as cyclopropyl, cyclobutyl, cyclopentyl or cyclohexyl. In some examples, the cycloalkyl moiety may further be substituted, e.g., with an alkyl, cycloalkyl, heterocyclyl or a halogen. In some examples, the cycloalkyl moiety may be bicyclic or tricyclic.

In other examples, $R^9$ is $-CH_2NR^{9c}(=Z')ZR^{9a}$, wherein Z is $CR^{9d}R^{9e}$, S, $NR^{9b}$ or O; Z' is $NR^{9f}$, O or S; and $R^{9a}$, $R^{9b}$, $R^{9c}$, $R^{9d}$, $R^{9e}$ and $R^{9f}$ are each independently hydrogen. acyl, alkyl, alkenyl, alkynyl, alkoxy, alkylthio. alkylsulfinyl, alkylsulfonyl, alkylamino, arylalkyl, aryl, heterocyclic, heteroaromatic or a prodrug moiety.

In some examples, $R^9$ is $-CH_2NR^{9c}(=Z')ZR^{9a}$. Examples of $R^{9c}$ include hydrogen. In some embodiments, Z' may be S. NH, or O. Examples of Z include NR (e.g., when $R^9$ is hydrogen, alkyl, etc.), O or S.

Examples of $R^{9a}$ groups may include aryl groups. such as substituted and unsubstituted phenyl. Examples of possible substituents of aryl $R^{9a}$ groups include, but are not limited to, alkyl (e.g., methyl, ethyl, propyl, butyl, pentyl, hexyl. perfluoromethyl. perchloromethyl. etc.). alkenyl, halogen (e.g., fluorine, chlorine, bromine, iodine, etc.), hydroxyl, alkoxy (e.g., methoxy, ethoxy, propoxy, perfluoro methoxy, perchloro methoxy, etc.). alkylcarbonyloxy, arylcarbonyloxy, alkoxycarbonyloxy, aryloxycarbonyloxy. carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, silyl, aminocarbonyl, alkylthiocarbonyl, phosphate, phosphonato, phosphinato, cyano, amino. acylamino, amido, imino, sulfhydryl, alkylthio, arylthio, thiocarboxylate. sulfate, alkylsulfinyl, sulfonato. sulfamoyl. sulfonamido, nitro, acetyl, alkyl. cyano, azido, heterocyclyl, alkylaryl, aryl and heteroaryl groups.

In certain embodiments, at least one of the substituents present on the substituted phenyl is nitro. alkoxy (e.g., methoxy, methylenedioxy, perfluoromethoxy), alkyl (e.g., methyl, ethyl, propyl, butyl, or pentyl), acetyl, halogen (e.g., fluorine, chlorine, bromine, or iodine), or amino (e.g., dialkylamino). In certain embodiments. the alkoxy group is perhalogenated, e.g., perfluoromethoxy.

Examples of aryl $R^9$ groups include, but are not limited to, unsubstituted phenyl, para-nitrophenyl, para-methoxy phenyl. para-perfluoromethoxy phenyl, para-acetyl phenyl, 3,5-methylenedioxyphenyl, 3,5-diperfluoromethyl phenyl. para-bromo phenyl, para-chloro phenyl, and para-fluoro phenyl.

Other examples of aryl $R^{9a}$ groups include substituted and unsubstituted heterocycles (e.g., furanyl, imidazolyl, benzothiophenyl. benzofuranyl. quinolinyl, isoquinolinyl. benzodioxazolyl, benzoxazolyl, benzothiazolyl, benzoimidazolyl, methylenedioxyphenyl. indolyl, thienyl, pyrimidyl, pyrazinyl, purinyl, pyrazolyl, pyrolidinyl, oxazolyl, isooxazolyl. naphthridinyl, thiazolyl, isothiazolyl, or deazapurinyl) and substituted and unsubstituted biaryl groups, such as naphthyl and fluorene.

$R^{9a}$ also may be substituted or unsubstituted alkyl, e.g., methyl, ethyl. propyl, butyl, pentyl, etc. Examples of substituents include, but are not limited to, halogens (e.g., fluorine, bromine, chlorine, iodine, etc.), hydroxyl, alkoxy (e.g., methoxy, ethoxy, propoxy, butoxy, etc.), alkylcarbonyloxy, arylcarbonyloxy, alkoxycarbonyloxy. aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl. silyl, aminocarbonyl, alkylthiocarbonyl, phosphate, phosphonato, phosphinato, cyano, amino, acylamino, amidino, imino, sulfhydryl, alkylthio, arylthio, thiocarboxylate, sulfate. alkylsulfinyl, sulfonato, sulfamoyl. sulfonamido, nitro, trifluoromethyl, cyano, azido, alkenyl, heterocyclyl, alkylaryl, aryl and heteroaryl.

$R^{9a}$ also can be substituted or unsubstituted alkenyl. Examples of substituents for alkenyl $R^9$ groups include those listed above for alkyl $R^{9a}$ groups. Examples of alkenyl $R^{9a}$ groups include pent-1-enyl.

In an embodiment, Z' is NH, Z is NH, and $R^{9a}$ is alkyl.

In some examples, methods of the present invention comprise administering to a subject a tetracycline compound is represented by formula (2):

(2)

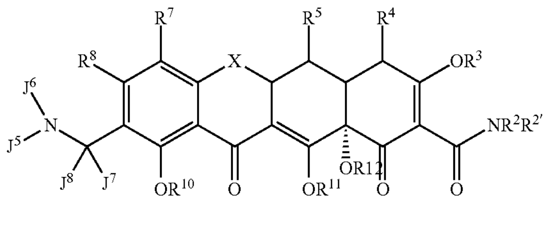

wherein:

$J^5$ and $J^6$ are each independently hydrogen, alkyl, alkenyl, alkynyl, aryl, sulfonyl, acyl, alkoxycarbonyl, alkaminocarbonyl, alkaminothiocarbonyl, substituted thiocarbonyl. substituted carbonyl, alkoxythiocarbonyl, or linked to form a ring;

$J^7$ and $J^8$ are each alkyl, halogen, or hydrogen; and

X, $R^2$, $R^{2'}$, $R^3$, $R^{4'}$, $R^{4''}$, $R^5$, $R^6$, $R^{6'}$, $R^7$, $R^8$, $R^{10}$, $R^{11}$ and $R^{12}$ are as defined above for formula (1), or pharmaceutically acceptable salts, esters and prodrugs thereof.

In some embodiments for formula (1) and formula (2), X is $CR^{6'}R^6$. In further examples, both $R^6$ and $R^{6'}$ are each hydrogen.

In some embodiments for formula (1) and formula (2), $R^4$ is $NR^{4'}R^{4''}$, and $R^{4'}$ and $R^{4''}$ are each independently alkyl. In further examples, $R^{4'}$ and $R^{4''}$ are each methyl.

In some embodiments for formula (1) and formula (2), $R^7$ is dialkylamino, e.g., dimethylamino.

In some embodiments for formula (1) and formula (2), $R^5$ is hydrogen.

In some embodiments for formula (1) and formula (2), $R^8$ is hydrogen.

In some examples, methods of the present invention comprise administering to a subject a tetracycline compound is represented by formula (3):

(3)

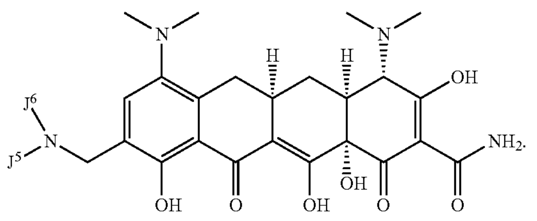

wherein $J^5$ is alkyl; and $J^6$ is hydrogen, or pharmaceutically acceptable salts, prodrugs and esters thereof.

In some examples, methods of the present invention for treating or preventing a mycobacterial infection or treating or preventing a mycobacterial disease comprise administering to a subject any 9-aminomethyl substituted tetracycline compound as listed in U.S. Pat. Nos. 7,326,696, 7,553,828 and 9,365,499, the entire contents of each of which are hereby incorporated herein by reference.

In some examples, methods of the present invention for treating or preventing a mycobacterial infection or treating or preventing a mycobacterial disease comprise administering to a subject in need thereof any tetracycline compound as listed in Table 1 below:

TABLE 1
Tetracycline Compounds
| Compound number | Structure |
|---|---|
| 1 | 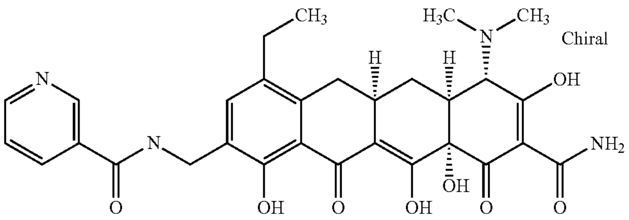 [SMILES: CCc1cc(CNC(=O)c2cccnc2)c(O)c2c1C[C@H]1C[C@H]3[C@H](N(C)C)C(O)=C(C(N)=O)C(=O)[C@@]3(O)C(O)=C1C2=O] |
| 2 | 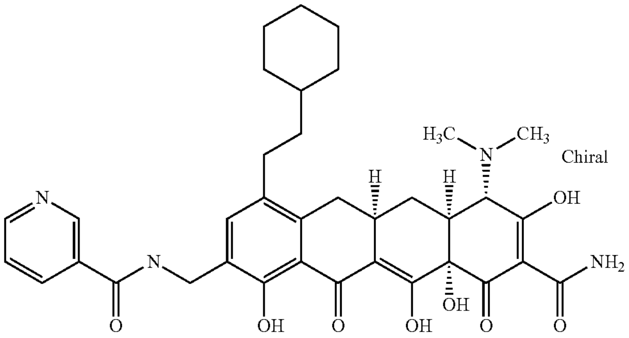 [SMILES: CN(C)[C@@H]1C(O)=C(C(N)=O)C(=O)[C@@]2(O)C(O)=C3C(=O)c4c(O)c(CNC(=O)c5cccnc5)cc(CCC5CCCCC5)c4C[C@H]3C[C@@H]12] |
| 3 | 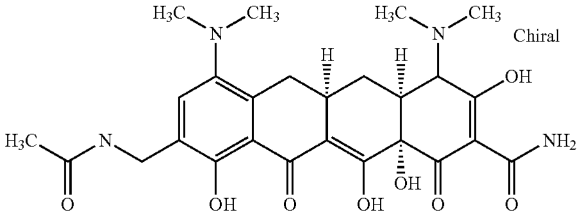 [SMILES: CC(=O)NCc1cc(N(C)C)c2c(c1O)C(=O)C1=C(O)[C@]3(O)C(=O)C(C(N)=O)=C(O)C(N(C)C)[C@@H]3C[C@@H]1C2] |
| 4 | 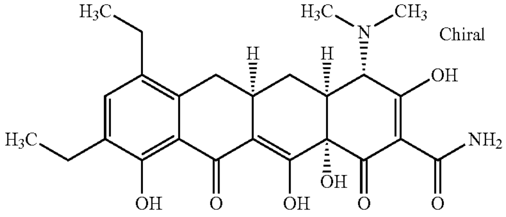 [SMILES: CCc1cc(CC)c2c(c1O)C(=O)C1=C(O)[C@]3(O)C(=O)C(C(N)=O)=C(O)[C@@H](N(C)C)[C@@H]3C[C@@H]1C2] |
| 5 | 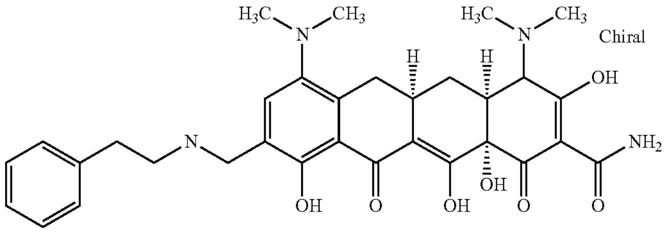 [SMILES: CN(C)c1cc(CNCCc2ccccc2)c(O)c2c1C[C@H]1C[C@H]3C(N(C)C)C(O)=C(C(N)=O)C(=O)[C@@]3(O)C(O)=C1C2=O] |
| 6 | 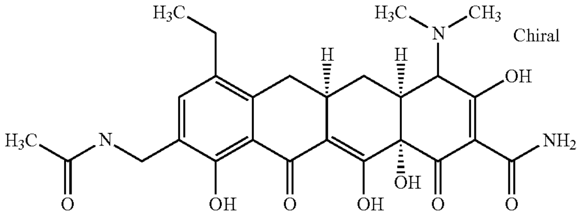 [SMILES: CCc1cc(CNC(C)=O)c(O)c2c1C[C@H]1C[C@H]3C(N(C)C)C(O)=C(C(N)=O)C(=O)[C@@]3(O)C(O)=C1C2=O] |

TABLE 1-continued
| Tetracycline Compounds | |
|---|---|
| Compound number | Structure |
| 8 | 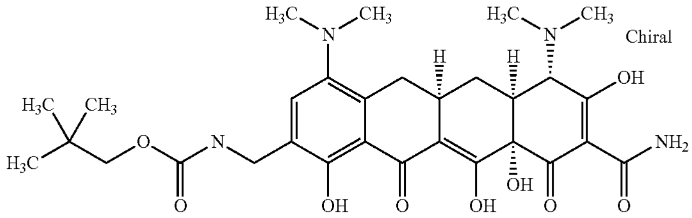 [SMILES: CN(C)c1cc(CNC(=O)OCC(C)(C)C)c(O)c2c1C[C@H]1C[C@H]3[C@H](N(C)C)C(O)=C(C(N)=O)C(=O)[C@@]3(O)C(O)=C1C2=O] |
| 9 | 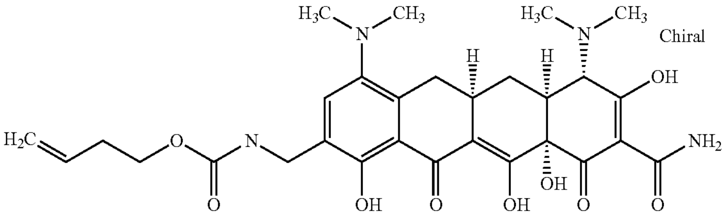 [SMILES: C=CCCOC(=O)NCc1cc(N(C)C)c2c(c1O)C(=O)C1=C(O)[C@]3(O)C(=O)C(C(N)=O)=C(O)[C@@H](N(C)C)[C@@H]3C[C@@H]1C2] |
| 10 | 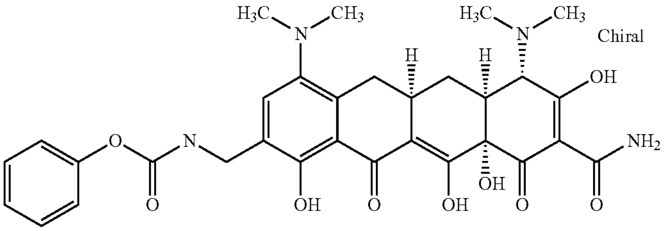 [SMILES: CN(C)c1cc(CNC(=O)Oc2ccccc2)c(O)c2c1C[C@H]1C[C@H]3[C@H](N(C)C)C(O)=C(C(N)=O)C(=O)[C@@]3(O)C(O)=C1C2=O] |
| 11 | 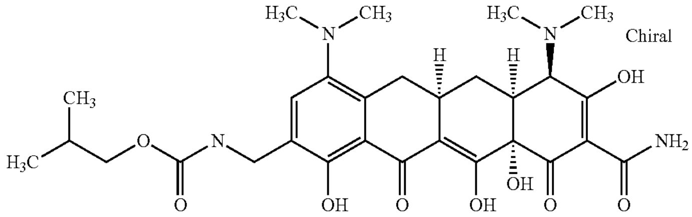 [SMILES: CC(C)COC(=O)NCc1cc(N(C)C)c2c(c1O)C(=O)C1=C(O)[C@]3(O)C(=O)C(C(N)=O)=C(O)[C@H](N(C)C)[C@@H]3C[C@@H]1C2] |
| 12 | 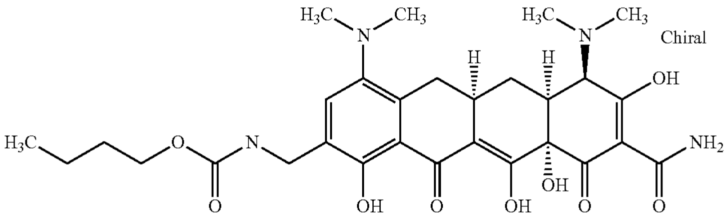 [SMILES: CCCCOC(=O)NCc1cc(N(C)C)c2c(c1O)C(=O)C1=C(O)[C@]3(O)C(=O)C(C(N)=O)=C(O)[C@H](N(C)C)[C@@H]3C[C@@H]1C2] |
| 13 | 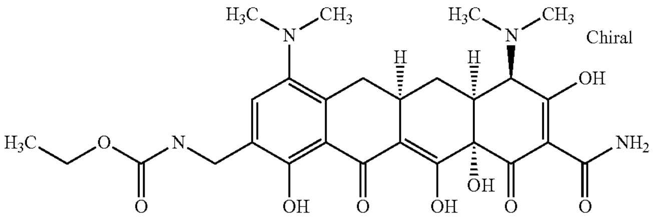 [SMILES: CCOC(=O)NCc1cc(N(C)C)c2c(c1O)C(=O)C1=C(O)[C@]3(O)C(=O)C(C(N)=O)=C(O)[C@H](N(C)C)[C@@H]3C[C@@H]1C2] |

TABLE 1-continued
| Tetracycline Compounds | |
|---|---|
| Compound number | Structure |
| 14 | 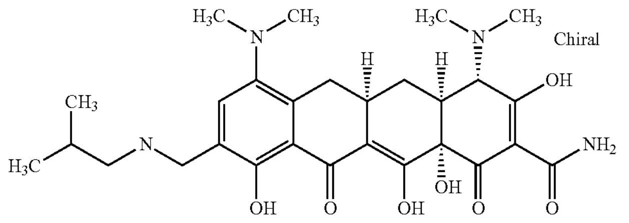 |
| 15 | 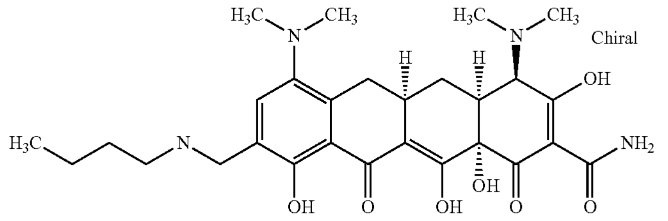 [SMILES: CCCCNCc1cc(N(C)C)c2c(c1O)C(=O)C1=C(O)[C@]3(O)C(=O)C(C(N)=O)=C(O)[C@H](N(C)C)[C@@H]3C[C@@H]1C2] |
| 16 | 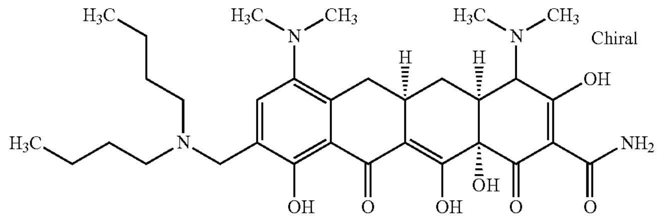 [SMILES: CCCCN(CCCC)Cc1cc(N(C)C)c2c(c1O)C(=O)C1=C(O)[C@]3(O)C(=O)C(C(N)=O)=C(O)C(N(C)C)[C@@H]3C[C@@H]1C2] |
| 17 | 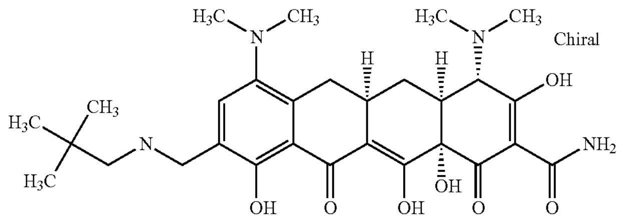 |
| 18 | 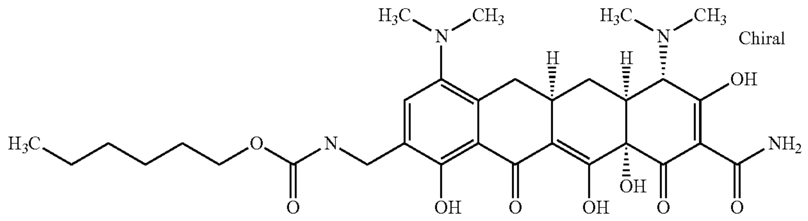 [SMILES: CCCCCCOC(=O)NCc1cc(N(C)C)c2c(c1O)C(=O)C1=C(O)[C@]3(O)C(=O)C(C(N)=O)=C(O)[C@@H](N(C)C)[C@@H]3C[C@@H]1C2] |
| 19 | 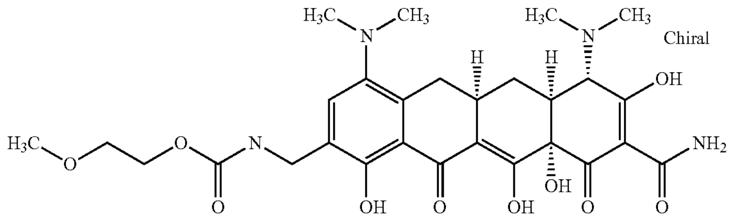 |

TABLE 1-continued
| Tetracycline Compounds | |
|---|---|
| Compound number | Structure |
| 20 | 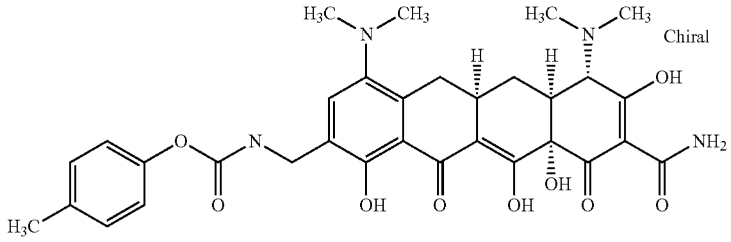 [SMILES: Cc1ccc(OC(=O)NCc2cc(N(C)C)c3c(c2O)C(=O)C2=C(O)[C@]4(O)C(=O)C(C(N)=O)=C(O)[C@@H](N(C)C)[C@@H]4C[C@@H]2C3)cc1] |
| 21 | 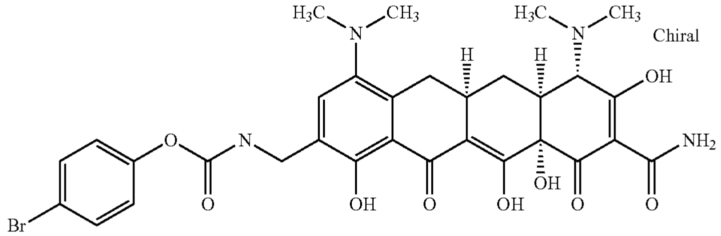 [SMILES: CN(C)c1cc(CNC(=O)Oc2ccc(Br)cc2)c(O)c2c1C[C@H]1C[C@H]3[C@H](N(C)C)C(O)=C(C(N)=O)C(=O)[C@@]3(O)C(O)=C1C2=O] |
| 22 | 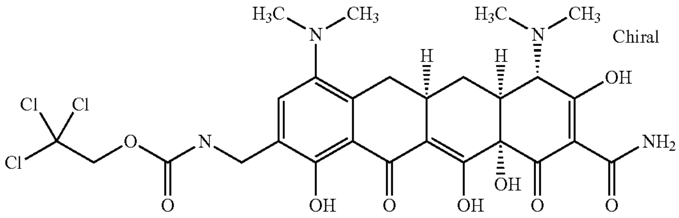 [SMILES: CN(C)c1cc(CNC(=O)OCC(Cl)(Cl)Cl)c(O)c2c1C[C@H]1C[C@H]3[C@H](N(C)C)C(O)=C(C(N)=O)C(=O)[C@@]3(O)C(O)=C1C2=O] |
| 23 | 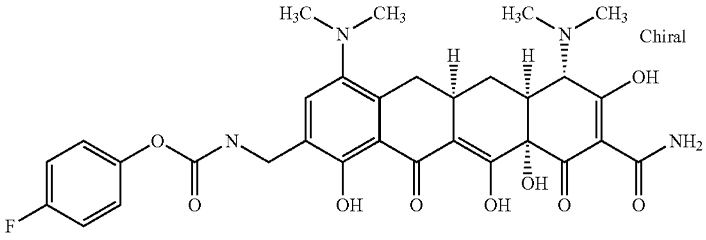 [SMILES: CN(C)c1cc(CNC(=O)Oc2ccc(F)cc2)c(O)c2c1C[C@H]1C[C@H]3[C@H](N(C)C)C(O)=C(C(N)=O)C(=O)[C@@]3(O)C(O)=C1C2=O] |
| 24 | 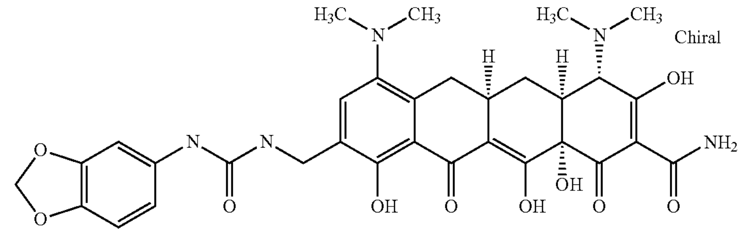 [SMILES: CN(C)c1cc(CNC(=O)Nc2ccc3c(c2)OCO3)c(O)c2c1C[C@H]1C[C@H]3[C@H](N(C)C)C(O)=C(C(N)=O)C(=O)[C@@]3(O)C(O)=C1C2=O] |
| 25 | 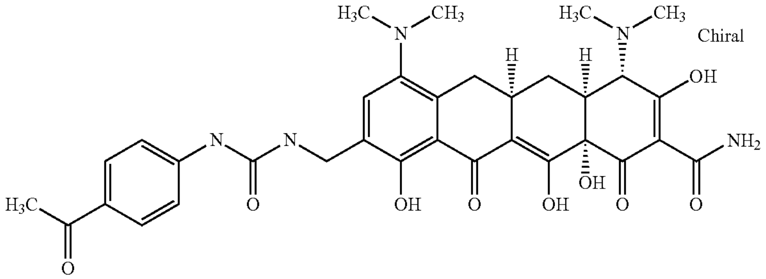 [SMILES: CC(=O)c1ccc(NC(=O)NCc2cc(N(C)C)c3c(c2O)C(=O)C2=C(O)[C@]4(O)C(=O)C(C(N)=O)=C(O)[C@@H](N(C)C)[C@@H]4C[C@@H]2C3)cc1] |

TABLE 1-continued
| Tetracycline Compounds | |
|---|---|
| Compound number | Structure |
| 26 | 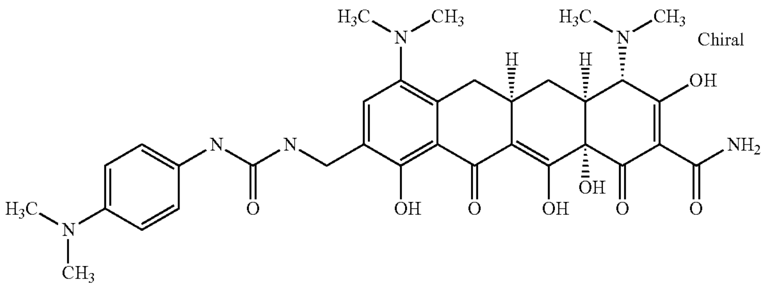 [SMILES: CN(C)c1ccc(NC(=O)NCc2cc(N(C)C)c3c(c2O)C(=O)C2=C(O)[C@]4(O)C(=O)C(C(N)=O)=C(O)[C@@H](N(C)C)[C@@H]4C[C@@H]2C3)cc1] |
| 27 | 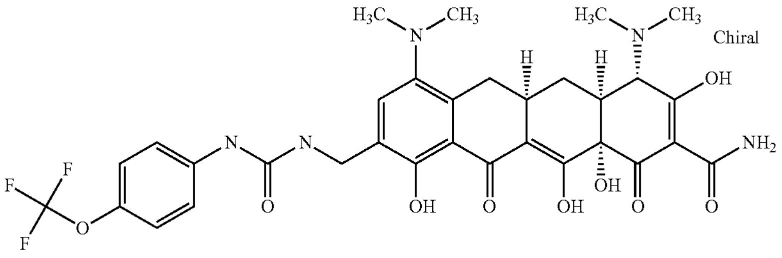 [SMILES: CN(C)c1cc(CNC(=O)Nc2ccc(OC(F)(F)F)cc2)c(O)c2c1C[C@H]1C[C@H]3[C@H](N(C)C)C(O)=C(C(N)=O)C(=O)[C@@]3(O)C(O)=C1C2=O] |
| 28 | 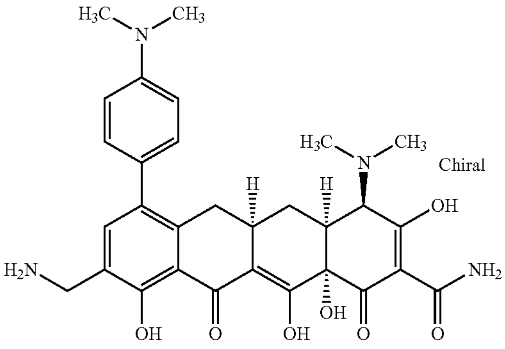 [SMILES: CN(C)c1ccc(-c2cc(CN)c(O)c3c2C[C@H]2C[C@H]4[C@@H](N(C)C)C(O)=C(C(N)=O)C(=O)[C@@]4(O)C(O)=C2C3=O)cc1] |
| 29 | 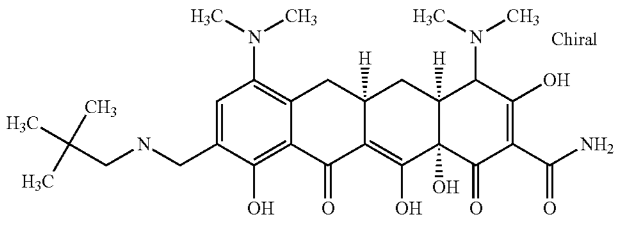 [SMILES: CN(C)c1cc(CNCC(C)(C)C)c(O)c2c1C[C@H]1C[C@H]3C(N(C)C)C(O)=C(C(N)=O)C(=O)[C@@]3(O)C(O)=C1C2=O] |
| 30 | 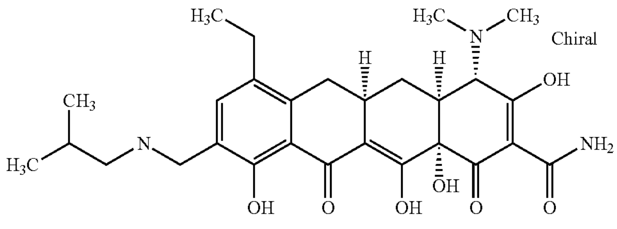 [SMILES: CCc1cc(CNCC(C)C)c(O)c2c1C[C@H]1C[C@H]3[C@H](N(C)C)C(O)=C(C(N)=O)C(=O)[C@@]3(O)C(O)=C1C2=O] |

TABLE 1-continued
| Tetracycline Compounds | |
|---|---|
| Compound number | Structure |
| 31 | 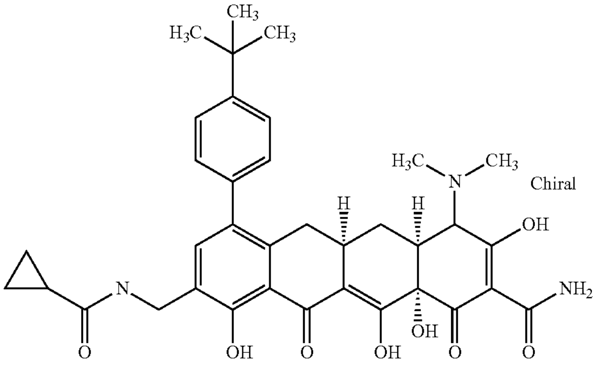 [SMILES: CN(C)C1C(O)=C(C(N)=O)C(=O)[C@@]2(O)C(O)=C3C(=O)c4c(O)c(CNC(=O)C5CC5)cc(-c5ccc(C(C)(C)C)cc5)c4C[C@H]3C[C@@H]12] |
| 32 | 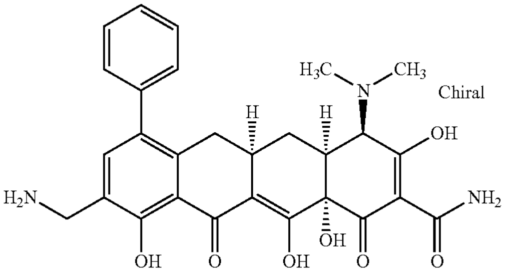 [SMILES: CN(C)[C@H]1C(O)=C(C(N)=O)C(=O)[C@@]2(O)C(O)=C3C(=O)c4c(O)c(CN)cc(-c5ccccc5)c4C[C@H]3C[C@@H]12] |
| 33 | 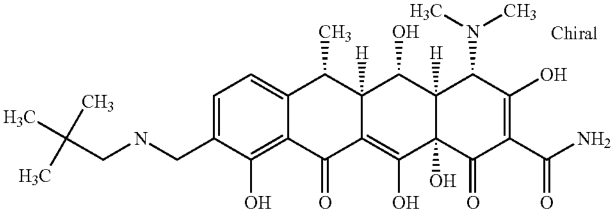 [SMILES: C[C@H]1c2ccc(CNCC(C)(C)C)c(O)c2C(=O)C2=C(O)[C@]3(O)C(=O)C(C(N)=O)=C(O)[C@@H](N(C)C)[C@@H]3[C@@H](O)[C@@H]21] |
| 34 | 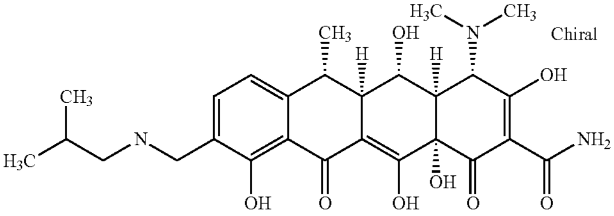 [SMILES: CC(C)CNCc1ccc2c(c1O)C(=O)C1=C(O)[C@]3(O)C(=O)C(C(N)=O)=C(O)[C@@H](N(C)C)[C@@H]3[C@@H](O)[C@@H]1[C@H]2C] |
| 35 | 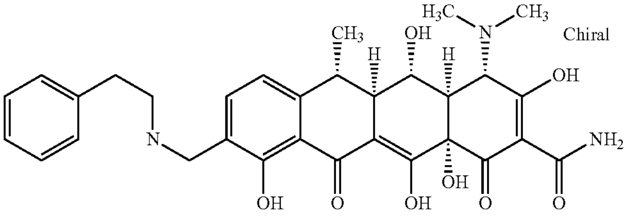 [SMILES: C[C@H]1c2ccc(CNCCc3ccccc3)c(O)c2C(=O)C2=C(O)[C@]3(O)C(=O)C(C(N)=O)=C(O)[C@@H](N(C)C)[C@@H]3[C@@H](O)[C@@H]21] |
| 36 | 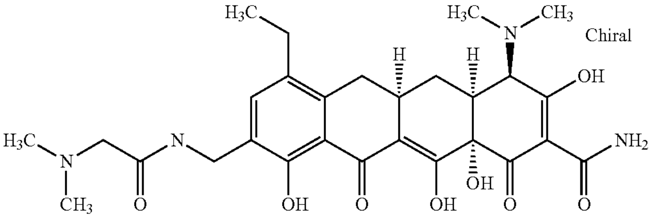 [SMILES: CCc1cc(CNC(=O)CN(C)C)c(O)c2c1C[C@H]1C[C@H]3[C@@H](N(C)C)C(O)=C(C(N)=O)C(=O)[C@@]3(O)C(O)=C1C2=O] |

TABLE 1-continued
Tetracycline Compounds
| Compound number | Structure |
| --- | --- |
| 37 | 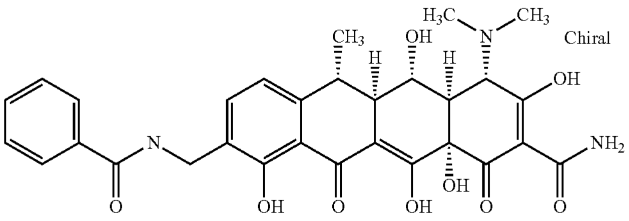 [SMILES: C[C@H]1c2ccc(CNC(=O)c3ccccc3)c(O)c2C(=O)C2=C(O)[C@]3(O)C(=O)C(C(N)=O)=C(O)[C@@H](N(C)C)[C@@H]3[C@@H](O)[C@@H]21] |
| 38 | 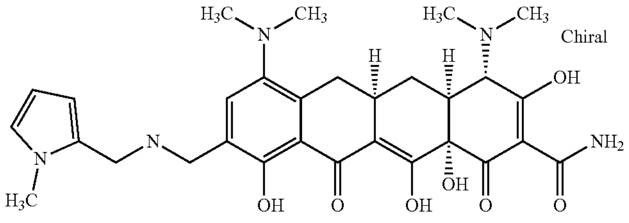 [SMILES: CN(C)c1cc(CNCc2cccn2C)c(O)c2c1C[C@H]1C[C@H]3[C@H](N(C)C)C(O)=C(C(N)=O)C(=O)[C@@]3(O)C(O)=C1C2=O] |
| 39 | 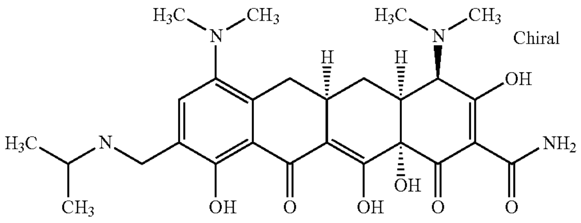 [SMILES: CC(C)NCc1cc(N(C)C)c2c(c1O)C(=O)C1=C(O)[C@]3(O)C(=O)C(C(N)=O)=C(O)[C@H](N(C)C)[C@@H]3C[C@@H]1C2] |
| 40 | 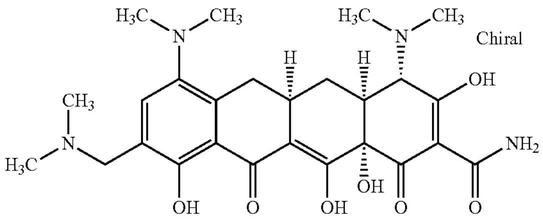 [SMILES: CN(C)Cc1cc(N(C)C)c2c(c1O)C(=O)C1=C(O)[C@]3(O)C(=O)C(C(N)=O)=C(O)[C@@H](N(C)C)[C@@H]3C[C@@H]1C2] |
| 41 | 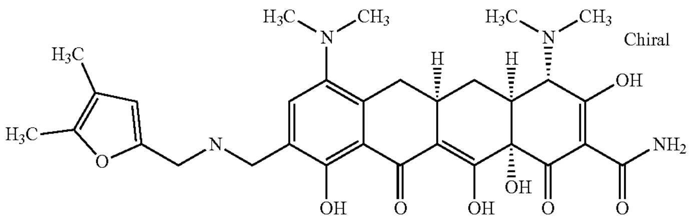 [SMILES: Cc1cc(CNCc2cc(N(C)C)c3c(c2O)C(=O)C2=C(O)[C@]4(O)C(=O)C(C(N)=O)=C(O)[C@@H](N(C)C)[C@@H]4C[C@@H]2C3)oc1C] |
| 42 | 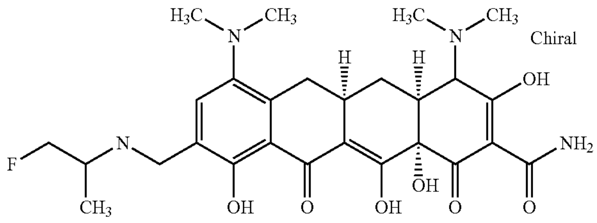 [SMILES: CC(CF)NCc1cc(N(C)C)c2c(c1O)C(=O)C1=C(O)[C@]3(O)C(=O)C(C(N)=O)=C(O)C(N(C)C)[C@@H]3C[C@@H]1C2] |

TABLE 1-continued
| Tetracycline Compounds | |
|---|---|
| Compound number | Structure |
| 43 | 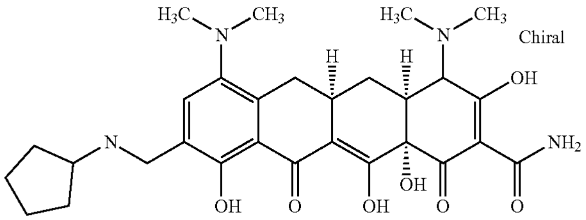 [SMILES: CN(C)c1cc(CNC2CCCC2)c(O)c2c1C[C@H]1C[C@H]3C(N(C)C)C(O)=C(C(N)=O)C(=O)[C@@]3(O)C(O)=C1C2=O] |
| 44 | 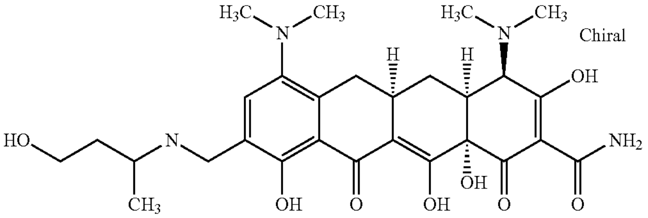 [SMILES: CC(CCO)NCc1cc(N(C)C)c2c(c1O)C(=O)C1=C(O)[C@]3(O)C(=O)C(C(N)=O)=C(O)[C@H](N(C)C)[C@@H]3C[C@@H]1C2] |
| 45 | 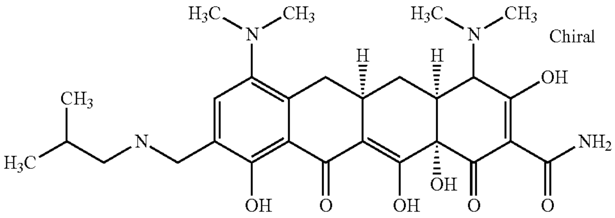 [SMILES: CC(C)CNCc1cc(N(C)C)c2c(c1O)C(=O)C1=C(O)[C@]3(O)C(=O)C(C(N)=O)=C(O)C(N(C)C)[C@@H]3C[C@@H]1C2] |
| 46 | 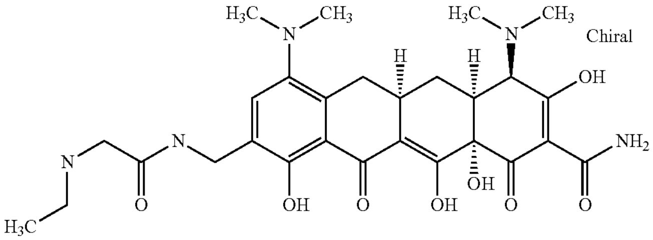 [SMILES: CCNCC(=O)NCc1cc(N(C)C)c2c(c1O)C(=O)C1=C(O)[C@]3(O)C(=O)C(C(N)=O)=C(O)[C@H](N(C)C)[C@@H]3C[C@@H]1C2] |
| 47 | 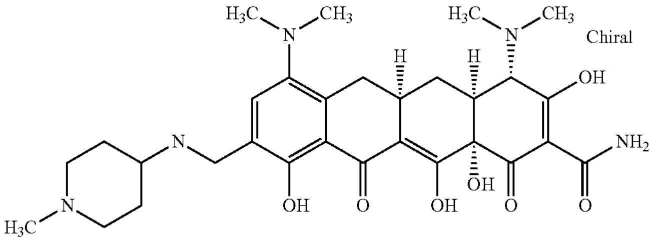 [SMILES: CN1CCC(NCc2cc(N(C)C)c3c(c2O)C(=O)C2=C(O)[C@]4(O)C(=O)C(C(N)=O)=C(O)[C@@H](N(C)C)[C@@H]4C[C@@H]2C3)CC1] |
| 48 | 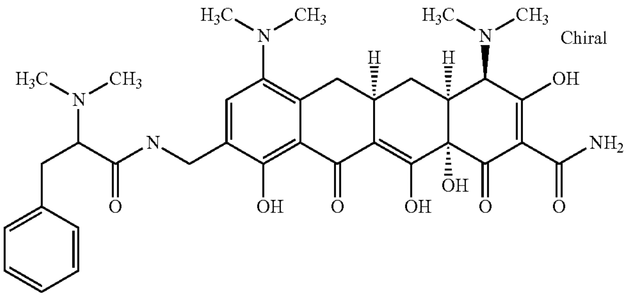 [SMILES: CN(C)c1cc(CNC(=O)C(Cc2ccccc2)N(C)C)c(O)c2c1C[C@H]1C[C@H]3[C@@H](N(C)C)C(O)=C(C(N)=O)C(=O)[C@@]3(O)C(O)=C1C2=O] |

TABLE 1-continued
| Tetracycline Compounds | |
|---|---|
| Compound number | Structure |
| 49 | 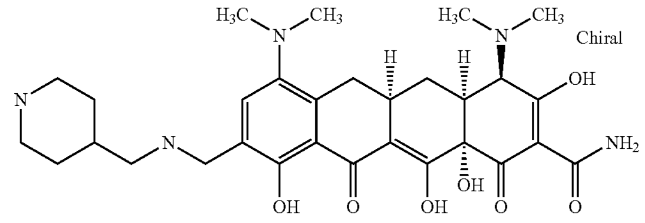 [SMILES: CN(C)c1cc(CNCC2CCNCC2)c(O)c2c1C[C@H]1C[C@H]3[C@@H](N(C)C)C(O)=C(C(N)=O)C(=O)[C@@]3(O)C(O)=C1C2=O] |
| 50 | 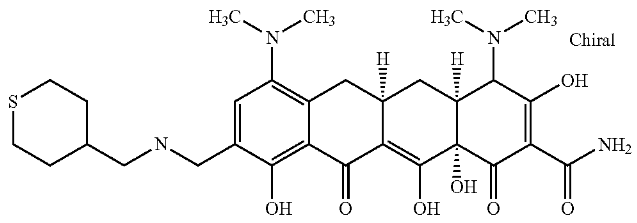 [SMILES: CN(C)c1cc(CNCC2CCSCC2)c(O)c2c1C[C@H]1C[C@H]3C(N(C)C)C(O)=C(C(N)=O)C(=O)[C@@]3(O)C(O)=C1C2=O] |
| 51 | 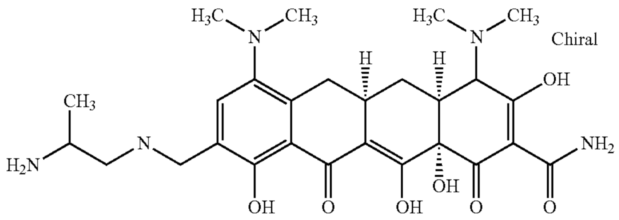 |
| 52 | 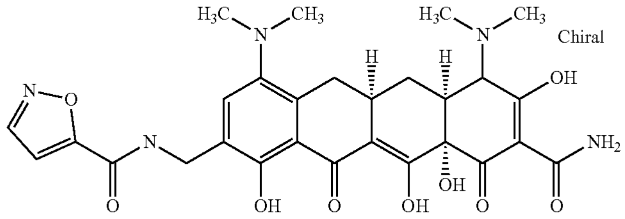 [SMILES: CN(C)c1cc(CNC(=O)c2ccno2)c(O)c2c1C[C@H]1C[C@H]3C(N(C)C)C(O)=C(C(N)=O)C(=O)[C@@]3(O)C(O)=C1C2=O] |
| 53 | 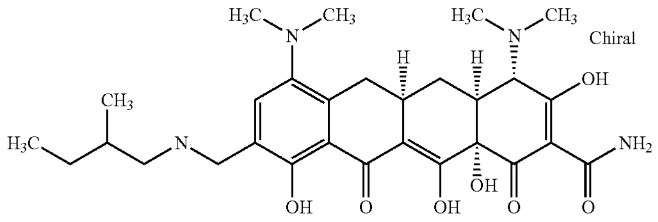 [SMILES: CCC(C)CNCc1cc(N(C)C)c2c(c1O)C(=O)C1=C(O)[C@]3(O)C(=O)C(C(N)=O)=C(O)[C@@H](N(C)C)[C@@H]3C[C@@H]1C2] |
| 54 | 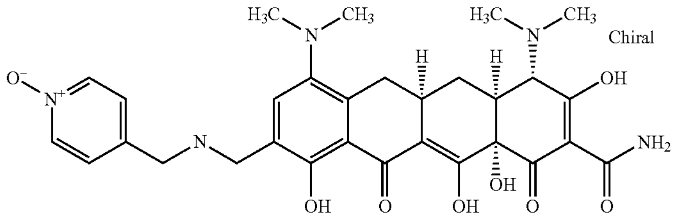 [SMILES: CN(C)c1cc(CNCc2cc[n+]([O-])cc2)c(O)c2c1C[C@H]1C[C@H]3[C@H](N(C)C)C(O)=C(C(N)=O)C(=O)[C@@]3(O)C(O)=C1C2=O] |

TABLE 1-continued
| Tetracycline Compounds | |
|---|---|
| Compound number | Structure |
| 55 | 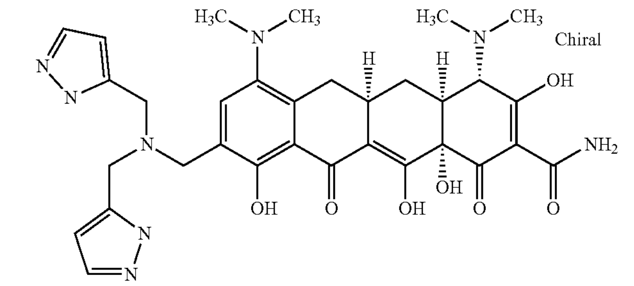 [SMILES: CN(C)c1cc(CN(Cc2ccn[nH]2)Cc2ccn[nH]2)c(O)c2c1C[C@H]1C[C@H]3[C@H](N(C)C)C(O)=C(C(N)=O)C(=O)[C@@]3(O)C(O)=C1C2=O] |
| 56 | 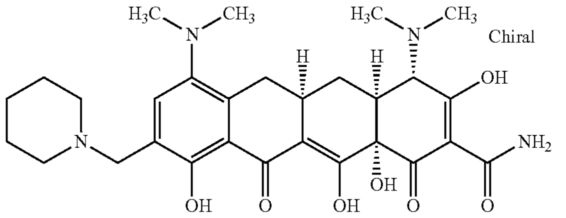 [SMILES: CN(C)c1cc(CN2CCCCC2)c(O)c2c1C[C@H]1C[C@H]3[C@H](N(C)C)C(O)=C(C(N)=O)C(=O)[C@@]3(O)C(O)=C1C2=O] |
| 57 | 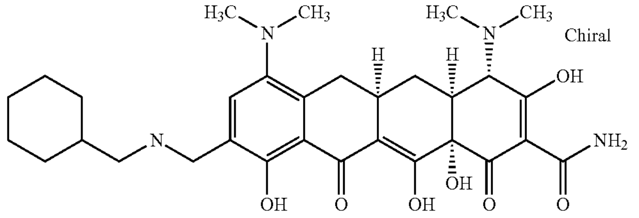 [SMILES: CN(C)c1cc(CNCC2CCCCC2)c(O)c2c1C[C@H]1C[C@H]3[C@H](N(C)C)C(O)=C(C(N)=O)C(=O)[C@@]3(O)C(O)=C1C2=O] |
| 58 | 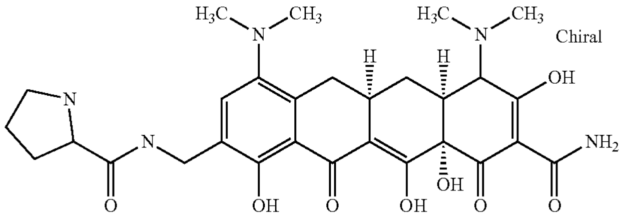 [SMILES: CN(C)c1cc(CNC(=O)C2CCCN2)c(O)c2c1C[C@H]1C[C@H]3C(N(C)C)C(O)=C(C(N)=O)C(=O)[C@@]3(O)C(O)=C1C2=O] |
| 59 | 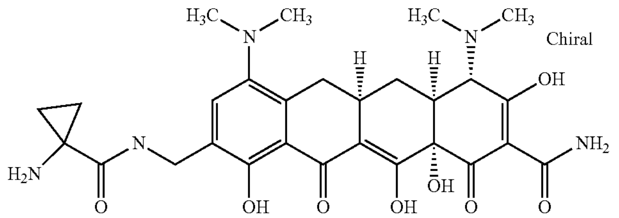 [SMILES: CN(C)c1cc(CNC(=O)C2(N)CC2)c(O)c2c1C[C@H]1C[C@H]3[C@H](N(C)C)C(O)=C(C(N)=O)C(=O)[C@@]3(O)C(O)=C1C2=O] |
| 60 | 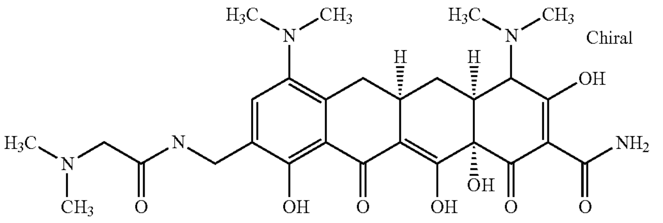 [SMILES: CN(C)CC(=O)NCc1cc(N(C)C)c2c(c1O)C(=O)C1=C(O)[C@]3(O)C(=O)C(C(N)=O)=C(O)C(N(C)C)[C@@H]3C[C@@H]1C2] |

TABLE 1-continued
| Tetracycline Compounds | |
|---|---|
| Compound number | Structure |
| 61 | 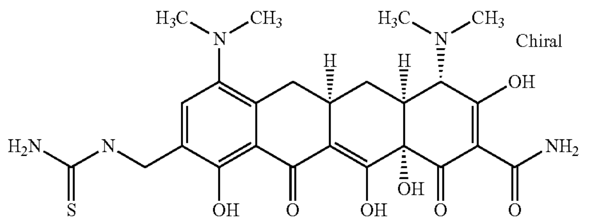 [SMILES: CN(C)c1cc(CNC(N)=S)c(O)c2c1C[C@H]1C[C@H]3[C@H](N(C)C)C(O)=C(C(N)=O)C(=O)[C@@]3(O)C(O)=C1C2=O] |
| 62 | 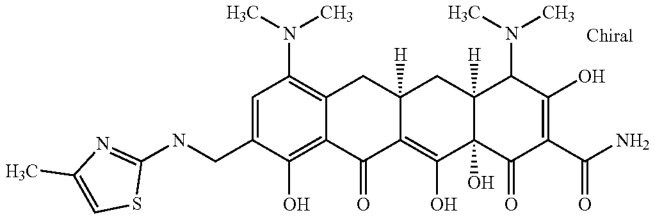 [SMILES: Cc1csc(NCc2cc(N(C)C)c3c(c2O)C(=O)C2=C(O)[C@]4(O)C(=O)C(C(N)=O)=C(O)C(N(C)C)[C@@H]4C[C@@H]2C3)n1] |
| 63 | 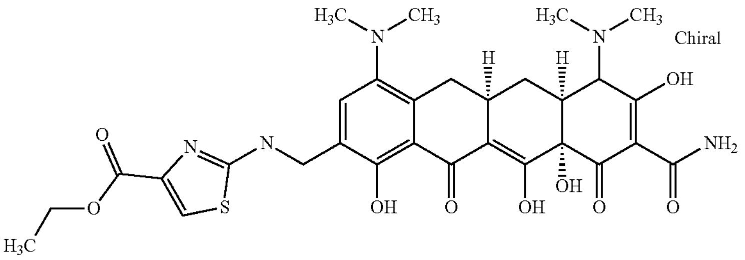 [SMILES: CCOC(=O)c1csc(NCc2cc(N(C)C)c3c(c2O)C(=O)C2=C(O)[C@]4(O)C(=O)C(C(N)=O)=C(O)C(N(C)C)[C@@H]4C[C@@H]2C3)n1] |
| 64 | 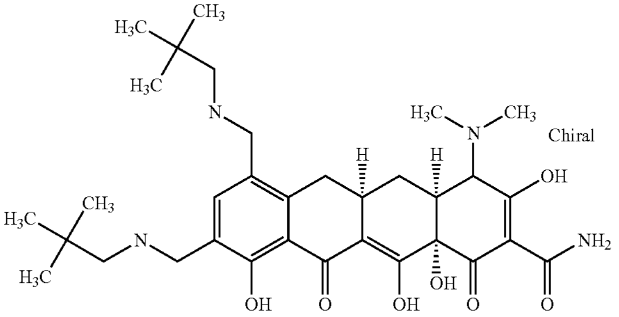 [SMILES: CN(C)C1C(O)=C(C(N)=O)C(=O)[C@@]2(O)C(O)=C3C(=O)c4c(O)c(CNCC(C)(C)C)cc(CNCC(C)(C)C)c4C[C@H]3C[C@@H]12] |
| 65 | 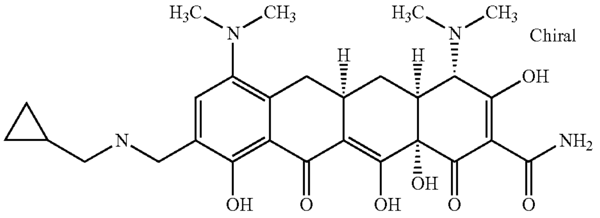 [SMILES: CN(C)c1cc(CNCC2CC2)c(O)c2c1C[C@H]1C[C@H]3[C@H](N(C)C)C(O)=C(C(N)=O)C(=O)[C@@]3(O)C(O)=C1C2=O] |
| 66 | 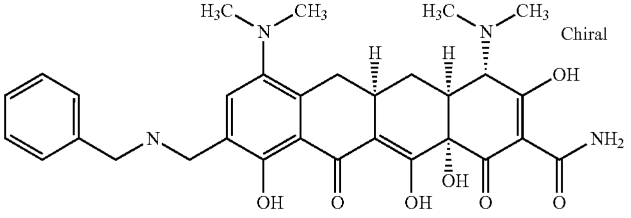 [SMILES: CN(C)c1cc(CNCc2ccccc2)c(O)c2c1C[C@H]1C[C@H]3[C@H](N(C)C)C(O)=C(C(N)=O)C(=O)[C@@]3(O)C(O)=C1C2=O] |

TABLE 1-continued
| Tetracycline Compounds | |
|---|---|
| Compound number | Structure |
| 67 | 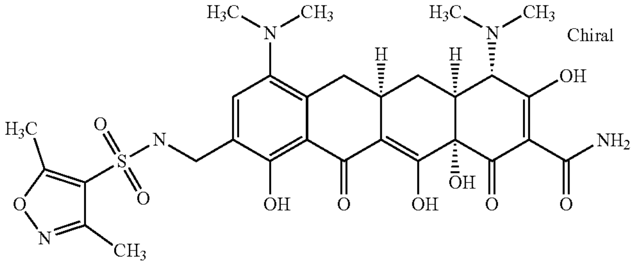 [SMILES: Cc1noc(C)c1S(=O)(=O)NCc1cc(N(C)C)c2c(c1O)C(=O)C1=C(O)[C@]3(O)C(=O)C(C(N)=O)=C(O)[C@@H](N(C)C)[C@@H]3C[C@@H]1C2] |
| 68 | 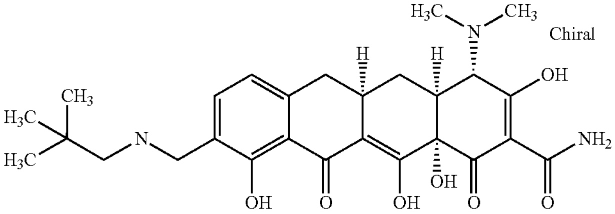 [SMILES: CN(C)[C@@H]1C(O)=C(C(N)=O)C(=O)[C@@]2(O)C(O)=C3C(=O)c4c(ccc(CNCC(C)(C)C)c4O)C[C@H]3C[C@@H]12] |
| 69 | 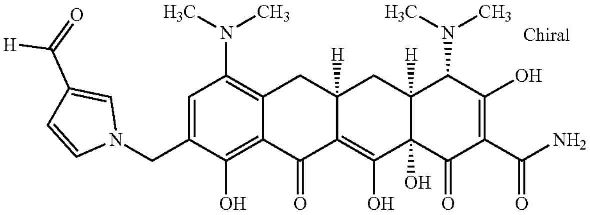 [SMILES: CN(C)c1cc(Cn2ccc(C=O)c2)c(O)c2c1C[C@H]1C[C@H]3[C@H](N(C)C)C(O)=C(C(N)=O)C(=O)[C@@]3(O)C(O)=C1C2=O] |
| 70 | 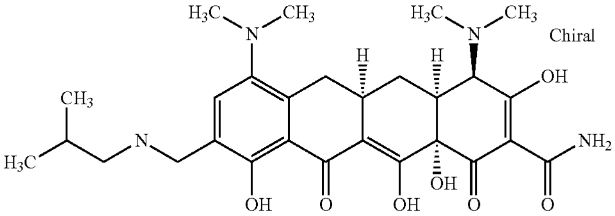 [SMILES: CC(C)CNCc1cc(N(C)C)c2c(c1O)C(=O)C1=C(O)[C@]3(O)C(=O)C(C(N)=O)=C(O)[C@H](N(C)C)[C@@H]3C[C@@H]1C2] |
| 71 | 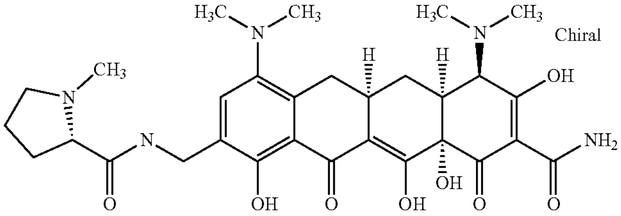 [SMILES: CN(C)c1cc(CNC(=O)[C@@H]2CCCN2C)c(O)c2c1C[C@H]1C[C@H]3[C@@H](N(C)C)C(O)=C(C(N)=O)C(=O)[C@@]3(O)C(O)=C1C2=O] |
| 72 | 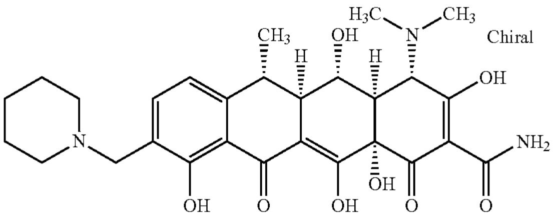 [SMILES: C[C@H]1c2ccc(CN3CCCCC3)c(O)c2C(=O)C2=C(O)[C@]3(O)C(=O)C(C(N)=O)=C(O)[C@@H](N(C)C)[C@@H]3[C@@H](O)[C@@H]21] |

TABLE 1-continued
| Tetracycline Compounds | |
|---|---|
| Compound number | Structure |
| 73 | 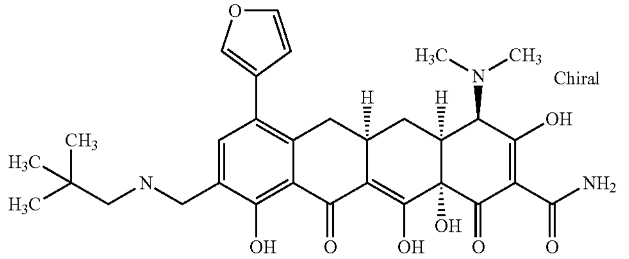 [SMILES: CN(C)[C@H]1C(O)=C(C(N)=O)C(=O)[C@@]2(O)C(O)=C3C(=O)c4c(O)c(CNCC(C)(C)C)cc(-c5ccoc5)c4C[C@H]3C[C@@H]12] |
| 74 | 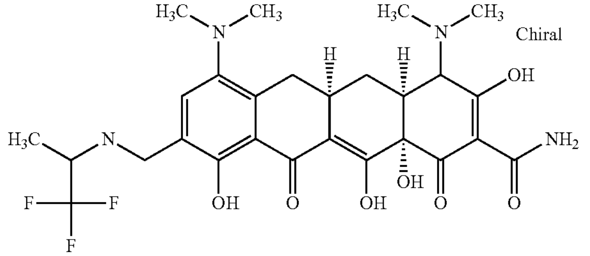 [SMILES: CC(NCc1cc(N(C)C)c2c(c1O)C(=O)C1=C(O)[C@]3(O)C(=O)C(C(N)=O)=C(O)C(N(C)C)[C@@H]3C[C@@H]1C2)C(F)(F)F] |
| 75 | 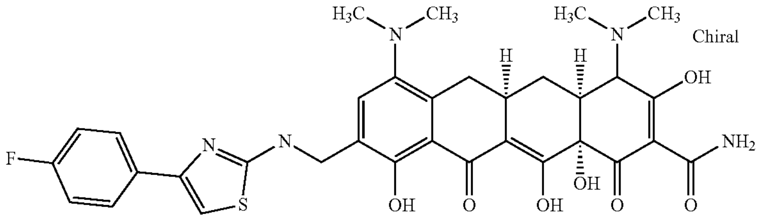 [SMILES: CN(C)c1cc(CNc2nc(-c3ccc(F)cc3)cs2)c(O)c2c1C[C@H]1C[C@H]3C(N(C)C)C(O)=C(C(N)=O)C(=O)[C@@]3(O)C(O)=C1C2=O] |
| 76 | 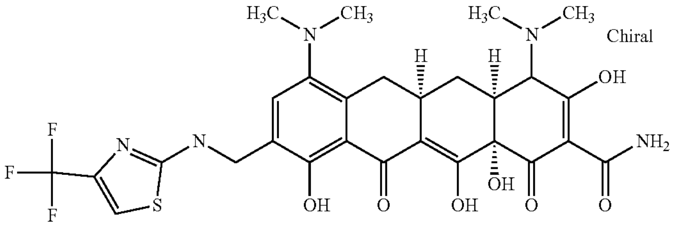 [SMILES: CN(C)c1cc(CNc2nc(C(F)(F)F)cs2)c(O)c2c1C[C@H]1C[C@H]3C(N(C)C)C(O)=C(C(N)=O)C(=O)[C@@]3(O)C(O)=C1C2=O] |
| 77 | 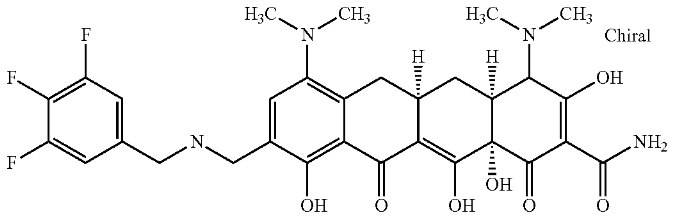 [SMILES: CN(C)c1cc(CNCc2cc(F)c(F)c(F)c2)c(O)c2c1C[C@H]1C[C@H]3C(N(C)C)C(O)=C(C(N)=O)C(=O)[C@@]3(O)C(O)=C1C2=O] |
| 78 | 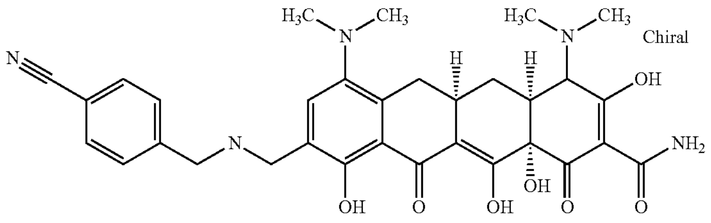 [SMILES: CN(C)c1cc(CNCc2ccc(C#N)cc2)c(O)c2c1C[C@H]1C[C@H]3C(N(C)C)C(O)=C(C(N)=O)C(=O)[C@@]3(O)C(O)=C1C2=O] |

TABLE 1-continued
Tetracycline Compounds
| Compound number | Structure |
|---|---|
| 79 | 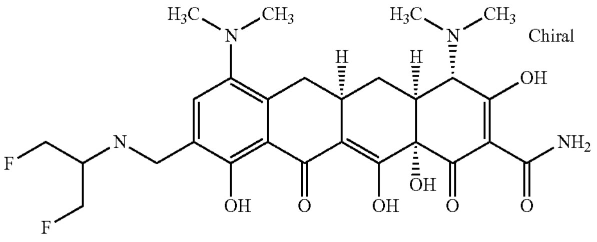 [SMILES: CN(C)c1cc(CNC(CF)CF)c(O)c2c1C[C@H]1C[C@H]3[C@H](N(C)C)C(O)=C(C(N)=O)C(=O)[C@@]3(O)C(O)=C1C2=O] |
| 80 | 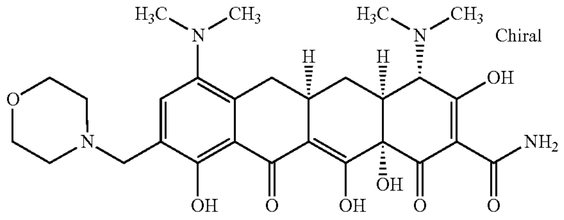 [SMILES: CN(C)c1cc(CN2CCOCC2)c(O)c2c1C[C@H]1C[C@H]3[C@H](N(C)C)C(O)=C(C(N)=O)C(=O)[C@@]3(O)C(O)=C1C2=O] |
| 81 | 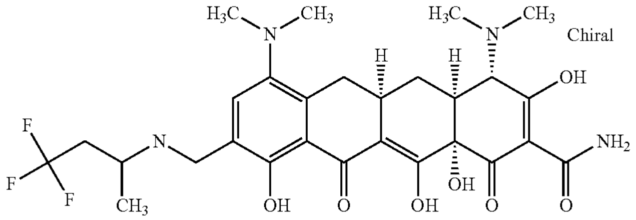 [SMILES: CC(CC(F)(F)F)NCc1cc(N(C)C)c2c(c1O)C(=O)C1=C(O)[C@]3(O)C(=O)C(C(N)=O)=C(O)[C@@H](N(C)C)[C@@H]3C[C@@H]1C2] |
| 82 | 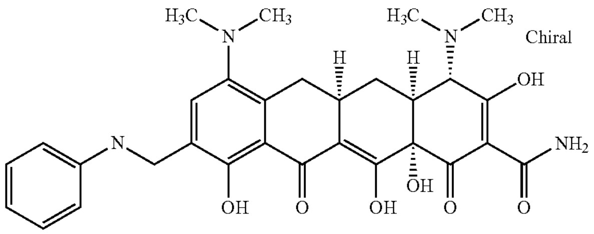 [SMILES: CN(C)c1cc(CNc2ccccc2)c(O)c2c1C[C@H]1C[C@H]3[C@H](N(C)C)C(O)=C(C(N)=O)C(=O)[C@@]3(O)C(O)=C1C2=O] |
| 83 | 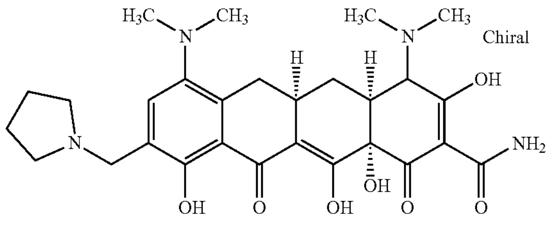 [SMILES: CN(C)c1cc(CN2CCCC2)c(O)c2c1C[C@H]1C[C@H]3C(N(C)C)C(O)=C(C(N)=O)C(=O)[C@@]3(O)C(O)=C1C2=O] |
| 84 | 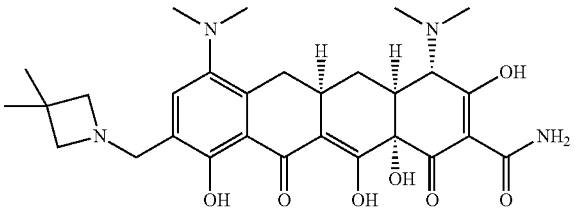 [SMILES: CN(C)c1cc(CN2CC(C)(C)C2)c(O)c2c1C[C@H]1C[C@H]3[C@H](N(C)C)C(O)=C(C(N)=O)C(=O)[C@@]3(O)C(O)=C1C2=O] |

TABLE 1-continued
| Tetracycline Compounds | |
|---|---|
| Compound number | Structure |
| 85 | 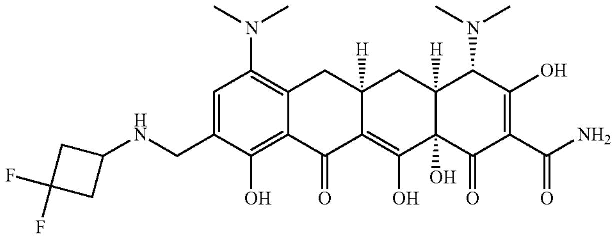 [SMILES: CN(C)c1cc(CNC2CC(F)(F)C2)c(O)c2c1C[C@H]1C[C@H]3[C@H](N(C)C)C(O)=C(C(N)=O)C(=O)[C@@]3(O)C(O)=C1C2=O] |
| 86 | 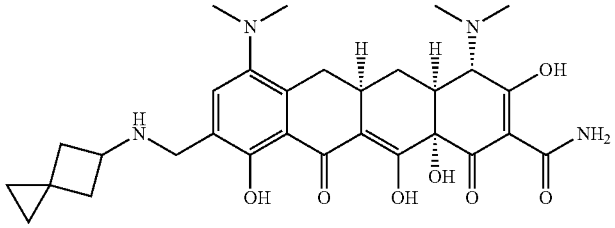 [SMILES: CN(C)c1cc(CNC2CC3(CC3)C2)c(O)c2c1C[C@H]1C[C@H]3[C@H](N(C)C)C(O)=C(C(N)=O)C(=O)[C@@]3(O)C(O)=C1C2=O] |
| 87 | 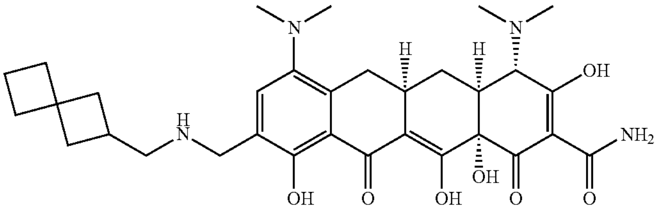 [SMILES: CN(C)c1cc(CNCC2CC3(CCC3)C2)c(O)c2c1C[C@H]1C[C@H]3[C@H](N(C)C)C(O)=C(C(N)=O)C(=O)[C@@]3(O)C(O)=C1C2=O] |
| 88 | 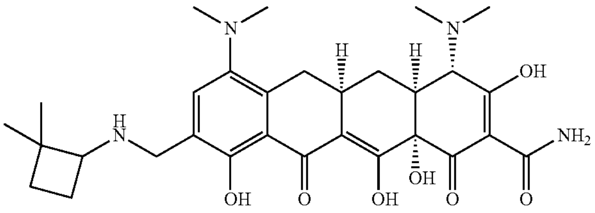 [SMILES: CN(C)c1cc(CNC2CCC2(C)C)c(O)c2c1C[C@H]1C[C@H]3[C@H](N(C)C)C(O)=C(C(N)=O)C(=O)[C@@]3(O)C(O)=C1C2=O] |
| 89 | 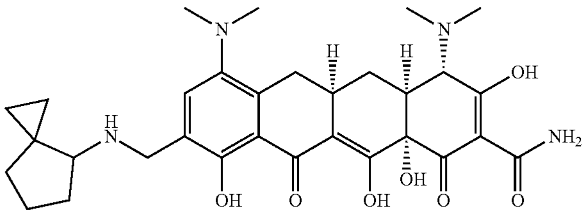 [SMILES: CN(C)c1cc(CNC2CCCC23CC3)c(O)c2c1C[C@H]1C[C@H]3[C@H](N(C)C)C(O)=C(C(N)=O)C(=O)[C@@]3(O)C(O)=C1C2=O] |
| 90 | 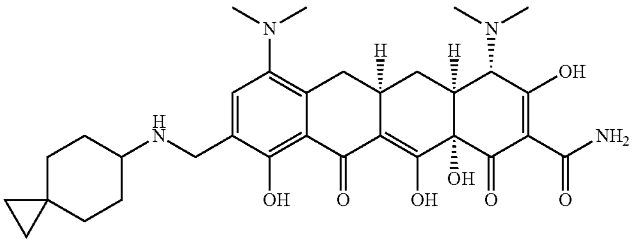 [SMILES: CN(C)c1cc(CNC2CCC3(CC2)CC3)c(O)c2c1C[C@H]1C[C@H]3[C@H](N(C)C)C(O)=C(C(N)=O)C(=O)[C@@]3(O)C(O)=C1C2=O] |

TABLE 1-continued
| Tetracycline Compounds | |
|---|---|
| Compound number | Structure |
| 91 | 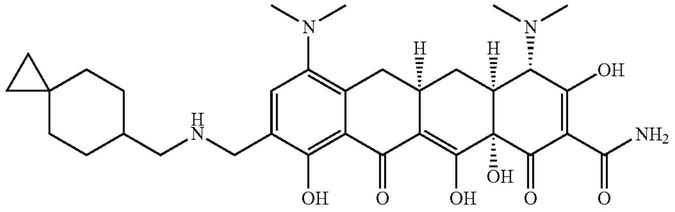 [SMILES: CN(C)c1cc(CNCC2CCC3(CC2)CC3)c(O)c2c1C[C@H]1C[C@H]3[C@H](N(C)C)C(O)=C(C(N)=O)C(=O)[C@@]3(O)C(O)=C1C2=O] |
| 92 | 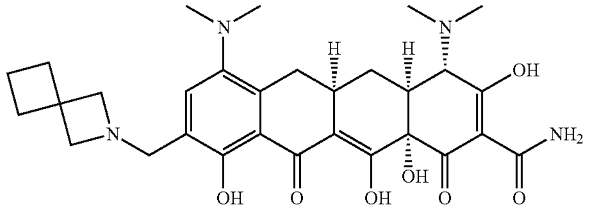 [SMILES: CN(C)c1cc(CN2CC3(CCC3)C2)c(O)c2c1C[C@H]1C[C@H]3[C@H](N(C)C)C(O)=C(C(N)=O)C(=O)[C@@]3(O)C(O)=C1C2=O] |
| 93 | 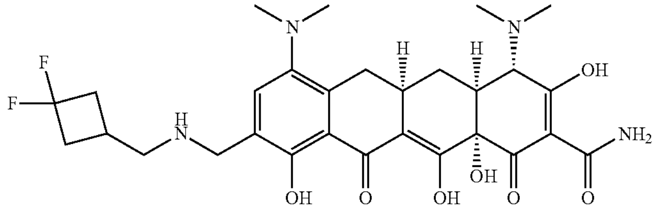 [SMILES: CN(C)c1cc(CNCC2CC(F)(F)C2)c(O)c2c1C[C@H]1C[C@H]3[C@H](N(C)C)C(O)=C(C(N)=O)C(=O)[C@@]3(O)C(O)=C1C2=O] |
| 94 | 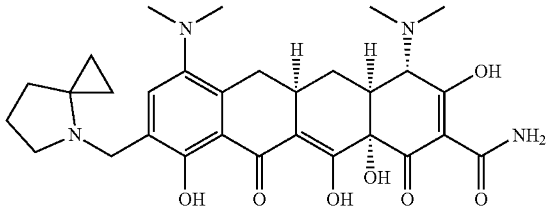 [SMILES: CN(C)c1cc(CN2CCCC23CC3)c(O)c2c1C[C@H]1C[C@H]3[C@H](N(C)C)C(O)=C(C(N)=O)C(=O)[C@@]3(O)C(O)=C1C2=O] |
| 95 | 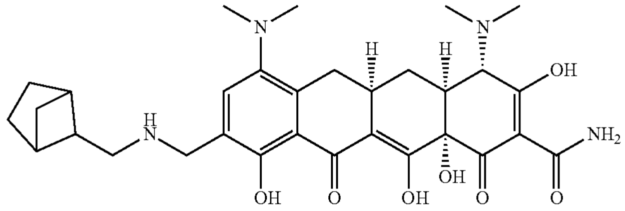 [SMILES: CN(C)c1cc(CNCC2C3CCC2C3)c(O)c2c1C[C@H]1C[C@H]3[C@H](N(C)C)C(O)=C(C(N)=O)C(=O)[C@@]3(O)C(O)=C1C2=O] |
| 96 | 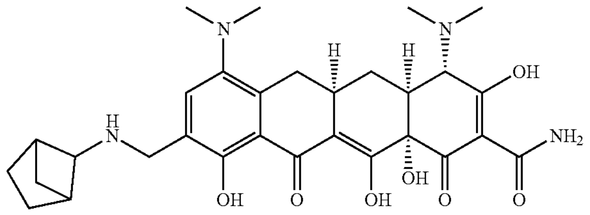 [SMILES: CN(C)c1cc(CNC2C3CCC2C3)c(O)c2c1C[C@H]1C[C@H]3[C@H](N(C)C)C(O)=C(C(N)=O)C(=O)[C@@]3(O)C(O)=C1C2=O] |
| 97 | 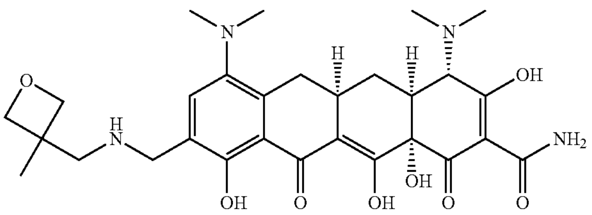 [SMILES: CN(C)c1cc(CNCC2(C)COC2)c(O)c2c1C[C@H]1C[C@H]3[C@H](N(C)C)C(O)=C(C(N)=O)C(=O)[C@@]3(O)C(O)=C1C2=O] |

TABLE 1-continued
Tetracycline Compounds
| Compound number | Structure |
| --- | --- |
| 98 | 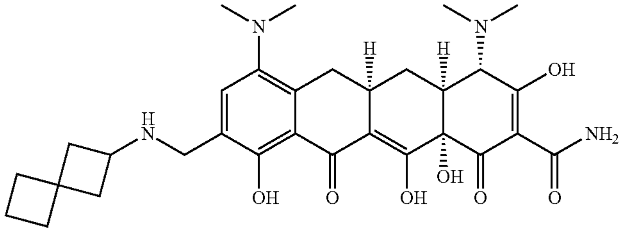 [SMILES: CN(C)c1cc(CNC2CC3(CCC3)C2)c(O)c2c1C[C@H]1C[C@H]3[C@H](N(C)C)C(O)=C(C(N)=O)C(=O)[C@@]3(O)C(O)=C1C2=O] |
| 99 | 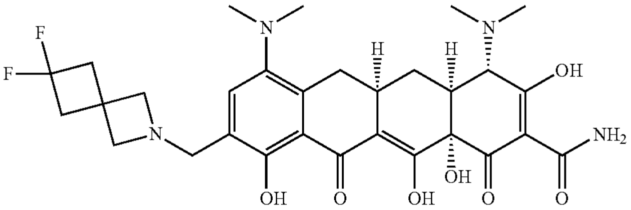 [SMILES: CN(C)c1cc(CN2CC3(C2)CC(F)(F)C3)c(O)c2c1C[C@H]1C[C@H]3[C@H](N(C)C)C(O)=C(C(N)=O)C(=O)[C@@]3(O)C(O)=C1C2=O] |
| 100 | 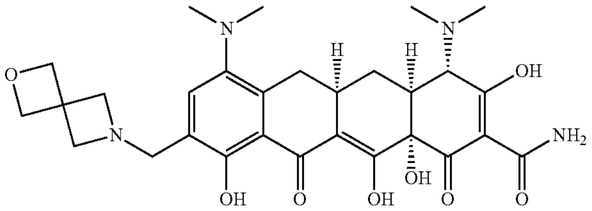 [SMILES: CN(C)c1cc(CN2CC3(COC3)C2)c(O)c2c1C[C@H]1C[C@H]3[C@H](N(C)C)C(O)=C(C(N)=O)C(=O)[C@@]3(O)C(O)=C1C2=O] |
| 101 | 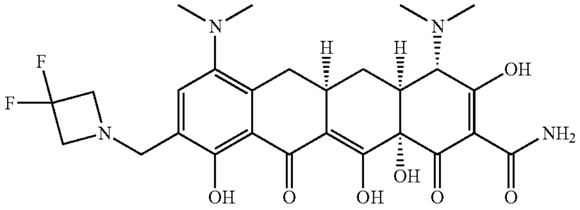 [SMILES: CN(C)c1cc(CN2CC(F)(F)C2)c(O)c2c1C[C@H]1C[C@H]3[C@H](N(C)C)C(O)=C(C(N)=O)C(=O)[C@@]3(O)C(O)=C1C2=O] |
| 102 | 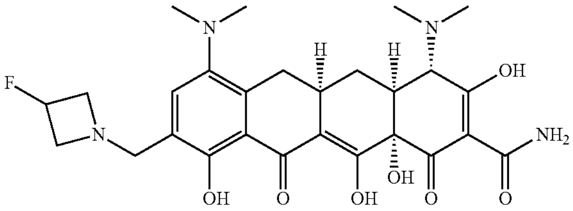 [SMILES: CN(C)c1cc(CN2CC(F)C2)c(O)c2c1C[C@H]1C[C@H]3[C@H](N(C)C)C(O)=C(C(N)=O)C(=O)[C@@]3(O)C(O)=C1C2=O] |
| 103 | 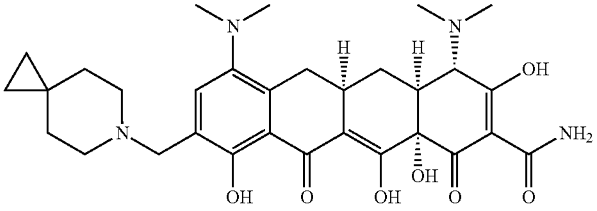 [SMILES: CN(C)c1cc(CN2CCC3(CC2)CC3)c(O)c2c1C[C@H]1C[C@H]3[C@H](N(C)C)C(O)=C(C(N)=O)C(=O)[C@@]3(O)C(O)=C1C2=O] |
| 104 | 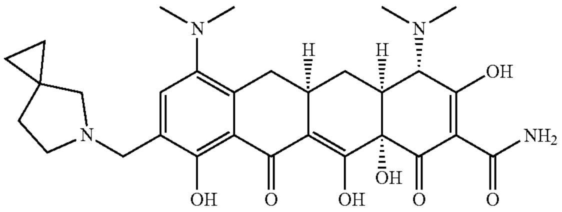 [SMILES: CN(C)c1cc(CN2CCC3(CC3)C2)c(O)c2c1C[C@H]1C[C@H]3[C@H](N(C)C)C(O)=C(C(N)=O)C(=O)[C@@]3(O)C(O)=C1C2=O] |

TABLE 1-continued
| Tetracycline Compounds | |
|---|---|
| Compound number | Structure |
| 105 | 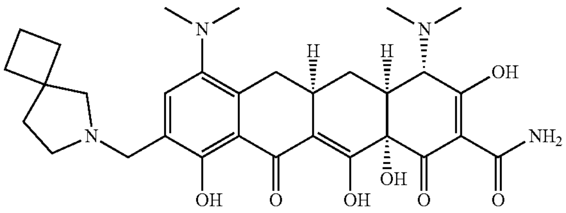 [SMILES: CN(C)c1cc(CN2CCC3(CCC3)C2)c(O)c2c1C[C@H]1C[C@H]3[C@H](N(C)C)C(O)=C(C(N)=O)C(=O)[C@@]3(O)C(O)=C1C2=O] |
| 106 | 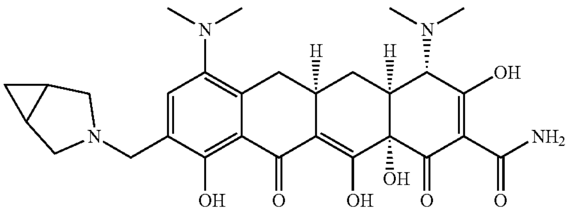 [SMILES: CN(C)c1cc(CN2CC3CC3C2)c(O)c2c1C[C@H]1C[C@H]3[C@H](N(C)C)C(O)=C(C(N)=O)C(=O)[C@@]3(O)C(O)=C1C2=O] |
| 107 | 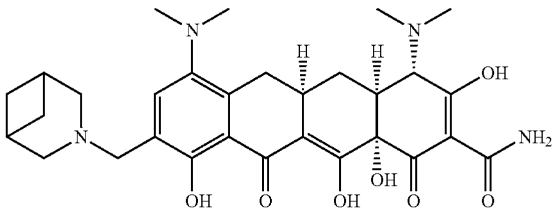 [SMILES: CN(C)c1cc(CN2CC3CC(C3)C2)c(O)c2c1C[C@H]1C[C@H]3[C@H](N(C)C)C(O)=C(C(N)=O)C(=O)[C@@]3(O)C(O)=C1C2=O] |
| 108 | 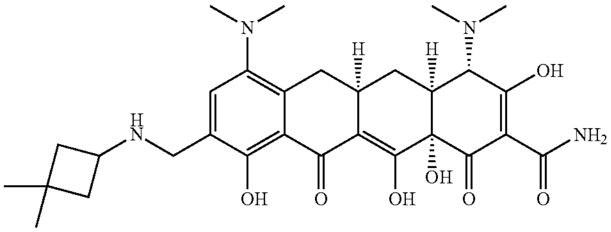 [SMILES: CN(C)c1cc(CNC2CC(C)(C)C2)c(O)c2c1C[C@H]1C[C@H]3[C@H](N(C)C)C(O)=C(C(N)=O)C(=O)[C@@]3(O)C(O)=C1C2=O] |
| 109 | 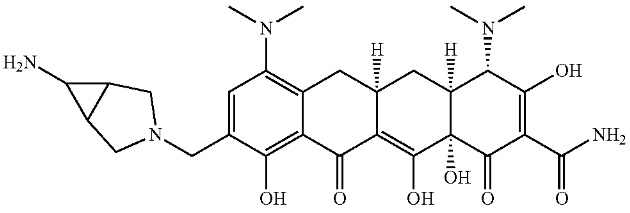 [SMILES: CN(C)c1cc(CN2CC3C(N)C3C2)c(O)c2c1C[C@H]1C[C@H]3[C@H](N(C)C)C(O)=C(C(N)=O)C(=O)[C@@]3(O)C(O)=C1C2=O] |
| 110 | 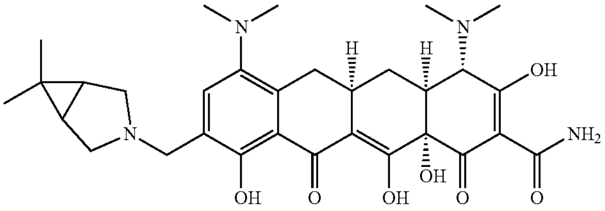 [SMILES: CN(C)c1cc(CN2CC3C(C2)C3(C)C)c(O)c2c1C[C@H]1C[C@H]3[C@H](N(C)C)C(O)=C(C(N)=O)C(=O)[C@@]3(O)C(O)=C1C2=O] |

TABLE 1-continued

| Tetracycline Compounds | |
|---|---|
| Compound number | Structure |
| 111 | 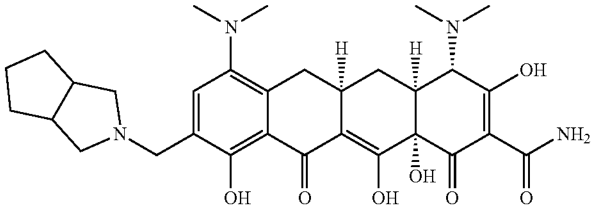 [SMILES: CN(C)c1cc(CN2CC3CCCC3C2)c(O)c2c1C[C@H]1C[C@H]3[C@H](N(C)C)C(O)=C(C(N)=O)C(=O)[C@@]3(O)C(O)=C1C2=O] |
| 112 | 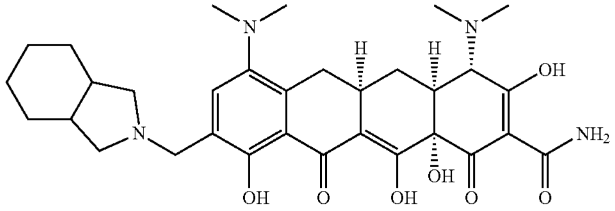 [SMILES: CN(C)c1cc(CN2CC3CCCCC3C2)c(O)c2c1C[C@H]1C[C@H]3[C@H](N(C)C)C(O)=C(C(N)=O)C(=O)[C@@]3(O)C(O)=C1C2=O] |

The term "alkyl" as used herein, includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (e.g., isopropyl, tert-butyl, isobutyl, etc.). The term alkyl also includes alkyl groups which can further include oxygen, nitrogen. sulfur or phosphorous atoms replacing one or more carbons of the hydrocarbon backbone. In some examples, a straight chain or branched chain alkyl may have 6 or fewer carbon atoms in its backbone (e.g., $C_1$-$C_6$ for straight chain, $C_3$-$C_6$ for branched chain), and more preferably 4 or fewer. The term "$C_1$-$C_6$" includes alkyl groups containing 1 to 6 carbon atoms.

The terms "alkoxyalkyl". "alkylaminoalkyl" and "thioalkoxyalkyl", as used herein, include alkyl groups, as described above, which further include oxygen, nitrogen or sulfur atoms replacing one or more carbons of the hydrocarbon backbone. e.g., oxygen, nitrogen or sulfur atoms.

Moreover, the term alkyl includes both "unsubstituted alkyls" and "substituted alkyls". the latter of which refers to alkyl moieties having substituents replacing a hydrogen on one or more carbons of the hydrocarbon backbone. Such substituents may include, for example, alkenyl, alkynyl, halogen, hydroxyl, alkylcarbonyloxy, arylcarbonyloxy. alkoxycarbonyloxy, aryloxycarbonyloxy. carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate. phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio. thiocarboxylate, sulfates, alkylsulfinyl, sulfonato, sulfamoyl. sulfonamido, nitro, trifluoromethyl, cyano, azido, heterocyclyl, alkylaryl, aryl or heteroaryl. An "alkylaryl" or an "arylalkyl" moiety is an alkyl substituted with an aryl (e.g., phenylmethyl (benzyl)).

The term "alkenyl", as used herein, includes unsaturated aliphatic groups analogous in length and possible substitution to the alkyls described above, but that contain at least one double bond. For example, the term "alkenyl" includes straight-chain alkenyl groups (e.g., ethylenyl. propenyl, butenyl. pentenyl, hexenyl, heptenyl, octenyl. nonenyl, decenyl, etc.) and branched-chain alkenyl groups. The term "alkenyl" may also include alkenyl groups which include oxygen, nitrogen, sulfur or phosphorous atoms replacing one or more carbons of the hydrocarbon backbone. In some examples, a straight chain or branched chain alkenyl group may have 6 or fewer carbon atoms in its backbone (e.g., $C_2$-$C_6$ for straight chain. $C_3$-$C_6$ for branched chain). The term "$C_2$-$C_6$" includes alkenyl groups containing 2 to 6 carbon atoms.

Moreover, the term "alkenyl" includes both "unsubstituted alkenyls" and "substituted alkenyls", the latter of which refers to alkenyl moieties having substituents replacing a hydrogen on one or more carbons of the hydrocarbon backbone. Such substituents may include, for example, substituents as listed above for alkyl groups.

The term "alkynyl". as used herein, includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.) and branched-chain alkynyl groups. The term "alkynyl" further includes alkynyl groups which may include oxygen, nitrogen, sulfur or phosphorous atoms replacing one or more carbons of the hydrocarbon backbone. In certain embodiments, a straight chain or a branched chain alkynyl group has 6 or fewer carbon atoms in its backbone (e.g., $C_2$-$C_6$ for straight chain, $C_3$-$C_6$ for branched chain). The term "$C_2$-$C_6$" includes alkynyl groups containing 2 to 6 carbon atoms.

Moreover, the term "alkynyl" includes both "unsubstituted alkynyls" and "substituted alkynyls", the latter of which refers to alkynyl moieties having substituents replacing a hydrogen on one or more carbons of the hydrocarbon backbone. Such substituents may include, for example, substituents as listed above for alkyl groups.

The term "cycloalkyl", as used herein, includes fully saturated cyclic hydrocarbon group containing from 1 to 4 rings and 3 to 8 carbons per ring. Exemplary cycloalkyl groups include cyclopropyl, cyclobutyl, cyclopentyl, cyclohexyl, cycloheptyl, cyclooctyl and the like. The term "cycloalkyl" also includes heterocyclyl groups, i.e., cycloalkyl groups which further include oxygen, nitrogen, sulfur or phosphorous atoms replacing one or more carbons of the hydrocarbon backbone. The term "cycloalkyl" also includes "polycyclyl" moieties that include two or more cyclic rings in which two or more carbons are common to two adjoining rings, e.g., the rings are "fused rings". Rings that are joined through non-adjacent atoms are termed "bridged" rings.

Moreover, the term "cycloalkyl" includes both "unsubstituted cycloalkyls" and "substituted cycloalkyls", the latter of which refers to cycloalkyl moieties having substituents replacing a hydrogen on one or more carbons of the hydrocarbon backbone. Such substituents may include, for example, substituents as listed above for alkyl groups.

The term "cycloalkenyl", as used herein, refers to a partially unsaturated cyclic hydrocarbon group containing 1 to 4 rings and 3 to 8 carbons per ring. Exemplary such groups include cyclobutenyl, cyclopentenyl, cyclohexenyl, etc. The term "cycloalkenyl" also includes "polycyclyl" moieties that include two or more cyclic rings in which two or more carbons are common to two adjoining rings, e.g., the rings are "fused rings". In some examples, the polycyclyl moieties may be bicyclic or trycyclic. Rings that are joined through non-adjacent atoms are termed "bridged" rings.

The term "cycloalkenyl" includes both "unsubstituted cycloalkenyls" and "substituted cycloalkenyls", the latter of which refers to cycloalkenyl moieties having substituents replacing a hydrogen on one or more carbons of the hydrocarbon backbone. Such substituents may include, for example, substituents as listed above for alkyl groups.

The term "aryl", as used herein, refers to cyclic, aromatic hydrocarbon groups containing 1 to 5 aromatic rings, especially monocyclic or bicyclic groups such as phenyl, biphenyl or naphthyl. Where containing two or more aromatic rings (e.g., bicyclic or tricyclic), the aromatic rings of the aryl group may be joined at a single point (e.g., biphenyl), or fused (e.g., naphthyl, phenanthrenyl and the like). The term "aryl" may also include groups, e.g., 5- and 6-membered single-ring aromatic groups, that may include from zero to four heteroatoms, such as pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics".

The term "aryl" also includes "polycyclyl" moieties that include two or more cyclic rings in which two or more carbons are common to two adjoining rings, e.g., the rings are "fused rings". Rings that are joined through non-adjacent atoms are termed "bridged" rings.

Moreover, the term "aryl" includes both "unsubstituted aryls" and "substituted aryls". the latter of which refers to aryl moieties having substituents replacing a hydrogen on the aromatic ring. Such substituents may include, for example, substituents as listed above for alkyl groups.

The term "acyl". as used herein, includes compounds and moieties which contain the acyl radical ($CH_3CO$—) or a carbonyl group. The term "substituted acyl" includes acyl groups where one or more of the hydrogen atoms are replaced by a substituent. e.g., selected from the group of substituents as listed above for alkyl groups.

The term "acylamino". as used herein, includes moieties wherein an acyl moiety is bonded to an amino group. For example, this term includes alkylcarbonylamino. arylcarbonylamino, carbamoyl and ureido groups.

The term "alkoxy", as used herein, includes substituted and unsubstituted alkyl, alkenyl, and alkynyl groups covalently linked to an oxygen atom. Examples of alkoxy groups include methoxy. ethoxy, isopropyloxy, propoxy, butoxy, and pentoxy groups. Examples of substituted alkoxy groups include halogenated alkoxy groups.

The term "amino" or "amine", as used herein, includes moieties wherein a nitrogen atom is covalently bonded to at least one carbon or heteroatom. This term also includes "alkylamino" wherein the nitrogen is bound to at least one additional alkyl group and the term "dialkylamino" wherein the nitrogen atom is bound to at least two additional alkyl groups. This term also includes "arylamino" and "diarylamino" wherein the nitrogen is bound to at least one or two aryl groups, respectively. This term also includes "alkylarylamino," "alkylaminoaryl" or "arylaminoalkyl" wherein the nitrogen is bound to at least one alkyl group and at least one aryl group. This term also includes "alkaminoalkyl" wherein an alkyl, alkenyl, or alkynyl group is bound to a nitrogen atom which is also bound to an alkyl group.

The term "aminocarbonyl" or "amide", as used herein, includes compounds or moieties which contain a nitrogen atom which is bonded to the carbon of a carbonyl or a thiocarbonyl group. This term includes "alkaminocarbonyl" or "alkylaminocarbonyl" groups wherein alkyl, alkenyl, aryl or alkynyl groups are bound to an amino group bound to a carbonyl group. This term also includes arylaminocarbonyl groups which include aryl or heteroaryl moieties bound to an amino group which is bound to the carbon of a carbonyl or thiocarbonyl group. The terms "alkylaminocarbonyl." "alkenylaminocarbonyl," "alkynylaminocarbonyl," "arylaminocarbonyl," "alkylcarbonylamino," "alkcnylcarbonylamino," "alkynylcarbonylamino," and "arylcarbonylamino" are also included in term "amide." Amides also include urea groups (aminocarbonylamino) and carbamates (oxycarbonylamino).

The term "carbonyl" or "carboxy", as used herein, includes compounds and moieties which contain a carbon connected with a double bond to an oxygen atom. Examples of moieties which contain a carbonyl include aldehydes, ketones. carboxylic acids. amides, esters, anhydrides, etc.

The term "thiocarbonyl" or "thiocarboxy". as used herein, includes compounds and moieties which contain a carbon connected with a double bond to a sulfur atom.

The term "ether", as used herein, includes compounds or moieties which contain an oxygen bonded to different carbon atoms or heteroatoms. For example, this term includes "alkoxyalkyl" which refers to an alkyl, alkenyl, or alkynyl group covalently bonded to an oxygen atom which is covalently bonded to another alkyl group.

The term "ester", as used herein, includes compounds and moieties which contain a carbon or a heteroatom bound to an oxygen atom which is bonded to the carbon of a carbonyl group. For example, this term includes alkoxycarboxy groups, such as methoxycarbonyl, ethoxycarbonyl, propoxycarbonyl, butoxycarbonyl, pentoxycarbonyl, etc.

The term "thioether", as used herein, includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" includes compounds with an alkyl, alkenyl, or alkynyl group bonded to a sulfur atom which is bonded to an alkyl group. Similarly, the term "alkthioalkenyls" and "alkthioalkynyls" refer to compounds or moieties wherein an alkyl, alkenyl, or alkynyl group is bonded to a sulfur atom which is covalently bonded to an alkynyl group.

The term "hydroxy" or "hydroxyl", as used herein, includes groups with an —OH or —O⁻.

The term "halogen" includes fluorine, bromine, chlorine, iodine. etc. The term "perhalogenated" generally refers to a moiety wherein all hydrogens are replaced by halogen atoms.

The term "heteroatom". as used herein, includes atoms of any element other than carbon or hydrogen. Preferred heteroatoms are nitrogen, oxygen. sulfur and phosphorus.

In some embodiments, the tetracycline compound administered to the subject within the context of the present invention is omadacycline, or a pharmaceutically acceptable salt, ester or a prodrug thereof. The term "omadacycline", which may also be used herein interchangeably with the terms "OMC", "PTK 0796", "Compound 1" or its brand name NUZYRA®, refers to (4aS,5aR,12aS)-4,7-bis(dimethylamino)-3,10,12,12a-tetrahydroxy-9-((neopentylamino)methyl)-1,11-dioxo-1,4,4a,5,5a,6,11,12a-octahydrotetracene-2-carboxamide, or 9-[(2,2-dimethyl-propyl amino)-methyl]-minocycline, or a pharmaceutically acceptable salt, ester or a prodrug thereof. Omadacycline may be represented by formula (4):

(4)

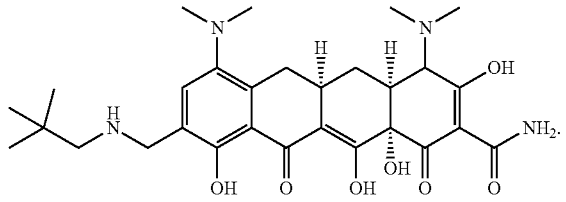

In some examples, omadacycline may be represented by formula (5):

(5)

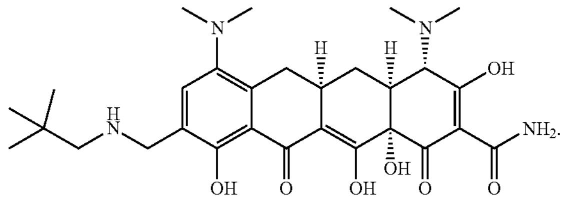

In some examples, omadacycline may be administered to the subject in the form a salt, e.g., a pharmaceutically acceptable salt, such as a tosylate salt. Tosylate salts of omadacycline may be amorphous or crystalline, e.g., Form 1 polymorph, Form 2 polymorph or Form 3 polymorph of the crystalline tosylate salt of omadacycline as described in U.S. Pat. No. 8,383,610, the entire contents of which are incorporated herein by reference. In some examples, omadacycline may be administered to the subject in the form of a freebase, e.g., crystalline freebase.

The term "mycobacterial infection", as used herein, refers to an infection caused by a *Mycobacterium*, i.e., a bacterium that belongs to the genus *Mycobacterium*. Methods of the present invention encompass treating infections caused by a bacterium that belongs to any species within the *Mycobacterium* genus. Mycobacteria are usually in the form of straight or slightly curved rods and possess a cell wall that is thick, hydrophobic and waxy. The cell wall of mycobacteria is rich in mycolic acids and mycolates and consists of the hydrophobic mycolate layer and a peptidoglycan layer held together by arabinogalactan, a polysaccharide. The thick cell wall of mycobacteria is one of the factors contributing to the mycobacterial infections being particularly difficult to treat.

Currently, about 188 bacterial species have been identified as belonging to the genus *Mycobacterium*. Several classification schemes have been used to divide mycobacteria into subgroups. For example, a classification scheme based on phylogenomic and comparative genomic analysis is described by Gupta et al., Frontiers in Microbiology 2018, 9:67, the entire contents of which are hereby incorporated herein by reference. This classification scheme identifies five main clades of mycobacterial species as follows: "*Abscessus-Chelonae*" clade, "*Fortuitum-Vaccae*" clade, "*Terrae*" clade, "*Triviale*" clade and "*Tuberculosis-Simiae*" clade. Of these clades, the "*Abscessus-Chelonae*" clade and the "*Fortuitum-Vaccae*" clade are comprised of rapid-growing mycobacteria, i.e., mycobacteria requiring less than 7 days to form colonies, while the "*Terrae*" clade, the "*Triviale*" clade and the "*Tuberculosis-Simiae*" clade are comprised of slow-growing mycobacteria, i.e., mycobacteria requiring more than 7 days to form colonies.

The "*Abscessus-Chelonae*" clade is comprised of the following mycobacterial species: *M. abscessus, M. abscessus* subsp. *abscessus, M. abscessus* subsp. *bolletii, M. abscessus* subsp. *massiliense, M. chelonae, M. chelonae* subsp. *chelonae, M. immunogenum, M. salmoniphilum, M. franklinii* and *M. saopaulense.*

The "*Fortuitum-Vaccae*" clade is comprised of the following mycobacterial species: *M. fortuitum, M. fortuitum* subsp. *fortuitum, M. fortuitum* subsp. *acetamidolyticum, M. acapulcense, M. agri, M. aichiense, M. alvei, M. anyangense, M. arabiense, M. arcueilence, M. aromaticivorans, M. aubagnense, M. aurum, M. austroafrinacum, M. bacteremicum, M. boenickei, M. brisnanense, M. brumae, M. canariasense, M. celeriflavum, M. chitae, M. chlorophenolicum, M. chubuense, M. conceprionense, M. confluentis, M. cosmeticum, M. crocinum, M. diernhoferi, M. doricum, M. duvalii, M. elephantis, M. fallax, M. facinogenes, M. flavescens, M. fluoranthenivorans, M. frederikspergense, M. gadium, M. gilvum, M. goodii, M. hassiacum, M. helvum, M. hippocampi, M. hodieri, M. holsaticum, M. houstonense, M. insubricum, M. iranicum, M. komanii, M. komossense, M. litorale, M. llatzerense, M. lutetiense, M. madagascariense, M. mageritense, M. malmesburyense, M. monacense, M. montmartrense, M. moriokaense, M. mucogenicum, M. murale, M. neoaurum, M. neworleansense, M. novocastrense, M. obuense, M. oryzae, M. pallens, M. parafortuitum, M. peregrinum, M. phlei, M. phocaicum, M. porcinum, M. ponferae, M. psychrotolerans, M. pulvens, M. pyrenivorans, M. rhodesiae, M. rufum, M. rutilum, M. sarraceniae, M. sediminis, M. senegalense, M. septicum, M. setense, M. smegmatis, M. sphagni, M. thermoresistibile, M. tokaiense, M. tusciae, M. vaccae, M. vanbaalenii, M. vulneris* and *M. wolinskyi.*

The "*Terrae*" clade is comprised of the following mycobacterial species: *M. terrae, M. algericus, M. arupensis, M. engbaekii, M. heraklionensis, M. hiberniae, M. icosiumassiliensis, M. kumamotonensis, M. longobardus, M. minnesotensis, M. nonchromogenicus, M. paraterrae, M. senuense, M. sinensis* and *M. virginiensis.*

The "*Triviale*" clade is comprised of the following mycobacterial species: *M. trivialis, M. koreensis* and *M. parakoreensis.*

The "*Tuberculosis-Simiae*" clade is comprised of the following mycobacterial species: *M. tuberculosis, M. tuberculosis* subsp. *tuberculosis, M. africanum, M. alsense, M. angelicum, M. arosiense, M. asiaticum, M. avium, M. avium* subsp. *avium, M. avium* subsp. *paratuberculosis, M. avium* subsp. *silvaticum, M. avium* subsp, *hominissuis, M. bohemicum, M. botniense, M. bouchedurhonense, M. bourgelatii, M. bovis, M. bovis* subsp. *bovis, M. bovis* subsp. *caprae, M. branderi, M. canettii, M. caprae, M. celatum, M. chimaera, M. colombiense, M. conspicuum, M. cookii, M. europaeum, M. florentinum, M. fragae, M. gastri, M. genavsnse, M. gordonae, M. haemophilum, M. heckshornense, M. heidelbergense, M. indicus pranii, M. interjectum, M. intermedium, M. intracellulare, M. kansasii, M. kubicae, M. kyorinense, M. lacus, M. lentiflavum, M. leprae, M. lepraemurium, M. lepromatosis, M. liflandii, M. malmoense, M. mantenii, M. marinum, M. marseillense, M. microti, M. monteriorense, M. mungi, M. nebraskense, M. novomagense, M. orygis, M. palustre, M. paraense, M. parraffinicum, M. paragordonae, M. paraintracellulare, M. parascrofulaceum, M. paraseculense, M. parmense, M. perscum, M. pinnipedii, M. pseudoshotsii, M. riyadhense, M. saskatchewanense, M. scrofulaceum, M. seculense, M. sherrisii, M. shimoidei, M. shinjukuense, M. shottsii, M. simiae, M. stomatepiae, M. szulgai, M. timonense, M. triplex, M. ulcerans, M. xenopi* and *M. yongonense.*

Accordingly, the present invention provides methods for treating or preventing a mycobacterial infection in a subject in need thereof that comprise administering to the subject a tetracycline compound as described above, e.g., omadacycline or a pharmaceutically acceptable salt, ester or a prodrug thereof, wherein the mycobacterial infection may be caused by a *Mycobacterium* belonging to any of the mycobacterial species as listed above. In some examples, the mycobacterial infection may be caused by *Mycobacterium* belonging to two or more of the mycobacterial species as listed above.

In some examples, the *Mycobacterium* may belong to a mycobacterial species *M. leprae* or *M. lepromatosis.*

In some examples, the *Mycobacterium* may belong to a *Mycobacterium tuberculosis* complex (MTBC). MTBC is a group of genetically related *Mycobacterium* species that can cause tuberculosis in a subject, e.g., a human. MTBC is comprised of the following species: *M. africanum, M. bovis, M. bovis BCG, M. canetti, M. caprae, M. microti, M. mungi, M. orygis, M. pinnipedii, M. suricattae* and *M. tuberculosis*. In one specific example, the *Mycobacterium* belongs to a mycobacterial species *M. tuberculosis.*

In some examples, the *Mycobacterium* may be a nontuberculous *Mycobacterium* (NTM). The term "NTM", as used herein, refers to a group of *Mycobacterium* species which do not cause tuberculosis or leprosy, but which may cause pulmonary diseases that may resemble tuberculosis, as well as diseases resulting from infections of lymph nodes, skin and soft tissues, bones and various punctures and wounds. The term "NTM" may be used herein interchangeably with the term "environmental mycobacteria", "atypical mycobacteria", or "mycobacteria other than tuberculosis (MOTT)".

The NTM, in some examples, may belong to a *Mycobacterium avium* complex (MAC). MAC is a group of mycobacteria which may include mycobacterial species *M. avium, M. avium paratuberculosis, M. avium silvaticum, M. avium "hominissuis", M. colombiense, M. chimaera, M. indicus pranii* and *M. intracellulare*. In further examples, the NTM mycobacterial species may be selected from the group consisting of *M. avium, M. avium paratuberculosis* and *M. intracellulare.*

In other examples, the NTM may belong to a *Mycobacterium chelonae* clade. The *Mycobacterium chelonae* clade may be comprised of the following mycobacterial species: *M. abscessus, M. bolletii, M. chelonae, M. immunogenum* and *M. stephanolepidis*. In one specific example, the NTM may be *M. abscessus*. In another specific example, the NTM may be *M. chelonae.*

The NTM may also belong to a *Mycobacterium fortuitum* clade. The *Mycobacterium fortuitum* clade may be comprised of the following mycobacterial species: *M. boenickei, M. brisbanense, M. cosmeticum, M. fortuitum, M. fortuitum* subsp. *acetamidolyticum, M. houstonense, M. mageritense, M. neworleansense, M. peregrinum, M. porcinum, M. senegalense* and *M. septicum*. In one specific example, the *Mycobacterium* causing mycobacterial infection is of the mycobacterial species *M. fortuitum.*

In some examples, the NTM may also belong to one or more of the following mycobacterial species: *M. kansasii, M. genavense, M. gordonae, M. haemophilum, M. immunogenum, M. malmoense, M. marinum, M. mucogenicum, M. nonchromogenicum, M. scrofulaceum, M. simiae, M. smegmatis, M. szulgai, M. terrae complex, M. ulcerans* and *M. xenopi.*

In other examples, the NTM may also belong to one or more of the following mycobacterial species: *M. avium, M. intracellulare, M. kansasii, M. paratuberculosis, M. scrofulaceum, M. simiae, M. habana, M. interjectum, M. xenopi, M. heckeshornense, M. szulgai, M. fortuitum, M. immunogenum, M. chelonae, M. marinum, M. genavense, M. haemophilum, M. celatum, M. conspicuum, M. malmoense, M. ulcerans, M. smegmatis, M. wolinskyi, M. goodii, M. thermoresistible, M. neoaurum, M. vaccae, M. palustre, M. elephantis, M. bohemicam* and *M. septicum.*

In some examples, the present invention provides methods for treating or preventing a mycobacterial infection in a subject in need thereof that comprise administering to the subject a tetracycline compound as described above, e.g., omadacycline or a pharmaceutically acceptable salt, ester or a prodrug thereof, wherein the mycobacterial infection is caused by a slow-growing *Mycobacterium*. The term "slow-growing *Mycobacterium*" or SGM, as used herein, which may be used interchangeably with the term "slowly-growing *Mycobacterium*", "slowly-growing mycobacteria" and "slow-growing mycobacteria, refers to a *Mycobacterium* that requires more than 7 days to form colonies, e.g., colonies visible to the naked eye when cultured in vitro.

As described above, the "*Terrae*" clade, the "*Triviale*" clade and the "*Tuberculosis-Simiae*" clade are comprised of the slow-growing mycobacteria.

The "*Terrae*" clade comprising slow-growing mycobacteria includes the following mycobacterial species: *M. terrae, M. algericus, M. arupensis, M. engbaekii, M. heraklionensis, M. hiberniae, M. icosiumassiliensis, M. kumamotonensis, M. longobardus, M. minnesotensis, M. nonchromogenicus, M. paraterrae, M. senuense, M. sinensis and M. virginiensis.*

The "*Triviale*" clade comprising slow-growing mycobacteria includes the following mycobacterial species: *M. trivialis, M. koreensis* and *M. parakoreensis.*

The "*Tuberculosis-Simiae*" clade comprising slow-growing mycobacteria includes the following mycobacterial species: *M. tuberculosis, M. tuberculosis* subsp. *tuberculosis, M. africanum, M. alsense, M. angelicum, M. arosiense, M.*

*asiaticum, M. avium, M. avium* subsp. *avium, M. avium* subsp. *paratuberculosis, M. avium* subsp. *silvaticum, M. avium* subsp. *hominissuis, M. bohemicum, M. botniense, M. bouchedurhonense, M. bourgelatii, M. bovis, M. bovis* subsp. *bovis, M. bovis* subsp. *caprae, M. branderi, M. canettii, M. caprae, M. celatum, M. chimaera, M. colombiense, M. conspicuum, M. cookii, M. europaeum, M. florentinum, M. fragae, M. gastri, M. genavsnse, M. gordonae, M. haemophilum, M. heckshornense, M. heidelbergense, M. indicus pranii, M. interjectum, M. intermedium, M. intracellulare, M. kansasii, M. kubicae, M. kyorinense, M. lacus, M. lentiflavum, M. leprae, M. lepraemurium, M. lepromatosis, M. liflandii, M. malmoense, M. mantenii, M. marinum, M. marseillense, M. microti, M. monteriorense, M. mungi, M. nebraskense, M. novomagense, M. orygis, M. palustre, M. paraense, M. parraffinicum, M. paragordonae, M. paraintracellulare, M. parascrofulaceum, M. paraseculense, M. parmense, M. perscum, M. pinnipedii, M. pseudoshotsii, M. riyadhense, M. saskatchewanense, M. scrofulaceum, M. seculense, M. sherrisii, M. shimoidei, M. shinjukuense, M. shottsii, M. simiae, M. stomatepiae, M. szulgai, M. timonense, M. triplex, M. ulcerans, M. xenopi* and *M. yongonense.*

In some examples, the slow-growing *Mycobacterium* may be NTM, e.g., a *Mycobacterium* belonging to MAC. MAC includes the following mycobacterial species: *M. avium, M. avium paratuberculosis, M. avium silvaticum, M. chimaera, M. avium "hominissuis, M. colombiense, M. indicus* pranii and *M. intracellulare*. In other examples, the slow-growing *Mycobacterium* may belong to a mycobacterial species selected from the group consisting of *M. haemophilum, M. kansasii, M. malmoense, M. marinum, M. simiae* and *M. xenopi*.

In some examples, the slow-growing mycobacteria may belong to a *Mycobacterium tuberculosis* complex (MTBC), e.g., may belong to one of the following mycobacterial species: *M. africanum, M. bovis, M. bovis BCG, M. canetti, M. caprae, M. microti, M. mungi, M. orygis, M. pinnipedii, M. suricattae* and *M. tuberculosis*. In one specific example, the slow-growing *Mycobacterium* belongs to a mycobacterial species *M. tuberculosis.*

In some examples, the present invention provides methods for treating or preventing a mycobacterial infection in a subject in need thereof that comprise administering to the subject a tetracycline compound as described above, e.g., omadacycline or a pharmaceutically acceptable salt, ester or a prodrug thereof, wherein the mycobacterial infection is caused by a rapid-growing *Mycobacterium*. The term "rapid-growing *Mycobacterium*", also referred to herein as "RGM", and which may be used interchangeably with the term "rapidly-growing *Mycobacterium*", "rapidly-growing mycobacteria" and "rapid-growing mycobacteria, refers to a *Mycobacterium* that requires less than 7 days to form colonies, e.g., colonies visible to the naked eye, when cultured in vitro.

As described above, the "*Abscessus-Chelonae*" clade and the "*Fortuitum-Vaccae*" clade are comprised of rapid-growing mycobacteria.

The "*Abscessus-Chelonae*" clade comprised of the rapid-growing mycobacteria includes the following mycobacterial species: *M. abscessus, M. abscessus* subsp. *abscessus, M. abscessus* subsp. *bolletii, M. abscessus* subsp. *massiliense, M. chelonae, M. chelonae* subsp. *chelonae, M. immunogenum, M. salmoniphilum, M. franklinii* and *M. saopaulense*. In some embodiments, the mycobacteria comprised in the "*Abscessus-Chelonae*" clade is NTM.

The "*Fortuitum-Vaccae*" clade is comprised of the rapid-growing mycobacteria includes the following mycobacterial species: *M. fortuitum, M. fortuitum* subsp. *fortuitum, M. fortuitum* subsp. *acetamidolyticum, M. acapulcense, M. agri, M. aichiense, M. alvei, M. anyangense, M. arabiense, M. arcueilence, M. aromaticivorans, M. aubagnense, M. aurum, M. austroafrinacum, M. bacteremicum, M. boenickei, M. brisnanense, M. brumae, M. canariasense, M. celeriflavum, M. chitae, M. chlorophenolicum, M. chubuense, M. conceprionense, M. confluentis, M. cosmeticum, M. crocinum, M. diernhoferi, M. doricum, M. duvalii, M. elephantis, M. fallax, M. facinogenes, M. flavescens, M. fluoranthenivorans, M. frederikspergense, M. gadium, M. gilvum, M. goodii, M. hassiacum, M. helvum, M. hippocampi, M. hodieri, M. holsaticum, M. houstonense, M. insubricum, M. iranicum, M. komanii, M. komossense, M. litorale, M. llatzerense, M. lutetiense, M. madagascariense, M. mageritense, M. malmesburyense, M. monacense, M. montmartrense, M. moriokaense, M. mucogenicum, M. murale, M. neoaurum, M. neworleansense, M. novocastrense, M. obuense, M. oryzae, M. pallens, M. parafortuitum, M. peregrinum, M. phlei, M. phocaicum, M. porcinum, M. ponferae, M. psychrotolerans, M. pulvens, M. pyrenivorans, M. rhodesiae, M. rufum, M. rutilum, M. sarraceniae, M. sediminis, M. senegalense, M. septicum, M. setense, M. smegmatis, M. sphagni, M. thermoresistibile, M. tokaiense, M. tusciae, M. vaccae, M. vanbaalenii, M. vulneris* and *M. wolinskyi*. In some embodiments, the mycobacteria belonging to the "*Fortuitum-Vaccae*" clade is NTM.

In some examples, the rapid-growing *Mycobacterium* may be NTM, e.g., a *Mycobacterium* belonging to the following mycobacterial species: *M. abscessus, M. chelonae, M. fortuitum, M. smegmatis, M. peregrinum* or *M. mucogenicum*. In some examples, the rapid-growing mycobacteria may belong to the mycobacterial species *M. abscessus, M. chelonae* or *M. fortuitum.*

In some examples, the *Mycobacterium* may be a drug resistant *Mycobacterium*, e.g., a multidrug resistant *Mycobacterium*, such as extensively drug resistant (XDR) *Mycobacterium* or pan-drug resistant (PDR) *Mycobacterium*. For example, the *Mycobacterium* may be resistant to at least one drug selected from the group consisting of rifampicin, isoniazid, INH-ethionamide, streptomycin, fluoroquinolone, pyrazinamide, ethambutol, linezolid, clofazimine, a macrolide antibiotic, a P-lactam antibiotic, or a combination thereof. The macrolide antibiotic may be selected from the group consisting of azithromycin, clarithromycin, erythromycin, fidaxomicin, telithromycin, carbomycin A, josamycin, kitasamycin, midecamycin/midecamycin acetate, oleandomycin, solithromycin, spiramycin, troleandomycin, tylosin/tylocine and roxithromycin. The P-lactam antibiotics may be selected from the group consisting of penicillins, e.g., penicillin G, penicillin V, benzylpenicillin, pheneticillin, cloxacillin, dicloxacillin, flucloxacillin, methicillin, nafcillin, oxacillin, temocillin, amoxicillin, ampicillin, mecillinam, carbenicillin, ticarcillin, azlocillin, mezlocillin and piperacillin; cephalosporins, e.g., cefazolin, cephalexin, cephalosporin C, cephalothin, cefaclor, cefamandole, cefuroxime, cefotetan, cefoxitin, cefixime, cefotaxime, cefpodoxime, ceftazidime, ceftriaxone, cefepime, cefpirome and ceftaroline; carbapenems, e.g., biapenem, doripenem, ertapenem, faropenem, imipenem, meropenem, panipenem, razupenem, tebipenem and thienamycin; monobactams, e.g., aztreonam, tigemonam, nocardicin A, and tabtoxinine β-lactam; and β-lactamase inhibitors, e.g., clavulanic acid, tazobactam, sulbactam and avibactam.

In one example, the *Mycobacterium* may be resistant to rifampicin. In another example, the *Mycobacterium* may be resistant to isoniazid. In yet another example, the *Mycobacterium* may be resistant to a combination of rifampicin and isoniazid. In yet another example, the *Mycobacterium* may be resistant to a macrolide antibiotic. In other examples, the *Mycobacterium* may be resistant to amikacin, ethambutol, moxifloxacin, rifampin, or streptomycin.

The term "resistance" or "resistant" refers to the ability of a microorganism, e.g., a *Mycobacterium*, to resist the effect of an antibiotic drug, e.g., the ability to survive and continue growing when exposed to the antibiotic. This term also encompasses known lack of effectiveness of certain antibiotics against certain mycobacterial species. In some examples, this term also refers to the antibiotic/organism standards as defined by the Clinical and Laboratories Standards Institute (CLSI) and/or the Food and Drug Administration (FDA).

Methods of Treating or Preventing Diseases Associated with Mycobacterial Infections The present invention also provides methods for treating or preventing a mycobacterial disease in a subject in need thereof. The methods of treating or preventing a mycobacterial disease comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above.

In some examples, the tetracycline compound administered to the subject within the context of the present invention is omadacycline ("OMC", or "PTK 0796" or "Compound 1", also known as NUZYRA®), or a pharmaceutically acceptable salt, ester or a prodrug thereof, that is represented by formula (4):

(4)

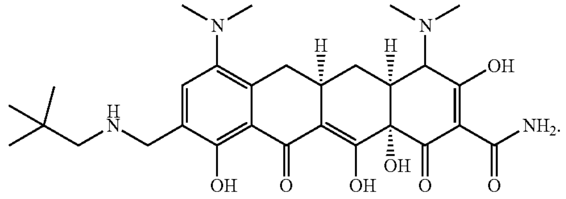

In some examples, omadacycline may be represented by formula (5):

(5)

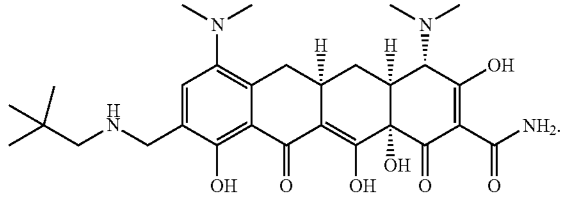

The term "mycobacterial disease", as used herein, refers to a disease that may be associated with, e.g., caused by, a mycobacterial infection. A mycobacterial infection may be an infection with any one or more of the mycobacterial species as listed above.

In some examples, the tetracycline compound, e.g., omadacycline or a pharmaceutically acceptable salt, ester or a prodrug thereof, may be administered to the subject for treating or preventing a mycobacterial disease in the form a salt. The salt may be a pharmaceutically acceptable salt, such as a tosylate salt. For example, tosylate salts of omadacycline may be amorphous or crystalline, e.g., Form 1 polymorph, Form 2 polymorph or Form 3 polymorph of the crystalline tosylate salt of omadacycline as described in U.S. Pat. No. 8,383,610, the entire contents of which are incorporated herein by reference. In some examples, tetracycline compound, e.g., omadacycline or a pharmaceutically acceptable salt, ester or a prodrug thereof, may be administered to the subject in the form of a freebase, e.g., crystalline freebase.

In some examples, the mycobacterial disease may be caused by infection with a *Mycobacterium* belonging to MTBC, e.g., *M. tuberculosis*. For example, the disease may be tuberculosis. *Tuberculosis* generally affects the lungs, but can also affect other parts of the body, such as kidneys, spine and the brain. Latent tuberculosis is asymptomatic, but may progress to an active disease which, if left untreated, may kill about half of those infected. The classic symptoms of active tuberculosis are chronic cough with blood-containing sputum, fever, night sweats, and weight loss.

In some examples, the mycobacterial disease may be caused by an infection with a *Mycobacterium* belonging to the mycobacterial species *M. leprae* or *M. lepromatosis*. For example, the mycobacterial disease may be leprosy, also known as Hansen's Disease (HD). Symptoms of leprosy may include granulomas of the nerves, respiratory tract, skin, and eyes. This may eventually cause inability to feel pain, which may lead to the loss of parts of extremities due to repeated injuries or infection due to unnoticed wounds. Weakness and poor eyesight may also present as the symptoms.

In some examples, the mycobacterial disease may be a pulmonary disease. Non-limiting examples of pulmonary disease may include bronchiectasis, e.g., idiopathic or nodular bronchiectasis, pulmonary infection, e.g., pulmonary infection with a *Mycobacterium* and a combination thereof.

In some examples, the mycobacterial disease may be an NTM disease, i.e., may be associated with an NTM infection. Mycobacterial diseases associated with NTM infections have been described, for example, by Katoch, *Indian J. Med. Res.* 2004, 120:290-304, the entire contents of which are incorporated herein by reference. For example, the NTM disease may be a pulmonary (lung) NTM disease characterized by symptoms that may comprise one or more of the following: chronic or recurring cough, sputum production, fatigue, malaise, dyspnea (i.e., difficult or labored breathing), fever, hemoptysis (i.e., coughing up of blood or blood-stained mucus from the bronchi, larynx, trachea, or lungs), chest pain and weight loss. In certain specific examples, the pulmonary NTM disease may be caused by an infection with *M. abscessus*. In other examples, the pulmonary NTM disease may be associated with an infection with MAC, e.g., a *Mycobacterium* belonging to one of the following mycobacterial species: *M. avium, M. kansasii, M. scrofulaceum, M. xenopi, M. simiae, M. habana, M. szulgai, M. fortuitum, M. vaccae, M. malmoense* or *M. heckeshornense*.

In some examples, the pulmonary disease may be a cavitary lung disease. The term "cavitary lung disease" as used herein, refers to any disease characterized by the presence of cavities in the lungs. The term "cavity" or "cavity present in the lungs", as used herein, may refer to any radiographic opacity with an internal area of lucency, regardless of wall thickness. In one example, the cavity may be a gas-filled space within a zone of pulmonary consolidation or within a mass or nodule, produced by the expulsion of a necrotic part of the lesion via the bronchial tree. In another example, a cavity may also be a lucency within a zone of pulmonary consolidation, a mass, or a nodule; hence, a lucent area within the lung that may or may not contain a fluid level and that is surrounded by a wall, usually of varied thickness.

A cavity may result from any pathological process, for example, from including suppurative necrosis (e.g., pyogenic lung abscess), caseous necrosis (e.g., tuberculosis), ischemic necrosis (e.g., pulmonary infarction), cystic dilatation of lung structures (e.g., ball valve obstruction and *Pneumocystis pneumonia*), or displacement of lung tissue by cystic structures (e.g., *Echinococcus*).

In one example, cavitary lung disease may result from a mycobacterial infection, e.g., from infection with any mycobacterial species as listed above. In one further example, the cavitary lung disease may result from an infection with *M. tuberculosis*. In another further example, the cavitary lung disease may result from an infection with *M. abscessus*.

The severity of the pulmonary disease may range from asymptomatic to severe, e.g., the pulmonary disease may be asymptomatic, mild, moderate, or severe. In one specific example, the pulmonary disease may be asymptomatic bronchiectasis, mild bronchiectasis, moderate bronchiectasis or severe bronchiectasis.

In other examples, the NTM disease may be lymphadenitis. Lymphadenitis is a lymphatic disease characterized by symptoms that may comprise presence of enlarged lymph nodes that may sometimes rupture, with formation of sinus tracts that result in prolonged local drainage. In some examples, the lymphadenitis may be associated with an infection with MAC, e.g., a *Mycobacterium* belonging to one of the following mycobacterial species: *M. avium, M. scrofulaceum, M. bohemicum, M. szulgai* or *M. interjectum.*

The NTM disease may also be a skin disease, an eye disease, a soft tissue disease or a bone disease, which may, in some examples, be associated with an infection of a wound or a site of an open traumatic injury with NTM, resulting in a lesion. In some examples, the NTM disease may be a skin infection e.g., cellulitis, or an eye disease caused by an infection of an eye with a *Mycobacterium* that belongs to a *Mycobacterium chelonae* clade, e.g., a *Mycobacterium* that belongs to the mycobacterial species *M. chelonae*. Such infections may result from *M. chelonae* mycobacteria contaminating various facilities and/or appliances, e.g., water heaters, pedicure beds, tattoo parlors and hospitals. In some examples, *M. chelonae* may be resistant to routine disinfectants, such as chlorine and glutaraldehyde. In some examples, the subject infected with a *Mycobacterium* belonging to a *Mycobacterium* chelonae clade, e.g., *M. chelonae*, may be immunocompetent. In other examples, the subject infected with a *Mycobacterium* belonging to a *Mycobacterium chelonae* clade, e.g., *M. chelonae*, may be immunocompromised.

In other examples, the NTM disease may be a soft tissue infection or a hospital acquired post-operative injection, e.g., may be associated with an infection with a bacterium belonging to a *Mycobacterium fortuitum* clade, such as the mycobacterial species *M. fortuitum.*

The NTM disease may also be a disease associated with an osteoarticular infection, e.g., an infection in a joint or a bone of a subject with an NTM.

In yet other examples, the NTM disease may be aquarium granuloma, also known as "fish tank granuloma" or "swimming pool granuloma". Aquarium granuloma may be a skin lesion caused by an infection with *M. marinum.*

The NTM disease may also be a Buruli ulcer caused, e.g., by an infection of skin and/or bones with *M. ulcerans.*

The NTM disease may also be associated with an NTM infection of a site at which a foreign object has been introduced or placed into a subject. For example, the infection may involve a site wherein a medical device, an implant or a tattoo ink has been introduced into a subject. The medical device may be, e.g., a cardiac pacemaker. The implant may be a cardiovascular implant, such as a heart valve; an orthopedic implant, such as a pin, a rod, a screw or a plate; or a cosmetic implant, such as a breast implant, a nose prosthesis or an injectable filler.

In yet other examples, the NTM disease may be a disseminated disease. The disseminated NTM disease primarily affects immunocompromised subjects, e.g., subjects infected with HIV and subject with AIDS. In some examples, the disseminated NTM disease in HIV-infected subjects may be characterized by symptoms that may comprise one or more of the following: fever, night sweats, weight loss, abdominal pain or diarrhea. In some examples, the disseminated disease is associated with an infection of a nervous system, e.g., central nervous system (CNS), such as meningitis.

In some embodiments, the present invention also provides methods for treating or preventing tuberculosis in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In some examples, the present invention also provides methods of controlling or reducing the advancement, severity or effects of tuberculosis in a subject in need thereof that comprise administering to the subject an effective amount of a tetracycline compound, or a pharmaceutically acceptable salt. ester or a prodrug thereof, wherein the tetracycline compound is represented by formula (1), formula (2), formula (3), formula (4) or formula (5) as described above. In certain embodiments, the tetracycline compound is omadacycline or a pharmaceutically acceptable salt thereof.

In some embodiments, the present invention also provides methods for treating or preventing leprosy in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In some examples, the present invention also provides methods of controlling or reducing the advancement, severity or effects of leprosy in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In certain embodiments, the tetracycline compound is omadacycline or a pharmaceutically acceptable salt thereof.

In some embodiments, the present invention also provides methods for treating or preventing bronchiectasis in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In some examples, the present invention also provides methods of controlling or reducing the advancement, severity or effects of bronchiectasis in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In certain embodiments, the tetracycline compound is omadacycline or a pharmaceutically acceptable salt thereof.

In some embodiments, the present invention also provides methods for treating or preventing cavitary lung disease in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In some examples, the present invention also provides methods of controlling or reducing the advancement, severity or effects of cavitary lung disease in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In certain embodiments, the tetracycline compound is omadacycline or a pharmaceutically acceptable salt thereof.

In some embodiments, the present invention also provides methods for treating or preventing lymphadenitis in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In some examples, the present invention also provides methods of controlling or reducing the advancement, severity or effects of lymphadenitis in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In certain embodiments, the tetracycline compound is omadacycline or a pharmaceutically acceptable salt thereof.

In some embodiments, the present invention also provides methods for treating or preventing a soft tissue disease in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In some examples, the present invention also provides methods of controlling or reducing the advancement, severity or effects of a soft tissue disease in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In certain embodiments, the soft tissue disease is a skin disease, e.g., cellulitis. In certain embodiments, the tetracycline compound is omadacycline or a pharmaceutically acceptable salt thereof.

In some embodiments, the present invention also provides methods for treating or preventing aquarium granuloma in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In some examples, the present invention also provides methods of controlling or reducing the advancement, severity or effects of aquarium granuloma in a subject in need thereof that comprise administering to the subject an effective amount of a tetracycline compound, or a pharmaceutically acceptable salt. ester or a prodrug thereof, wherein the tetracycline compound is represented by formula (1), formula (2), formula (3), formula (4) or formula (5) as described above. In certain embodiments, the tetracycline compound is omadacycline or a pharmaceutically acceptable salt thereof.

In some embodiments, the present invention also provides methods for treating or preventing Buruli ulcer in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In some examples, the present invention also provides methods of controlling or reducing the advancement, severity or effects of Buruli ulcer in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In certain embodiments, the tetracycline compound is omadacycline or a pharmaceutically acceptable salt thereof.

In some embodiments, the present invention also provides methods for treating or preventing an eye disease in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In some examples, the present invention also provides methods of controlling or reducing the advancement, severity or effects of an eye disease in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In certain embodiments, the tetracycline compound is omadacycline or a pharmaceutically acceptable salt thereof.

In some embodiments, the present invention also provides methods for treating or preventing a bone disease in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In some examples, the present invention also provides methods of controlling or reducing the advancement, severity or effects of a bone disease in a subject in need thereof that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In certain embodiments, the tetracycline compound is omadacycline or a pharmaceutically acceptable salt thereof.

Administration of a Tetracycline Compound for Treating or Preventing Mycobacterial Infections or Mycobacterial Diseases The tetracycline compound, e.g., omadacycline or a pharmaceutically acceptable salt, ester or a prodrug thereof, may be administered to a subject in need thereof for treating or preventing a mycobacterial infection or treating or preventing a mycobacterial disease alone or as a part of a pharmaceutical composition. Any exemplary pharmaceutical composition comprising the tetracycline compound, e.g., omadacycline or a pharmaceutically acceptable salt, ester or a prodrug thereof, may comprise an effective amount of the tetracycline compound, e.g., a salt of omadacycline or omadacycline freebase, and, optionally, a pharmaceutically acceptable carrier. The tetracycline compound, such as the salt of omadacycline, e.g., tosylate salt, or omadacycline freebase, may in an amorphous form or in a crystalline form.

The language "pharmaceutically acceptable carrier" includes substances capable of being co-administered with a tetracycline compound, e.g., omadacycline, or a pharmaceutically acceptable salt, ester or a prodrug thereof, and which may allow both to perform their intended function, e.g., treat or prevent a bacterial infection. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, and the like. The pharmaceutical compositions may be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with omadacycline, or a pharmaceutically acceptable salt, ester or a prodrug thereof.

The pharmaceutical compositions that may be used in the methods of the present invention for treating or preventing mycobacterial infections or mycobacterial diseases may be adapted for administration via either the oral, parenteral, or topical routes. In some examples, the pharmaceutical compositions that may be used in the methods of the present invention may also be adapted for delivery via aerosol. In general, tetracycline compounds are most desirably administered in effective dosages, depending upon the weight and condition of the subject being treated and the particular route of administration chosen. Variations may occur depending upon the species of the subject being treated and its individual response to the tetracycline compound, as well as on the type of pharmaceutical composition chosen and the time period and interval at which such administration is carried out.

For oral administration, the tetracycline compound, e.g., omadacycline, or a pharmaceutically acceptable salt, ester or a prodrug thereof, may be administered in the form of a tablet or a capsule. The tablet or a capsule may comprise various excipients, e.g., an excipient selected from the group consisting of microcrystalline cellulose, sodium citrate, calcium carbonate, dicalcium phosphate and glycine. The tablet or a capsule may also comprise a disintegrant, e.g., starch (and preferably corn, potato or tapioca starch), alginic acid and certain complex silicates. The tablet or a capsule may also comprise a granulation binder, e.g., sucrose, gelatin or acacia. Additionally, lubricating agents, such as magnesium stearate, sodium lauryl sulfate and talc may also be added to a tablet or a capsule for tableting purposes.

For parenteral administration (including intraperitoneal, subcutaneous, intravenous, intradermal or intramuscular injection), the present invention also provides injectable formulations comprising a tetracycline compound as described above, e.g., omadacycline, or a pharmaceutically acceptable salt, ester or a prodrug thereof. Such injectable formulations may be in the form of a dry, e.g., lyophilized, powder, that is reconstituted with a carrier, e.g., an aqueous carrier, such as water, prior to administration. In some embodiments, the injectable formulation may also comprise at least one or more of an additional ingredient, such as a lyoprotectant, an antioxidant and a pH adjustment compound.

Certain pharmaceutical compositions comprising omadacycline, or a pharmaceutically acceptable salt, ester or a prodrug thereof, that may be suitable for use in the methods of the present invention, are described, e.g., in U.S. Pat. No. 9,315,475, the entire contents of which are hereby incorporated herein by reference.

In the methods of the present invention, the tetracycline compound of formula (1), formula (2), formula (3), formula (4) or formula (5), e.g., omadacycline or a pharmaceutically acceptable salt, ester or a prodrug thereof, may also be administered to a subject by an aerosol. An aerosol pharmaceutical composition comprising the tetracycline compound, e.g., omadacycline or a pharmaceutically acceptable salt, ester or a prodrug thereof, may be in the form of a solution, a suspension, a powder formulation or a liposomal formulation. An aerosol pharmaceutical composition comprising the tetracycline compound, e.g., omadacycline, may be contained in an aerosol dispenser that may, in some examples, also comprise a metered dose spray device. In some examples, the aerosol dispenser may be a nebulizer, e.g., a small-volume nebulizer (SVN), a pressurized metered-dose inhaler (pMDI) or a dry-powder inhaler (DPI). Administration of a tetracycline compound, e.g., omadacycline, or a pharmaceutically acceptable salt, ester or a prodrug thereof, via an aerosol within the context of the present invention may be particularly useful for treating a pulmonary disease, e.g., a pulmonary disease associated with a mycobacterial infection.

For topical administration, the tetracycline compound, e.g., omadacycline or a pharmaceutically acceptable salt, ester or a prodrug thereof, may also be administered to a subject as a part of a pharmaceutical composition adapted for topical administration. Such compositions may be in a form of a gel, an ointment, a lotion or a cream, and may comprise the tetracycline compound suitably admixed in a pharmacologically inert topical carrier. The pharmacologically inert topical carriers may include water, glycerol, alcohol, propylene glycol, fatty alcohols, triglycerides, fatty acid esters, or mineral oils. Other possible topical carriers may be liquid petrolatum, isopropylpalmitate, polyethylene glycol, ethanol, polyoxyethylene monolauriate, sodium lauryl sulfate and the like. In addition, materials such as anti-oxidants, humectants, viscosity stabilizers and the like also may be added if desired.

The tetracycline compounds described herein, e.g., omadacycline or a pharmaceutically acceptable salt, ester or a prodrug thereof, may be administered to a subject for treating or preventing a mycobacterial infection or a mycobacterial disease at a dose, e.g., daily dose, of from about 100 to about 200 mg, from about 100 to about 300 mg, from about 100 to 400 mg, from about 100 to about 500 mg, from about 100 to about 600 mg, from about 200 to about 500 mg, or from about 300 to about 600 mg of tetracycline compound. In a further example, a tetracycline compound, e.g., omadacycline or a pharmaceutically acceptable salt, ester or a prodrug thereof, may be administered orally. In a further examples, tetracycline compound, e.g., omadacycline or a pharmaceutically acceptable salt, ester or a prodrug thereof, may be administered intravenously.

In some aspects, tetracycline compound, e.g., omadacycline or a pharmaceutically acceptable salt, ester or a prodrug thereof, may be administered to a subject at a dose of about 50 to about 150 mg, about 50 to about 400 mg, about 50 to about 300 mg, about 50 to about 200 mg, about 100 to about 300 mg or about 200 to about 300 mg, or about 100 mg. For example, the tetracycline compound may be administered to a subject at a dose, e.g., a daily dose, of about 100 mg, about 150 mg, about 200 mg, about 250 mg or about 300 mg. In one embodiment, the dose is an intravenous dose.

In some aspects, tetracycline compound, e.g., omadacycline or a pharmaceutically acceptable salt, ester or a prodrug thereof, may be administered to a subject at a dose of from about 50 to about 800 mg, about 100 to about 700 mg, about 250 to about 600 mg, about 300 to about 500 mg, about 100 to about 400 mg, about 100 to about 600 mg, or about 300 mg. For example, the tetracycline compound may be administered at a dose of about 300 mg, about 450 mg or about 600 mg. In one embodiment, the dose is an oral dose.

In an embodiment, tetracycline compound, e.g., omadacycline or a pharmaceutically acceptable salt, ester or a prodrug thereof, may be administered intravenously at a dose of about 100 mg, about 200 mg, or about 300 mg. In another embodiment, omadacycline, or salt thereof, may be administered orally at the dose of about 300 mg, about 600 mg, or about 900 mg.

In some examples, tetracycline compound, e.g., omadacycline or a pharmaceutically acceptable salt, ester or a prodrug thereof, may be administered as an aerosol dose, e.g., delivered using an aerosol dispenser. In some examples, the aerosol dispenser may comprise at a dose of tetracycline compound, e.g., omadacycline or a pharmaceutically acceptable salt, ester or a prodrug thereof, of about 1 to about 2000 mg, e.g., about 1 to about 500 mg, about 25 to about 300 mg, about 50 to about 400 mg, about 100 to about 500 mg, about 200 to about 800 mg, about 500 mg to about 1000 mg, about 10 mg to about 200 mg or about 300 mg to about 700 mg. In some examples, the aerosol dispenser may comprise a dose of tetracycline compound, e.g., omadacycline or a pharmaceutically acceptable salt, ester or a prodrug thereof, of about 1 mg, about 5 mg, about 10 mg, about 30 mg, about 50 mg, about 80 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg or about 1000 mg.

In some examples, tetracycline compound, e.g., omadacycline or a pharmaceutically acceptable salt, ester or a prodrug thereof, may be administered topically, e.g., by applying to an affected area pharmaceutical composition adapted for topical administration comprising tetracycline compound, e.g., omadacycline or a pharmaceutically acceptable salt, ester or a prodrug thereof. For example, the pharmaceutical composition adapted for topical administration may be in the form of a solution and comprise tetracycline compound, e.g., omadacycline or a pharmaceutically acceptable salt, ester or a prodrug thereof, at a concentration of about 0.01% to about 20% w/v based on the volume of the composition, e.g., about 0.01% to about 10% w/v, about 0.1% to about 20% w/v, about 0.5% to about 5% w/v, about 1% to about 10% w/v or about 5% to about 20% w/v. For example, the pharmaceutical composition adapted for topical administration may comprise tetracycline compound, e.g., omadacycline or a pharmaceutically acceptable salt, ester or a prodrug thereof, at a concentration of about 0.01% w/v, about 0.05% w/v, about 0.1% w/v, about 0.5% w/v, about 1% w/v, about 5% w/v, about 10% w/v, about 15% w/v or about 20% w/v.

In another example, the pharmaceutical composition adapted for topical administration may comprise tetracycline compound, e.g., omadacycline or a pharmaceutically acceptable salt, ester or a prodrug thereof, at a concentration of about 0.01% to about 20% w/w based on the volume of the composition, e.g., about 0.01% to about 10% w/w, about 0.1% to about 20% w/w, about 0.5% to about 5% w/w, about 1% to about 10% w/w or about 5% to about 20% w/w. For example, the pharmaceutical composition adapted for topical administration may comprise tetracycline compound, e.g., omadacycline or a pharmaceutically acceptable salt, ester or a prodrug thereof, at a concentration of about 0.01% w/w, about 0.05% w/w, about 0.1% w/w, about 0.5% w/w, about 1% w/w, about 5% w/w, about 10% w/w, about 15% w/w or about 20% w/w.

In some examples, tetracycline compound, e.g., omadacycline or a pharmaceutically acceptable salt, ester or a prodrug thereof, may be administered at the doses as described above at least once daily, e.g., once daily, twice daily, three times daily or four times daily. In further examples, the tetracycline compound, e.g., omadacycline or a pharmaceutically acceptable salt, ester or a prodrug thereof, is administered to a subject twice daily. In one specific example, the tetracycline compound, e.g., omadacycline or a pharmaceutically acceptable salt, ester or a prodrug thereof, is administered orally to a subject twice daily.

It should be understood that administration of dose ranges comprising the above listed doses is also included in the present invention. For example, any of the above doses may be a lower part or an upper part of a dose range that is included in the methods of the present invention. Even further, it should be understood that all lists or collections of numerical values used throughout the present application also are intended to include ranges of the numerical values wherein any of the listed numerical values can be the lower part or upper part of a range. These ranges are intended to be included in the present invention.

In one embodiment, an oral dose of the tetracycline compound, e.g., omadacycline or a pharmaceutically acceptable salt, ester or a prodrug thereof, may be 3 times larger than an intravenous dose of omadacycline, or a pharmaceutically acceptable salt, ester or a prodrug thereof.

It will be understood that for all listed embodiments, the dose of tetracycline compound, e.g., omadacycline or a pharmaceutically acceptable salt, ester or a prodrug thereof, is also an effective amount of the omadacycline, or a pharmaceutically acceptable salt, ester or a prodrug thereof.

In one embodiment, the effective amount of tetracycline compound, e.g., omadacycline or a pharmaceutically acceptable salt, ester or a prodrug thereof, when administered orally, may be from about 100 to about 1000 mg of the tetracycline compound, e.g., from about 200 to about 750 mg, about 100 to about 500 mg, about 200 to about 600 or about 400 to about 600. In a further example, the effective amount of tetracycline compound, e.g., omadacycline or a pharmaceutically acceptable salt, ester or a prodrug thereof, when administered orally, may be about 300 mg, about 450 mg or about 600 mg of the tetracycline compound.

In another embodiment, the effective amount of tetracycline compound, e.g., omadacycline or a pharmaceutically acceptable salt, ester or a prodrug thereof, when administered intravenously, may be from about 50 to about 500 mg omadacycline, or a pharmaceutically acceptable salt, ester or a prodrug thereof, e.g., about 50 to about 400 mg, about 100 to about 300 mg or about 50 to about 200 mg. For example, the effective amount of tetracycline compound, e.g., omadacycline or a pharmaceutically acceptable salt, ester or a prodrug thereof, when administered intravenously, may be about 100 mg, about 150 mg, about 200 mg, about 250 mg or about 300 mg.

In some examples, tetracycline compound, e.g., omadacycline or a pharmaceutically acceptable salt, ester or a prodrug thereof, may be administered in the context of the present invention via either the oral, parenteral, systemic, topical routes, or via aerosol delivery. In general, tetracycline compound, e.g., omadacycline or a pharmaceutically acceptable salt, ester or a prodrug thereof, is most desirably administered in an effective dosage, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

In some embodiments, tetracycline compound, e.g., omadacycline or a pharmaceutically acceptable salt, ester or a prodrug thereof, may be administered for at least 3 days, at least 7 days, at least 14 days, at least 21 days, at least 30 days, at least 60 days, at least 5 weeks, at least 10 weeks, at least 15 weeks, at least 20 weeks, at least 30 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, or at least 24 months. For example, the administration of tetracycline compound, e.g., omadacycline or a pharmaceutically acceptable salt, ester or a prodrug thereof, may last from 3 days to 7 days, from 3 days to 14 days, from 3 days to 21 days, from 3 days to 30 days, from 3 days to 60 days, from 7 days to 14 days, from 7 days to 21 days, from 7 days to 30 days, from 7 days to 60 days, from 14 days to 21 days, from 14 days to 30 days, from 14 days to 60 days, from 21 days to 30 days, from 21 days to 60 days, from 30 days to 60 days, from 1 week to 5 weeks, from 3 weeks to 10 weeks, from 5 weeks to 20 weeks, from 10 weeks to 30 weeks, from 20 weeks to 35 weeks, from 1 week to 1 month, from 2 weeks to 2 months, from 1 month to 3 months, from 1 month to 6 months, from 1 month to 9 months, from 3 months to 12 months, from 6 months to 12 months, from 9 months to 12 months, from 9 months to 16 months, from 12 months to 18 months, from 14 months to 24 months, from 12 months to 24 months, or for 24 months or longer.

For example, tetracycline compound, e.g., omadacycline or a pharmaceutically acceptable salt, ester or a prodrug thereof, may be administered for 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months or 24 months. In other examples, the tetracycline compound, e.g., omadacycline or a pharmaceutically acceptable salt, ester or a prodrug thereof, may be administered for longer than 24 months, e.g., 25 months, 26 months, 27 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 month, or longer than 48 months.

In some embodiments, administration of tetracycline compound, e.g., omadacycline or a pharmaceutically acceptable salt, ester or a prodrug thereof, to a subject may comprise administering one or more loading doses of the tetracycline compound, followed by one or more maintenance doses of the tetracycline compound. In some embodiments, the one or more loading dose of tetracycline compound, e.g., omadacycline or a pharmaceutically acceptable salt, ester or a prodrug thereof, may be greater than the one or more maintenance dose of the tetracycline compound, e.g., omadacycline or a pharmaceutically acceptable salt, ester or a prodrug thereof. For example, the loading dose may be about 450 mg daily dose, e.g., a daily oral dose, while the maintenance dose may be about 300 mg daily dose, e.g., a daily oral dose. In another example, the loading dose may be about 200 mg daily dose, e.g., a daily intravenous dose, while the maintenance dose may be about 100 mg daily dose, e.g., a daily intravenous dose, or a 300 mg daily dose, e.g., a daily oral dose.

The loading dose of tetracycline compound, e.g., omadacycline or a pharmaceutically acceptable salt, ester or a prodrug thereof, and the maintenance dose of tetracycline compound, e.g., omadacycline or a pharmaceutically acceptable salt, ester or a prodrug thereof, may be administered via the same route or different routes. For example, the loading dose(s) may be administered intravenously and the maintenance dose may be administered orally. In other embodiments, both the loading dose(s) and the maintenance doses may be administered orally, or both the loading dose(s) and the maintenance dose may be administered intravenously.

In some examples, the loading dose of tetracycline compound, e.g., omadacycline or a pharmaceutically acceptable salt, ester or a prodrug thereof, may be an oral dose or an intravenous dose administered twice daily, and the maintenance dose may be an oral dose or an intravenous dose administered once daily. For example, tetracycline compound, e.g., omadacycline or a pharmaceutically acceptable salt, ester or a prodrug thereof, may be administered as an intravenous loading dose of 100 mg twice daily, followed by an intravenous maintenance dose of 100 mg once daily. In another example tetracycline compound, e.g., omadacycline or a pharmaceutically acceptable salt, ester or a prodrug thereof, may be administered as an intravenous loading dose of 100 mg twice daily, followed by an oral maintenance dose of 300 mg once daily. In yet another example, tetracycline compound, e.g., omadacycline or a pharmaceutically acceptable salt, ester or a prodrug thereof, may be administered as an oral loading dose of 300 mg twice daily, followed by an oral maintenance dose of 300 mg once daily.

In another example, administration of tetracycline compound, e.g., omadacycline or a pharmaceutically acceptable salt, ester or a prodrug thereof, may not comprise administration of one or more loading doses of the tetracycline compound. Thus, in some examples, tetracycline compound, e.g., omadacycline or a pharmaceutically acceptable salt, ester or a prodrug thereof, may be administered to a subject at the same dose throughout the treatment period. For example, tetracycline compound, e.g., omadacycline or a pharmaceutically acceptable salt, ester or a prodrug thereof, may be administered to the subject at an intravenous dose of about 100 mg, about 200 mg or about 300 mg. The intravenous dose may be administered to the subject once or twice daily throughout the treatment. In another example, tetracycline compound, e.g., omadacycline or a pharmaceutically acceptable salt, ester or a prodrug thereof, may be administered to a subject at an oral dose of about 300 mg, about 450 mg or about 600 mg. The oral dose may be administered to the subject once daily throughout the treatment period.

In some examples, tetracycline compound, e.g., omadacycline or a pharmaceutically acceptable salt, ester or a prodrug thereof, may be administered to a subject for treating or preventing a mycobacterial infection or a mycobacterial disease alone or in combination with at least one additional anti-mycobacterial agent. The language "in combination with" an anti-mycobacterial agent is intended to include simultaneous administration of tetracycline compound, e.g., omadacycline or a pharmaceutically acceptable salt, ester or a prodrug thereof, and the anti-mycobacterial agent; administration of tetracycline compound, e.g., omadacycline or a pharmaceutically acceptable salt, ester or a prodrug thereof, first, followed by the anti-mycobacterial agent; and administration of the anti-mycobacterial agent first, followed by tetracycline compound, e.g., omadacycline or a pharmaceutically acceptable salt, ester or a prodrug thereof.

In some examples, the tetracycline compound, e.g., omadacycline or a pharmaceutically acceptable salt, ester or a prodrug thereof and at least one additional anti-mycobacterial agent may be administered to a subject as a part of the same pharmaceutical composition. In further examples, a pharmaceutical composition comprising the tetracycline compound, e.g., omadacycline, and at least one additional anti-mycobacterial agent may be an aerosol pharmaceutical composition. In other examples, a pharmaceutical composition comprising the tetracycline compound, e.g., omadacycline, and at least one additional anti-mycobacterial agent may be a pharmaceutical composition adapted for topical administration.

Any anti-mycobacterial agent known in the art may be used in the methods of the invention, including, e.g., an anti-mycobacterial agent that is known or suspected to be effective against a mycobacterial infection, or an anti-mycobacterial agent that has been shown to have an additive or a synergistic activity with the tetracycline compounds described herein, e.g., omadacycline or a pharmaceutically acceptable salt, ester or a prodrug thereof. In some examples, the anti-mycobacterial agent may be selected from the group consisting of a diarylquinolone, rifapentine, rifalazil, a nitroimidazole, a benzothiazinone, capreomycin, clofazimine, cycloserine, dapsone, a thiocarbamide, ethambutol, DC-159a, a nitrobenzthiazole, sutezolid (PNU-100480), AZD-5847, posizolid (AZD-2563), para-aminosalicylic acid, SQ-109, SQ-609, a capuramycin, a caprazene nucleoside, an isothiazoloquinolone, thioridazine, thiacetazone, dirithromycin, roxithromycin, telithromycin, azithromycin, clarithromycin, erythromycin, amikacin, kanamycin, streptomycin, levofloxacin, moxifloxacin, gatifloxacin, linezolid, rifalazil, imipenem, meropenem, clavulanate and isoniazid. In other examples, the anti-mycobacterial agent may be selected from the group consisting of rifampicin, isoniazid, INH-ethionamide, streptomycin, fluoroquinolone, pyrazinamide, ethambutol, linezolid, clofazimine, a macrolide antibiotic, or a combination thereof. In further examples, the macrolide antibiotic may be selected from the group consisting of azithromycin, clarithromycin, erythromycin, fidaxomicin, telithromycin, carbomycin A, josamycin, kitasamycin, midecamycin/midecamycin acetate, oleandomycin, solithromycin, spiramycin, troleandomycin, tylosin/tylocine and roxithromycin.

The term "treating" or "treatment", as used herein, includes one or more of the following: (a) inhibiting, controlling, arresting, reducing, or delaying the advancement or the development of a mycobacterial infection or a mycobacterial disease, or a relapse thereof in case of maintenance treatment, of at least one clinical or subclinical symptom thereof; and/or (b) relieving, i.e., ameliorating or diminishing at least one clinical or subclinical symptom of a mycobacterial infection or a mycobacterial disease. The benefit to a subject to be treated is either statistically significant or at least perceptible to the subject or to the physician.

The term "prophylaxis", "prevent", "preventing" or "prevention", as used herein, includes preventing or reducing the risk of a mycobacterial infection or a mycobacterial disease. In some examples, this term includes preventing or delaying the appearance of clinical symptoms of a mycobacterial infection or a mycobacterial disease, in a subject who may already be infected with a *Mycobacterium* but who has not yet developed a mycobacterial disease, or who is not displaying symptoms of a mycobacterial infection or a mycobacterial disease. In some examples, this term also includes reducing the likelihood that a subject who has been exposed to a *Mycobacterium* will develop a mycobacterial infection, a mycobacterial disease, or a symptom thereof.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of a symptom of a mycobacterial infection or a mycobacterial disease, and preferably at least 20%, 30%, 40%, 50% or more, may be indicative of effective treatment. In another example, any positive change resulting in e.g., lessening of severity of a symptom of a mycobacterial infection or a mycobacterial disease measured using the appropriate scale, represents adequate treatment using tetracycline compound, e.g., omadacycline or a pharmaceutically acceptable salt, ester or a prodrug thereof, as described herein.

The term "effective amount", as used herein, includes the amount of tetracycline compound, e.g., omadacycline or a pharmaceutically acceptable salt, ester or a prodrug thereof, needed to treat or prevent a mycobacterial infection or a mycobacterial disease. For example, the term "effective amount" describes an efficacious level sufficient to achieve the desired therapeutic effect through the killing of mycobacteria and/or inhibition of mycobacterial growth. In one embodiment, the effective amount is sufficient to eradicate the *Mycobacterium* or mycobacteria causing the mycobacterial infection or a mycobacterial disease.

The term “subject” includes animals which are subject to a mycobacterial infection or a mycobacterial disease. Examples of subjects include animals such as farm animals (e.g., cows, pigs, horses, goats, rabbits, sheep, chickens, etc.), lab animals (mice, rats, monkeys, chimpanzees, etc.), pets (e.g., dogs, cats, ferrets, hamsters, etc.), birds (e.g., chickens, turkeys, ducks, geese, crows, ravens, sparrows, etc.), primates (e.g., monkeys, gorillas, chimpanzees, bonobos, and humans), and other animals (e.g., squirrels, raccoons, mice, rats, etc.). In one embodiment, the subject is a mouse or rat. In one embodiment, the subject is a cow, a pig, or a chicken. In one embodiment, the subject is a human.

In some examples, in addition to a mycobacterial infection or a mycobacterial disease, the subject may have another disease or a pathological condition. In some examples, another disease or a pathological condition may be a disease of the lungs, such as chronic obstructive pulmonary disease (COPD), an occupational lung disease, tuberculosis, bronchiectasis, e.g., idiopathic or nodular bronchiectasis, cystic fibrosis, primary ciliary dyskinesia, allergic bronchopulmonary aspergillosis, alpha-one antitrypsin deficiency, pneumoconiosis, interstitial lung disease (from any cause), chronic aspiration syndrome or pulmonary alveolar proteinosis.

In other examples, the subject may be immunocompromised, i.e., have another disease or a pathological condition that may be associated with an immunological defect or an immunosuppressed condition. An immunological defect or an immunosuppressed condition may be associated with an HIV infection and/or AIDS; taking immunosuppressive medications, e.g., anti-cancer therapy or medications to suppress immune system after an organ transplant; taking biological anti-inflammatory agents, e.g., acetaminophen; common variable immunoglobulin deficiency syndrome; or a genetic disorder resulting in an immunological defect, e.g., a genetic defect in interferon-γ receptor or in interleukin-12. In some examples, the immunocompromised subject is a subject with cancer. In such subjects, the suppression of the immune system may be an effect of cancer, or an effect of a medication, e.g., chemotherapy, taken by the subject for treating cancer.

In one example, the subject may have a lung disease. Non-limiting examples of lung disease may include cystic fibrosis, chronic obstructive pulmonary disease (COPD), alpha 1 antitrypsin deficiency and bronchiectasis, e.g., idiopathic or nodular bronchiectasis. In other examples, the subject may be immunocompromised or immunosuppressed, e.g., have an HIV infection and/or AIDS. In yet another example, the subject may have undergone an organ transplantation, e.g., a lung transplantation.

In some embodiments, the subject may be immunocompromised. In other embodiments, the subject may be immunocompetent. In some embodiments, the subject may have previously undergone treatment for tuberculosis.

In some examples, the subject has been determined to have a mycobacterial infection prior to the administration of tetracycline compound, e.g., omadacycline or a pharmaceutically acceptable salt, ester or a prodrug thereof. Accordingly, methods of the present invention may also comprise the step of determining that the subject has a mycobacterial infection prior to administering tetracycline compound, e.g., omadacycline or a pharmaceutically acceptable salt, ester or a prodrug thereof, to the subject. Determining that the subject has a mycobacterial infection may be accomplished by any method known in the art for diagnosing mycobacterial infections.

In some embodiments, the present invention also provides methods for treating a subject with a lung disease that comprise administering to the subject an effective amount of a tetracycline compound, or a pharmaceutically acceptable salt, ester or a prodrug thereof, wherein the tetracycline compound is represented by formula (1), formula (2), formula (3), formula (4) or formula (5) as described above. In certain embodiments, the tetracycline compound is omadacycline or a pharmaceutically acceptable salt thereof.

In some examples, the lung disease may be selected from the group consisting of cystic fibrosis, chronic obstructive pulmonary disease (COPD), an occupational lung disease, bronchiectasis, cavitary lung disease, primary ciliary dyskinesia, allergic bronchopulmonary aspergillosis, alpha 1 antitrypsin deficiency, pneumoconiosis, interstitial lung disease, chronic aspiration syndrome and pulmonary alveolar proteinosis.

In one example, the lung disease may be cystic fibrosis. In another example, the lung disease may be chronic obstructive pulmonary disease (COPD). In yet another example, the lung disease may be an occupational lung disease. In yet another example, the lung disease may be bronchiectasis, e.g., idiopathic or nodular bronchiectasis. In yet another example, the lung disease may be cavitary lung disease. In yet another example, the lung disease may be primary ciliary dyskinesia. In yet another example, the lung disease may be allergic bronchopulmonary aspergillosis. In yet another example, the lung disease may be alpha 1 antitrypsin deficiency. In yet another example, the lung disease may be pneumoconiosis. In yet another example, the lung disease may be interstitial lung disease. In yet another example, the lung disease may be chronic aspiration syndrome. In yet another example, the lung disease may be pulmonary alveolar proteinosis.

In some embodiments, the present invention also provides methods for treating a subject with an immunosuppressed condition that comprise administering to the subject an effective amount of a tetracycline compound, or a pharmaceutically acceptable salt. ester or a prodrug thereof, wherein the tetracycline compound is represented by formula (1), formula (2), formula (3), formula (4) or formula (5) as described above. In certain embodiments, the tetracycline compound is omadacycline or a pharmaceutically acceptable salt thereof.

In one example, the immunosuppressed condition may be associated with and HIV infection or with AIDS. In another example, the immunosuppressed condition may be associated with administration to the subject of an immunosuppressive medication, e.g., a chemotherapeutic agent administered as a part of anti-cancer therapy; an immunosuppressive agent administered after an organ transplant; or an anti-inflammatory agent, such as acetaminophen. In yet another example, the immunosuppressed condition may be a result of an immunological defect, i.e., a defect in the function of the immune system caused by a disease, e.g., AIDS of cancer, or a genetic defect. For example, in some embodiments, the immunosuppressed condition may be a result of a genetic disorder, such as a genetic defect in interferon-γ receptor or in interleukin-12.

In some embodiments, administration of tetracycline compound, e.g., omadacycline or a pharmaceutically acceptable salt, ester or a prodrug thereof, to a subject for treating or preventing a mycobacterial infection, or for treating or preventing a disease caused by, or associated with, a mycobacterial infection, does not result in substantial adverse effects. In some examples, the administration may be an oral administration. In some examples, the adverse effects may be gastrointestinal adverse effects, such as nausea or vomiting. In some embodiments, administration of tetracycline compound, e.g., omadacycline or a pharmaceutically acceptable salt, ester or a prodrug thereof, according to the methods of the present invention does not require administration of an antiemetic agent, such as ondansetron.

The term "about", as used herein, refers to a range of values which can be 15%, 10%, 8%, 5%, 3%, 2%, 1%, or 0.5% more or less than the specified value. For example, "about 10%" can be from 8.5% to 11.5%. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

It is to be understood that wherever values and ranges are provided herein, e.g., in ages of subject populations, dosages, and time durations, etc., all values and ranges encompassed by these values and ranges, are meant to be encompassed within the scope of the present invention. Moreover, all values in these values and ranges may also be the upper or lower limits of a range.

EXEMPLIFICATION OF THE INVENTION

Example 1. In Vitro Activity of Omadacycline Against M. abscessus, M. Chelonae and M. fortuitum Infections with *Mycobacterium abscessus*, *Mycobacterium chelonae* and *Mycobacterium fortuitum* are difficult to treat. The purpose of this study was to evaluate the in vitro activity of omadacycline against clinical isolates of *Mycobacterium abscessus*, *Mycobacterium chelonae* and *Mycobacterium fortuitum* and to compare it to the in vitro activities of doxycycline, tigecycline and amikacin against the same clinical isolates.

Methods

A total of 24 clinical isolates of *Mycobacterium abscessus*, 22 clinical isolates of *Mycobacterium chelonae* and 20 clinical isolates of *Mycobacterium fortuitum* were tested in the study. The study also used the antibiotics tigecycline, doxycycline and amikacin for comparison purposes. Omadacycline, tigecycline and doxycycline were each dissolved in distilled water and sterilized by filtration prior to freezing at −20° C. Amikacin was dissolved in DMSO prior to freezing at −20° C. For susceptibility testing, stock solutions of antibiotic compounds were serially diluted in 50 μL of cation adjusted Mueller-Hinton broth (CAMHB) in polystryrene 96-well round-bottom microtiter plates. To each well, 50 μL of the appropriate mycobacterial cell suspension was added to yield a final concentration of about 1×10$^5$ CFU/mL. The inoculum used for each isolate was measured by titration in saline with Tween 80 and plating on MH agar. The *Mycobacterium abscessus* and *Mycobacterium fortuitum* titer plates were incubated at 37° C. in ambient air for 3-4 days and 5-7 days, respectively. The *Mycobacterium chelonae* titer plates were incubated at 30° C. in ambient air for 3-5 days. Each isolate was tested at least in duplicate. The MIC was defined as the lowest concentration of antimicrobial agent yielding no visible turbidity.

Results

MIC values measured for each *Mycobacterium abscessus* isolate are presented in Table 2 below. MIC$_{90}$ and MIC$_{90}$ measured for *Mycobacterium abscessus* isolates are presented in Table 3 below. Tigecycline was tested against a subset of *Mycobacterium abscessus* isolates (N=14) and was determined to have activity against *Mycobacterium abscessus* isolates similar to that of omadacycline.

TABLE 2

MIC values (μg/mL) measured for each *Mycobacterium abscessus* isolate.

| Isolate No. | Isolate Name | Amikacin | Doxycycline | Omadacycline | Tigecycline |
|---|---|---|---|---|---|
| 1 | BB2 | 8 | >64 | 1 | 2 |
| 2 | BB4 | 8 | 2 | 4 | 2 |
| 3 | 5922 | 2 | 16 | 0.125 | 0.25 |
| 4 | BB3 | 2 | 4 | 0.06 | 0.06 |
| 5 | BB6 | 4 | 16 | 0.06 | 0.125 |
| 6 | 5908 | 2 | >64 | 1 | 2 |
| 7 | BB7 | 0.5 | 0.25 | 2 | 2 |
| 8 | 6031 | 0.5 | 2 | 0.25 | 1 |
| 9 | 5785 | 1 | 2 | 0.25 | 0.5 |
| 10 | BB8 | 2 | >64 | 1 | |
| 11 | 6111 | 2 | >64 | 1 | 0.5 |
| 12 | 6005 | 4 | >64 | 1 | 0.5 |
| 13 | 5605 | 2 | >64 | 1 | |
| 14 | 5931 | 0.5 | 16 | 1 | |
| 15 | BB1 | 2 | >64 | 2 | |
| 16 | BB5 | 8 | >64 | 2 | 1 |
| 17 | 5812 | 4 | >64 | 2 | |
| 18 | 5901 | 2 | >64 | 1 | |
| 19 | 5960 | 1 | 8 | 8 | 8 |
| 20 | 6142 | 4 | >64 | 1 | |
| 21 | 5922 | 2 | 32 | 0.5 | |
| 22 | LT 949 | 8 | >64 | 1 | |
| 23 | 6025 | 8 | >64 | 1 | 1 |
| 24 | 6153 | 8 | >64 | 2 | |

TABLE 3

MIC$_{50}$ and MIC$_{90}$ values (μg/mL) measured for *Mycobacterium abscessus* isolates.

| Antibiotic | MIC$_{50}$ (μg/mL) | MIC$_{90}$ (μg/mL) |
|---|---|---|
| Omadacycline | 1 | 2 |
| Tigecycline | 1 | 2 |
| Doxycycline | >64 | >64 |
| Amikacin | 2 | 8 |

MIC values measured for each *Mycobacterium chelonae* isolate are presented in Table 4 below. MIC$_{50}$ and MIC$_{90}$ measured for *Mycobacterium chelonae* isolates are presented in Table 5 below.

TABLE 4

MIC values (μg/mL) measured for each *Mycobacterium chelonae* isolate.

| Isolate No. | Isolate Name | Amikacin | Doxycycline | Omadacycline | Tigecycline |
|---|---|---|---|---|---|
| 1 | MC 7323 | 4 | 64 | 0.125 | 0.125 |
| 2 | MC 7534 | 8 | 32 | 0.03 | 0.03 |
| 3 | MC 7368 | 16 | 64 | 0.03 | 0.03 |
| 4 | MC 7514 | 8 | 32 | 0.06 | 0.06 |
| 5 | MC 7584 | 4 | 64 | 0.06 | 0.06 |
| 6 | MC 7192 | 4 | 16 | 0.015 | 0.03 |
| 7 | MC 7466 | 2 | 32 | 0.03 | 0.03 |
| 8 | MC 7533 | 4 | 64 | 0.25 | 0.125 |

TABLE 4-continued

MIC values (μg/mL) measured for each *Mycobacterium chelonae* isolate.

| Isolate No. | Isolate Name | Amikacin | Doxycycline | Omadacycline | Tigecycline |
|---|---|---|---|---|---|
| 9 | MC 7579 | 4 | 16 | 0.125 | 0.03 |
| 10 | MC 7614 | 8 | 64 | 0.125 | 0.125 |
| 11 | MC 7414 | 4 | 32 | 0.125 | 0.06 |
| 12 | MC 7313 | 2 | 32 | 0.125 | 0.25 |
| 13 | MC 7281 | 8 | 64 | 0.25 | 0.5 |
| 14 | MC 7328 | 8 | 16 | 0.015 | 0.015 |
| 15 | MC 7294 | 8 | 32 | 0.25 | 0.125 |
| 16 | MC 14-S-03 | 4 | 64 | 0.06 | 0.5 |
| 17 | MC 14-S-04 | 4 | 32 | 0.06 | 0.06 |
| 18 | MC 14-S-05 | 8 | 32 | 0.125 | 0.125 |
| 19 | MC 14-S-06 | 8 | 64 | 0.03 | 0.03 |
| 20 | MC 14-S-07 | 4 | 32 | 0.06 | 0.06 |
| 21 | MC 35757 | 2 | 32 | 0.125 | 0.125 |
| 22 | MC 7302 | 4 | 64 | 0.25 | 0.25 |

TABLE 5

$MIC_{50}$ and $MIC_{90}$ values (μg/mL) measured for *Mycobacterium chelonae* isolates.

| Antibiotic | $MIC_{50}$ (μg/mL) | $MIC_{90}$ (μg/mL) |
|---|---|---|
| Omadacycline | 0.125 | 0.25 |
| Tigecycline | 0.06 | 0.125 |
| Doxycycline | 32 | 64 |
| Amikacin | 4 | 8 |

MIC values measured for each *Mycobacterium fortuitum* isolate are presented in Table 6 below. $MIC_{50}$ and $MIC_{90}$ measured for *Mycobacterium fortuitum* isolates are presented in Table 7 below.

TABLE 6

MIC values (μg/mL) measured for each *Mycobacterium fortuitum* isolate.

| Isolate No. | Isolate Name | Amikacin | Doxycycline | Omadacycline | Tigecycline |
|---|---|---|---|---|---|
| 1 | 3349 | 8 | 16 | 0.25 | 0.25 |
| 2 | 3499 | 0.25 | 0.06 | 0.03 | 0.015 |
| 3 | 2797 | 2 | >64 | 0.125 | 0.06 |
| 4 | 32 | 1 | 0.125 | 0.25 | 0.25 |
| 5 | 33 | 2 | 0.125 | 0.125 | 0.125 |
| 6 | 3489 | 1 | 8 | 0.125 | 0.015 |
| 7 | 3491 | 1 | <0.06 | 0.125 | 0.015 |
| 8 | 54 | 0.5 | <0.06 | 0.06 | 0.03 |
| 9 | 38 | 0.5 | 0.5 | 0.125 | 0.06 |
| 10 | 36 | 1 | 0.125 | 0.125 | 0.03 |
| 11 | 3480 | 0.5 | 16 | 0.25 | 0.25 |
| 12 | 3126 | 0.5 | 16 | 0.125 | 0.25 |
| 13 | 3579 | 1 | 16 | 0.25 | 0.25 |
| 14 | 7484 | 16 | 64 | 0.5 | 0.5 |
| 15 | 3488 | 0.5 | 32 | 0.5 | 0.25 |
| 16 | 3276 | 0.5 | 0.25 | 0.25 | 0.25 |
| 17 | 3442 | 0.5 | 0.25 | 1 | 1 |
| 18 | 3316 | 0.125 | 32 | 0.125 | 0.25 |
| 19 | 3490 | 0.5 | 16 | 0.25 | 0.25 |
| 20 | 2491 | 4 | >64 | 1 | 0.5 |

TABLE 7

$MIC_{50}$ and $MIC_{90}$ values (μg/mL) measured for *Mycobacterium fortuitum* isolates.

| Antibiotic | $MIC_{50}$ (μg/mL) | $MIC_{90}$ (μg/mL) |
|---|---|---|
| Omadacycline | 0.125 | 0.5 |
| Tigecycline | 0.25 | 0.25 |
| Doxycycline | 8 | 64 |
| Amikacin | 0.5 | 4 |

Conclusions

The results presented in Tables 2-7 demonstrate that omadacycline has promising activity against *Mycobacterium abscessus, Mycobacterium chelonae* and *Mycobacterium fortuitum* isolates.

Example 2. In Vitro Activity of Omadacycline Against *M. abscessus*

Introduction

*Mycobacterium abscessus* belongs to the heterogeneous group of non-tuberculous mycobacteria (NTM) and can cause severe infections in patients with underlying structural lung diseases such as cystic fibrosis (CF). The incidence of NTM infections in CF patients is rising and *M. abscessus* is one of the most frequently isolated species (Adjemian et al., *Ann Am Thorac Soc.* 2018, 15(7):817-26). This is important as pulmonary infections with *M. abscessus* in this patient population have been shown to be responsible for the most rapid lung function decline compared to other pathogens (Qvist et al., *J Cyst Fibros.* 2016, 15(3):380-5). In addition, in most medical centers, *M. abscessus* infection is a relative contra-indication for lung transplantation. Therefore, appropriate treatment of *M. abscessus* infections in CF patients is crucial.

Among the different NTM species, *M. abscessus* is notorious because of its intrinsic resistance to multiple antibiotics. This is especially true for *M. abscessus* subspecies *abscessus*, characterized by the presence of a functional erythromycin ribosomal methylase (erm) gene and conferring inducible resistance to macrolides, which are considered cornerstone agents in treatment (Guo et al., *Antimicrob Agents Chemother.,* 2018, 62(5)). As a consequence, *M. abscessus* infections are extremely difficult to treat, requiring a combination of different intravenous and oral antimycobacterial drugs for a prolonged period of time. The drug regimens are usually poorly tolerated and despite intensive treatment, outcomes are disappointing (Pasipanodya et al., *Antimicrob Agents Chemother.,* 2017; 61(11)).

The purpose of this study was to explore the potential use of omadacycline for the treatment of *M. abscessus* infections. In this context, the in vitro activity of omadacycline against *M. abscessus* was assessed and compared to the activity of tigecycline.

Methods

Bacterial Strain and Culture

The *M. abscessus* subsp. *abscessus* CIP 104536 (Collection of Institute Pasteur, Paris, France) was cultured in cation-adjusted Mueller-Hinton II broth (Becton, Dickinson and Company (BD), Sparks, MD, USA) supplemented with 10% oleic acid-albumin-dextrose-catalase enrichment (OADC, BD) and 0.5% glycerol (Scharlau Chemie SA, Sentmenat, Spain) under shaking conditions at 96 rpm at 37° C. Vials with *M. abscessus* suspensions were stored at −80° C. Cultures on solid medium were grown on Mueller Hinton II agar (BD), supplemented with 10% OADC and 0.5% glycerol for 10 days at 37° C. with 5% $CO_2$. Antibiotic susceptibility in terms of Minimal Inhibitory Concentration (MIC) according to the guidelines of the Clinical and Laboratory Standards Institutes (CLSI) was 4 mg/L for both omadacycline and tigecycline.

Antimicrobial Drugs

Omadacycline was provided by Paratek Pharmaceuticals (Boston, NY, USA). Tigecycline was purchased from Pfizer (New York, NY, USA).

Time-Kill Kinetics Assay

The concentration- and time-dependent killing capacities of omadacycline and tigecycline were determined as previously described (de Steenwinkel et al., *J. Antimicrob Chemother.,* 2010, 65(12):2582-9; Bax et al., *Antimicrob. Agents Chemother.,* 2016, 60(4):2577-9). Briefly, *M. abscessus* cultures were exposed to antimicrobial drugs at 4-fold increasing concentrations for 7 days at 37° C. under shaking conditions at 96 rpm. In the absence of drugs, the mycobacterial population showed an average increase from $3.6\times10^5$ cfu/mL to $3.5\times10^8$ cfu/mL within 7 days of incubation. The drug concentrations ranged from 0.063 to 256 mg/L for both compounds. The tested concentrations were based on the MIC values of the individual drugs ranging from 1/64×MIC to 64×MIC comprising a broad range for studying in vitro drug activity. At day 1, 3 and 7 during drug exposure, samples were collected, centrifuged at 14000×g to avoid anti-NTM drug carry over, serially diluted (10-fold, $10^0$-$10^7$) and subcultured onto solid medium. Plates were incubated for 10 days at 37° C. with 5% $CO_2$ to determine colony forming units (cfu) counts. The lower limit of detection was 5 cfu/mL (log 0.7). All experiments were performed in duplicate. Time-kill curves, as well as concentration-effect curves were generated.

Selection of Drug-Resistant *M. abscessus*

In order to assess the selection of drug resistant mutants after 7 days of drug exposure, subcultures were also performed on solid media containing omadacycline and tigecycline. The drug concentrations in the subculture plates were 4-fold the MIC concentrations, i.e., 16 mg/L for both tigecycline and omadacycline.

Stability of Antimicrobial Drugs

Antimicrobial activity over time was assessed using the standard large-plate agar diffusion assay as previously described in detail (Bennett et al., Appl. Microbiol. 1966, 14(2):170-7). In short, a *Staphylococcus aureus* strain susceptible to omadacycline and a *Micrococcus luteus* strain susceptible to tigecycline were plated onto solid diagnostic sensitivity test (D.S.T.) agar (Oxoid, Hampshire, UK). A two-fold increasing standard concentration series was prepared. The standard concentration series and two test concentrations of omadacycline and tigecycline were added onto the D.S.T. media and on day 1, 3 and 7 the inhibition zones were determined. Comparing the inhibition zones of the standard concentration series to the zones of the test concentrations enabled determination of the omadacycline and tigecycline concentration over time representing antibiotic stability. A 20% decline in omadacycline concentration was observed within the first 24 hours and it was previously shown that 80% of the tigecycline concentrations declined daily (Bax et al., *Antimicrob. Agents Chemother.,* 2016, 60(4):2577-9). As a compensation, 20% of the omadacycline and 80% of the tigecycline concentrations were added daily.

Results

The concentration- and time-dependent activities of omadacycline and tigecycline are shown in FIG. 1, Panels A and B, respectively. Omadacycline and tigecycline both showed concentration-dependent antimicrobial activity. Omadacycline showed inhibition of mycobacterial growth at 4 mg/L and mycobacterial killing at concentrations ≥16 mg/L, but no elimination was achieved. Tigecycline showed mycobacterial killing at concentrations ≥4 mg/L, achieving elimination at concentrations ≥16 mg/L at day 3-7. No selection of drug resistance above the spontaneous mutation frequency was observed at any of the omadacycline or tigecycline concentrations tested except for a modest 1.5% and 0.6% at omadacycline 4 mg/L and tigecycline 4 mg/L, respectively.

Figure 2:
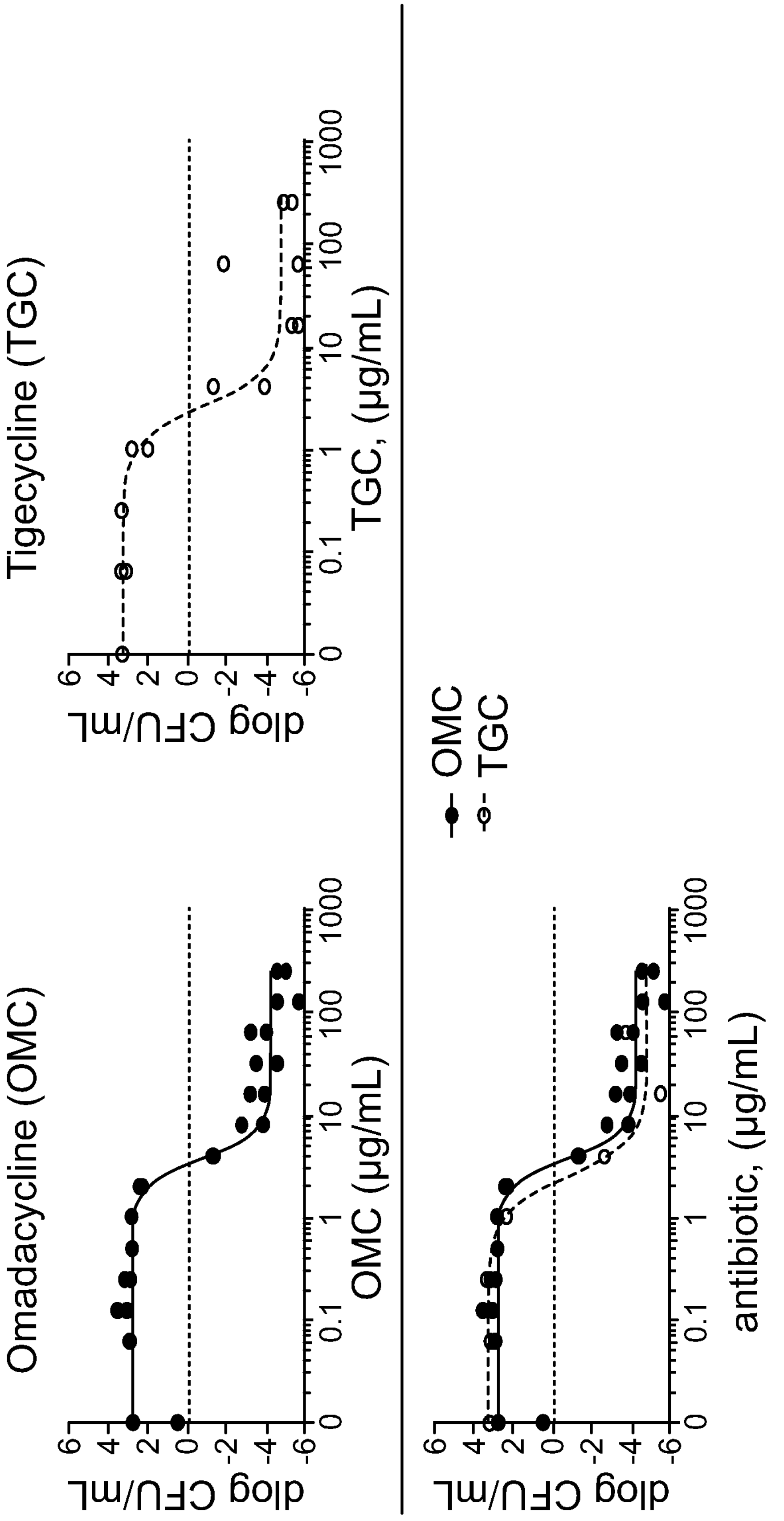
FIG. 2 is a series of graphs showing concentration-effect curves of omadacycline (OMC, top left), tigecycline (TGC, top right) and both omadacycline and tigecycline (OMC and TGC, bottom left) against *M. abscessus* subsp. *abscessus* after 7 days of drug exposure. In the graphs, dlog is the difference between the starting inoculum and the mycobacterial load at day 7.

The concentration-effect relationships after 7 days of exposure are shown in FIG. 2. The concentrations-effect curves showed stasis, 1- and 2 log mycobacterial killing at 3.3, 4.0 and 4.8 mg/L for omadacycline and 2.2, 2.7 and 3.4 mg/L for tigecycline, respectively.

Discussion

This in vitro study showed that omadacycline has good activity against *M. abscessus*, subsp. *abscessus*, which is one of the most difficult to treat species among the NTM. Although the in vitro activity of tigecycline was found to be slightly higher, the clinical relevance of this finding is questionable given the favorable pharmacokinetic properties of omadacycline. Tigecycline has a high protein binding and its free active fraction is, therefore, relatively low compared to that of omadacycline. The 24-hour area under the curve of omadacycline has been shown to be approximately three-fold higher compared to tigecycline in both epithelial lining fluid, alveolar cells and plasma (Gotfried et al., *Antimicrob Agents Chemother.* 2017, 61(9)).

In the study, omadacycline and tigecycline both showed clear concentration-dependent antimicrobial activity. This is in line with the observation in a recent pharmacokinetic/pharmacodynamics study on tigecycline activity against *M. abscessus*. There, doubling the currently used clinical dose was needed for achieving optimal response, indicating also in patients a dose-response effect (Ferro et al., *Antimicrob Agents Chemother.* 2016, 60(5):2895-900). However, in that study the concentrations simulated were based on total tigecycline concentrations and not the free fraction and it is therefore likely that omadacycline is more active in vivo.

Example 3. In Vitro Activity of Tetracycline Compounds Against a *Mycobacterium tuberculosis* Strain The purpose of this study was to test activity of selected tetracycline compounds against the H37Rv strain of *Mycobacterium tuberculosis*. Minimum inhibitory concentrations (MIC) of different tetracycline compounds against H37Rv strain were determined and are shown in Table 8.

TABLE 8
MIC of tetracycline compounds against H37Rv strain of *Mycobacteirum tuberculosis*.
| Compound number | Structure | MIC (μg/mL) |
|---|---|---|
| 1 | 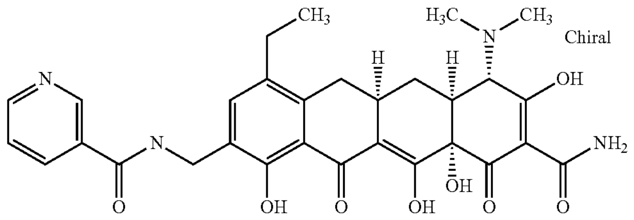 [SMILES: CCc1cc(CNC(=O)c2cccnc2)c(O)c2c1C[C@H]1C[C@H]3[C@H](N(C)C)C(O)=C(C(N)=O)C(=O)[C@@]3(O)C(O)=C1C2=O] | >32 |
| 2 | 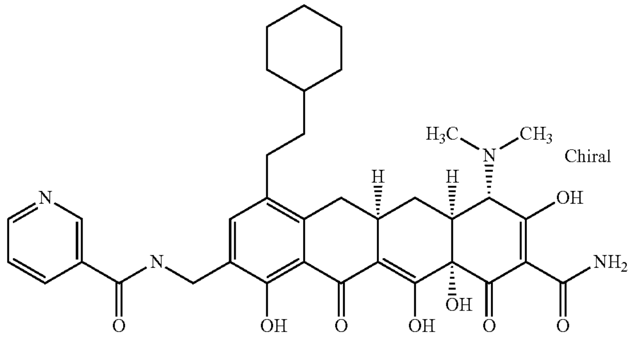 [SMILES: CN(C)[C@@H]1C(O)=C(C(N)=O)C(=O)[C@@]2(O)C(O)=C3C(=O)c4c(O)c(CNC(=O)c5cccnc5)cc(CCC5CCCCC5)c4C[C@H]3C[C@@H]12] | >32 |
| 3 | 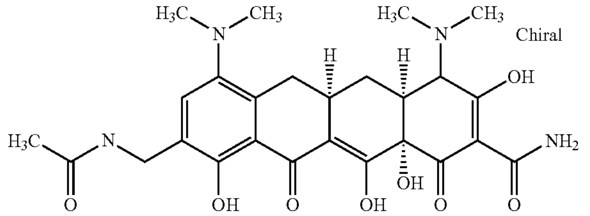 [SMILES: CC(=O)NCc1cc(N(C)C)c2c(c1O)C(=O)C1=C(O)[C@]3(O)C(=O)C(C(N)=O)=C(O)C(N(C)C)[C@@H]3C[C@@H]1C2] | >32 |
| 4 | 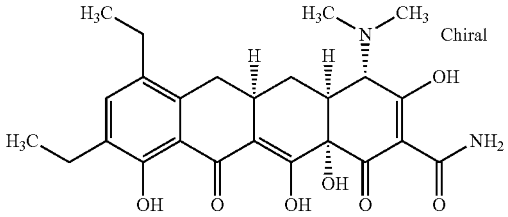 [SMILES: CCc1cc(CC)c2c(c1O)C(=O)C1=C(O)[C@]3(O)C(=O)C(C(N)=O)=C(O)[C@@H](N(C)C)[C@@H]3C[C@@H]1C2] | >32 |
| 5 | 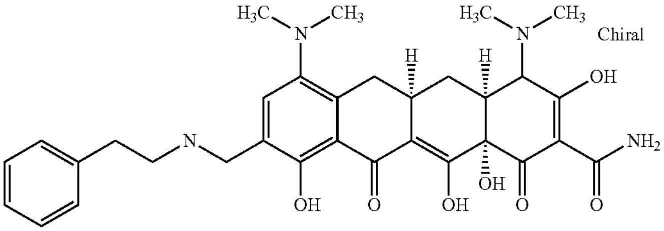 [SMILES: CN(C)c1cc(CNCCc2ccccc2)c(O)c2c1C[C@H]1C[C@H]3C(N(C)C)C(O)=C(C(N)=O)C(=O)[C@@]3(O)C(O)=C1C2=O] | >32 |
| 6 | 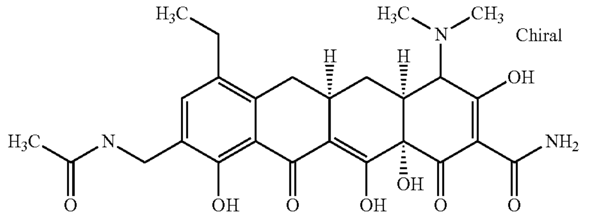 [SMILES: CCc1cc(CNC(C)=O)c(O)c2c1C[C@H]1C[C@H]3C(N(C)C)C(O)=C(C(N)=O)C(=O)[C@@]3(O)C(O)=C1C2=O] | >32 |

TABLE 8-continued
MIC of tetracycline compounds against H37Rv strain of *Mycobacteirum tuberculosis.*
| Compound number | Structure | MIC (μg/mL) |
|---|---|---|
| 8 | 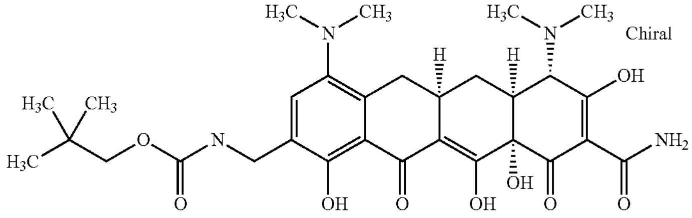 [SMILES: CN(C)c1cc(CNC(=O)OCC(C)(C)C)c(O)c2c1C[C@H]1C[C@H]3[C@H](N(C)C)C(O)=C(C(N)=O)C(=O)[C@@]3(O)C(O)=C1C2=O] | >32 |
| 9 | 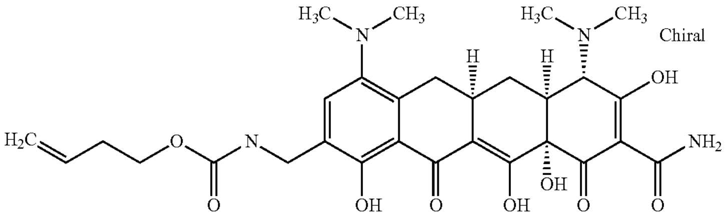 [SMILES: C=CCCOC(=O)NCc1cc(N(C)C)c2c(c1O)C(=O)C1=C(O)[C@]3(O)C(=O)C(C(N)=O)=C(O)[C@@H](N(C)C)[C@@H]3C[C@@H]1C2] | >32<br>>32 |
| 10 | 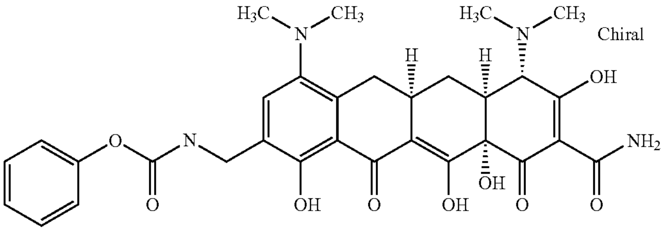 [SMILES: CN(C)c1cc(CNC(=O)Oc2ccccc2)c(O)c2c1C[C@H]1C[C@H]3[C@H](N(C)C)C(O)=C(C(N)=O)C(=O)[C@@]3(O)C(O)=C1C2=O] | >32 |
| 11 | 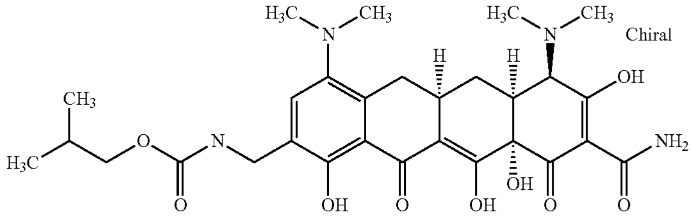 [SMILES: CC(C)COC(=O)NCc1cc(N(C)C)c2c(c1O)C(=O)C1=C(O)[C@]3(O)C(=O)C(C(N)=O)=C(O)[C@H](N(C)C)[C@@H]3C[C@@H]1C2] | >32 |
| 12 | 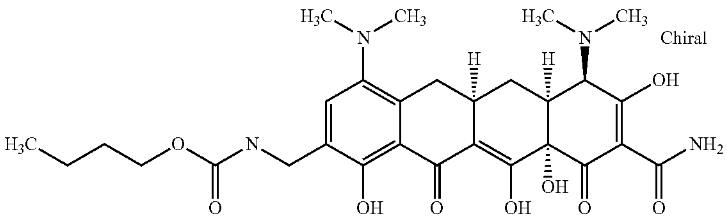 [SMILES: CCCCOC(=O)NCc1cc(N(C)C)c2c(c1O)C(=O)C1=C(O)[C@]3(O)C(=O)C(C(N)=O)=C(O)[C@H](N(C)C)[C@@H]3C[C@@H]1C2] | >32 |
| 13 | 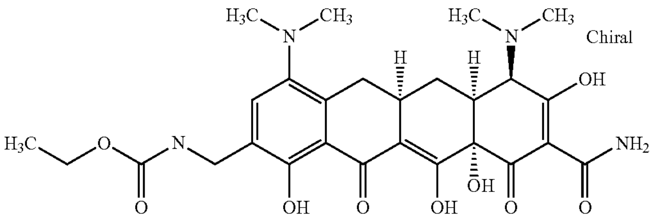 [SMILES: CCOC(=O)NCc1cc(N(C)C)c2c(c1O)C(=O)C1=C(O)[C@]3(O)C(=O)C(C(N)=O)=C(O)[C@H](N(C)C)[C@@H]3C[C@@H]1C2] | 16 |

TABLE 8-continued
MIC of tetracycline compounds against H37Rv strain of *Mycobacteirum tuberculosis*.
| Compound number | Structure | MIC (μg/mL) |
|---|---|---|
| 14 | 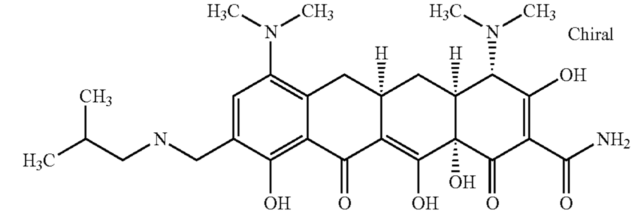 [SMILES: CC(C)CNCc1cc(N(C)C)c2c(c1O)C(=O)C1=C(O)[C@]3(O)C(=O)C(C(N)=O)=C(O)[C@@H](N(C)C)[C@@H]3C[C@@H]1C2] | >32<br>16<br>>32<br>16 |
| 15 | 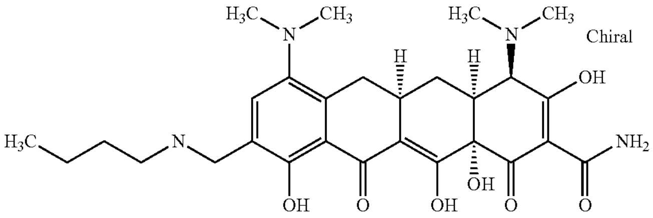 [SMILES: CCCCNCc1cc(N(C)C)c2c(c1O)C(=O)C1=C(O)[C@]3(O)C(=O)C(C(N)=O)=C(O)[C@H](N(C)C)[C@@H]3C[C@@H]1C2] | 32 |
| 16 | 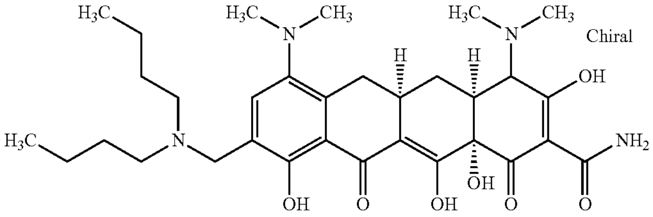 [SMILES: CCCCN(CCCC)Cc1cc(N(C)C)c2c(c1O)C(=O)C1=C(O)[C@]3(O)C(=O)C(C(N)=O)=C(O)C(N(C)C)[C@@H]3C[C@@H]1C2] | >32 |
| 17 | 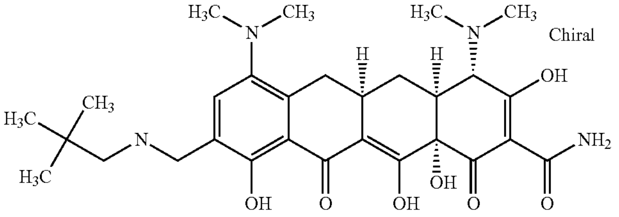 [SMILES: CN(C)c1cc(CNCC(C)(C)C)c(O)c2c1C[C@H]1C[C@H]3[C@H](N(C)C)C(O)=C(C(N)=O)C(=O)[C@@]3(O)C(O)=C1C2=O] | 32 |
| 18 | 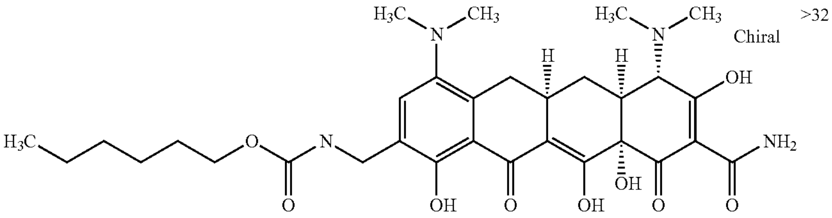 | >32 |
| 19 | 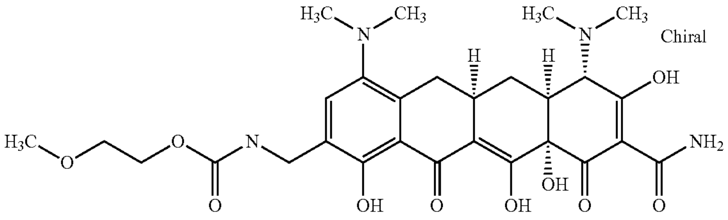 | >32 |

TABLE 8-continued
MIC of tetracycline compounds against H37Rv strain of *Mycobacteirum tuberculosis.*
| Compound number | Structure | MIC (μg/mL) |
|---|---|---|
| 20 | 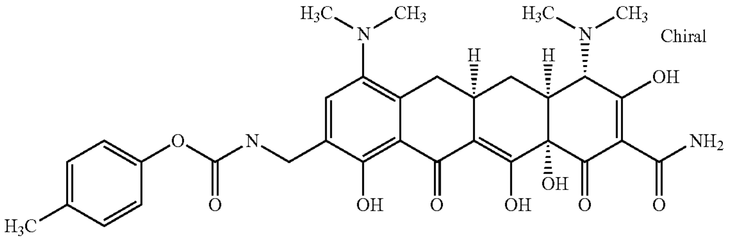 [SMILES: Cc1ccc(OC(=O)NCc2cc(N(C)C)c3c(c2O)C(=O)C2=C(O)[C@]4(O)C(=O)C(C(N)=O)=C(O)[C@@H](N(C)C)[C@@H]4C[C@@H]2C3)cc1] | >32 |
| 21 | 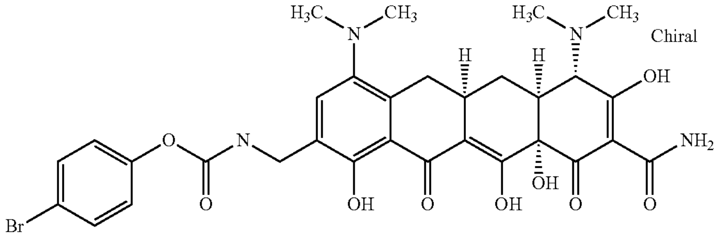 [SMILES: CN(C)c1cc(CNC(=O)Oc2ccc(Br)cc2)c(O)c2c1C[C@H]1C[C@H]3[C@H](N(C)C)C(O)=C(C(N)=O)C(=O)[C@@]3(O)C(O)=C1C2=O] | 16 |
| 22 | 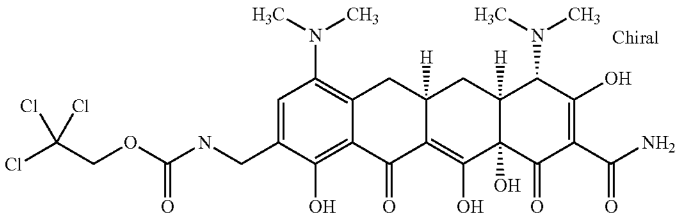 [SMILES: CN(C)c1cc(CNC(=O)OCC(Cl)(Cl)Cl)c(O)c2c1C[C@H]1C[C@H]3[C@H](N(C)C)C(O)=C(C(N)=O)C(=O)[C@@]3(O)C(O)=C1C2=O] | >32 |
| 23 | 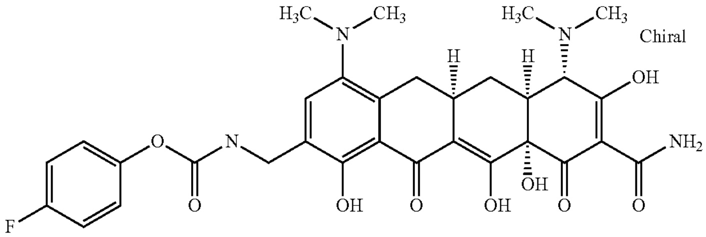 [SMILES: CN(C)c1cc(CNC(=O)Oc2ccc(F)cc2)c(O)c2c1C[C@H]1C[C@H]3[C@H](N(C)C)C(O)=C(C(N)=O)C(=O)[C@@]3(O)C(O)=C1C2=O] | 32 |
| 24 | 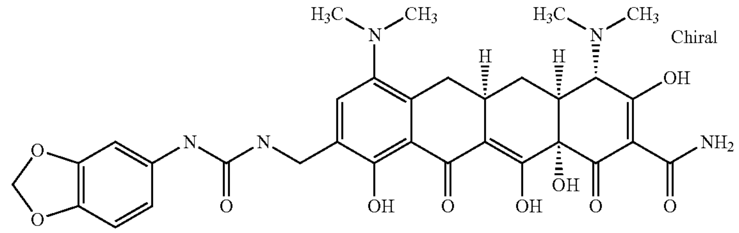 [SMILES: CN(C)c1cc(CNC(=O)Nc2ccc3c(c2)OCO3)c(O)c2c1C[C@H]1C[C@H]3[C@H](N(C)C)C(O)=C(C(N)=O)C(=O)[C@@]3(O)C(O)=C1C2=O] | >32 |
| 25 | 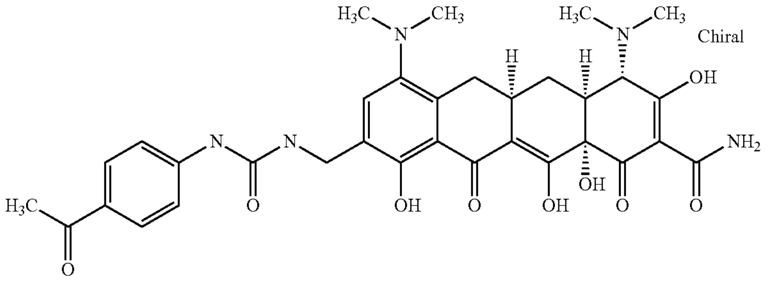 [SMILES: CC(=O)c1ccc(NC(=O)NCc2cc(N(C)C)c3c(c2O)C(=O)C2=C(O)[C@]4(O)C(=O)C(C(N)=O)=C(O)[C@@H](N(C)C)[C@@H]4C[C@@H]2C3)cc1] | >32 |

TABLE 8-continued
| MIC of tetracycline compounds against H37Rv strain of *Mycobacteirum tuberculosis*. | | |
|---|---|---|
| Compound number | Structure | MIC (μg/mL) |
| 26 | 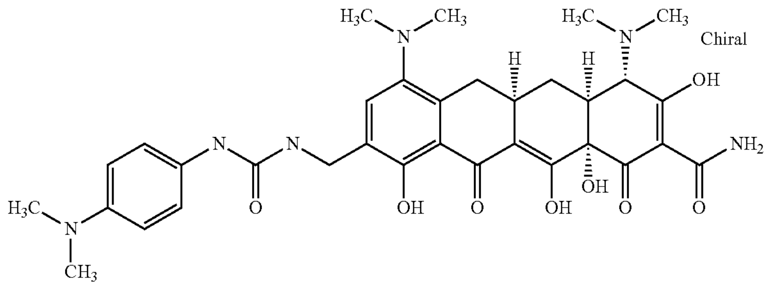 [SMILES: CN(C)c1ccc(NC(=O)NCc2cc(N(C)C)c3c(c2O)C(=O)C2=C(O)[C@]4(O)C(=O)C(C(N)=O)=C(O)[C@@H](N(C)C)[C@@H]4C[C@@H]2C3)cc1] | 32 |
| 27 | 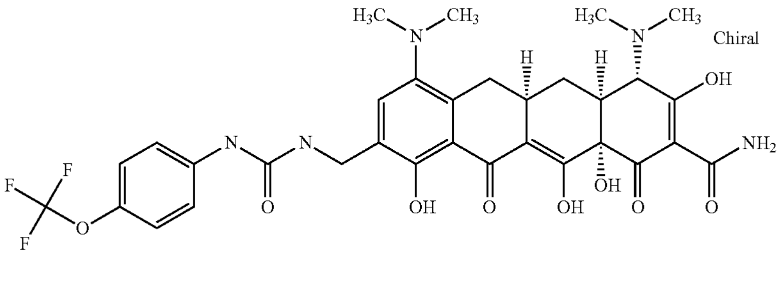 [SMILES: CN(C)c1cc(CNC(=O)Nc2ccc(OC(F)(F)F)cc2)c(O)c2c1C[C@H]1C[C@H]3[C@H](N(C)C)C(O)=C(C(N)=O)C(=O)[C@@]3(O)C(O)=C1C2=O] | 8 |
| 28 | 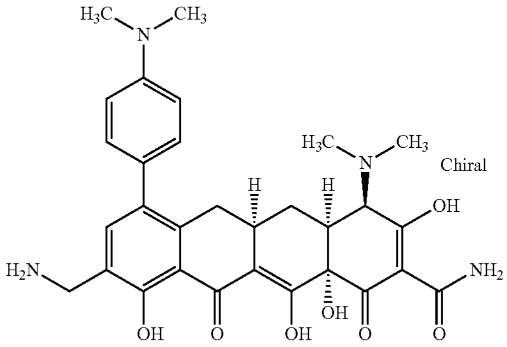 [SMILES: CN(C)c1ccc(-c2cc(CN)c(O)c3c2C[C@H]2C[C@H]4[C@@H](N(C)C)C(O)=C(C(N)=O)C(=O)[C@@]4(O)C(O)=C2C3=O)cc1] | >32 |
| 29 | 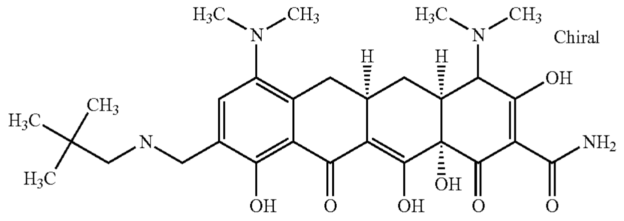 | 32<br>32<br>32 |
| 30 | 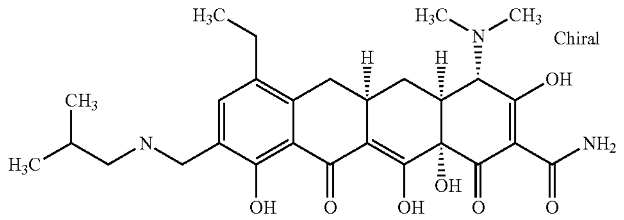 [SMILES: CCc1cc(CNCC(C)C)c(O)c2c1C[C@H]1C[C@H]3[C@H](N(C)C)C(O)=C(C(N)=O)C(=O)[C@@]3(O)C(O)=C1C2=O] | >32 |

TABLE 8-continued
MIC of tetracycline compounds against H37Rv strain of *Mycobacteirum tuberculosis*.
| Compound number | Structure | MIC (μg/mL) |
| --- | --- | --- |
| 31 | 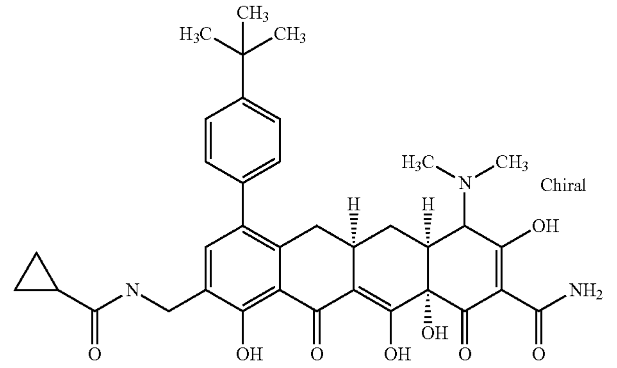 [SMILES: CN(C)C1C(O)=C(C(N)=O)C(=O)[C@@]2(O)C(O)=C3C(=O)c4c(O)c(CNC(=O)C5CC5)cc(-c5ccc(C(C)(C)C)cc5)c4C[C@H]3C[C@@H]12] | >32 |
| 32 | 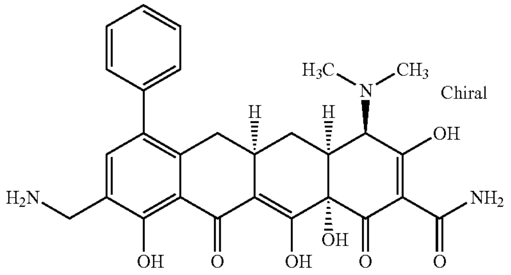 [SMILES: CN(C)[C@H]1C(O)=C(C(N)=O)C(=O)[C@@]2(O)C(O)=C3C(=O)c4c(O)c(CN)cc(-c5ccccc5)c4C[C@H]3C[C@@H]12] | >32 |
| 33 | 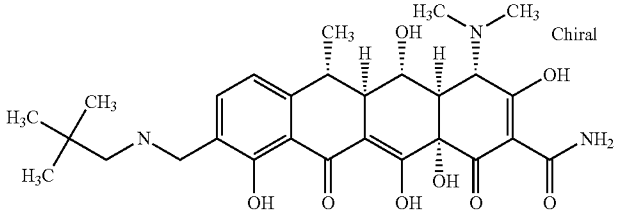 [SMILES: C[C@H]1c2ccc(CNCC(C)(C)C)c(O)c2C(=O)C2=C(O)[C@]3(O)C(=O)C(C(N)=O)=C(O)[C@@H](N(C)C)[C@@H]3[C@@H](O)[C@@H]21] | >32 |
| 34 | 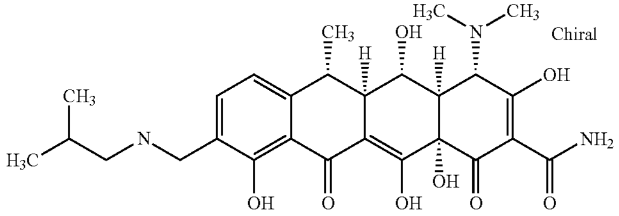 [SMILES: CC(C)CNCc1ccc2c(c1O)C(=O)C1=C(O)[C@]3(O)C(=O)C(C(N)=O)=C(O)[C@@H](N(C)C)[C@@H]3[C@@H](O)[C@@H]1[C@H]2C] | 32 |
| 35 | 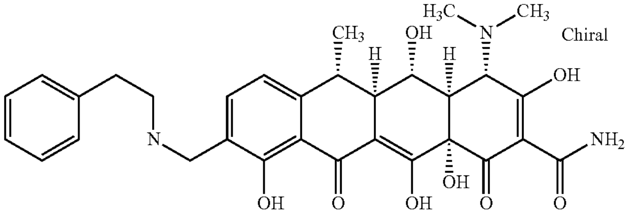 [SMILES: C[C@H]1c2ccc(CNCCc3ccccc3)c(O)c2C(=O)C2=C(O)[C@]3(O)C(=O)C(C(N)=O)=C(O)[C@@H](N(C)C)[C@@H]3[C@@H](O)[C@@H]21] | >32 |
| 36 | 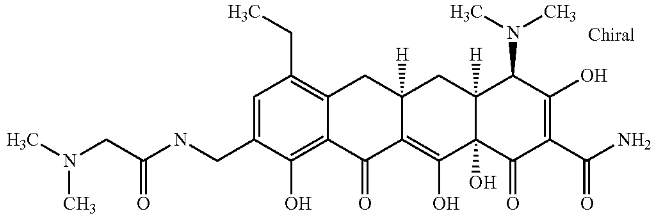 [SMILES: CCc1cc(CNC(=O)CN(C)C)c(O)c2c1C[C@H]1C[C@H]3[C@@H](N(C)C)C(O)=C(C(N)=O)C(=O)[C@@]3(O)C(O)=C1C2=O] | 32 |

TABLE 8-continued
MIC of tetracycline compounds against H37Rv strain of *Mycobacteirum tuberculosis*.
| Compound number | Structure | MIC (μg/mL) |
| --- | --- | --- |
| 37 | 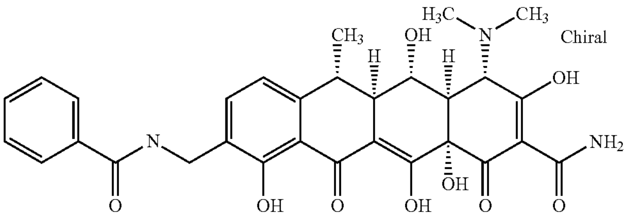 [SMILES: C[C@H]1c2ccc(CNC(=O)c3ccccc3)c(O)c2C(=O)C2=C(O)[C@]3(O)C(=O)C(C(N)=O)=C(O)[C@@H](N(C)C)[C@@H]3[C@@H](O)[C@@H]21] | >32 |
| 38 | 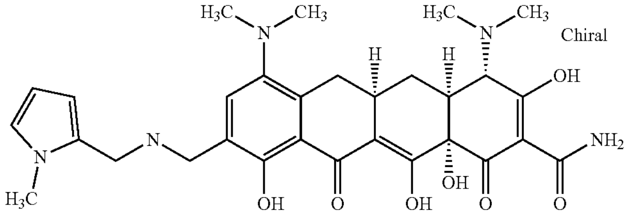 [SMILES: CN(C)c1cc(CNCc2cccn2C)c(O)c2c1C[C@H]1C[C@H]3[C@H](N(C)C)C(O)=C(C(N)=O)C(=O)[C@@]3(O)C(O)=C1C2=O] | >32 |
| 39 | 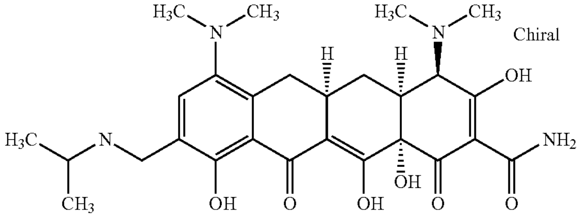 [SMILES: CC(C)NCc1cc(N(C)C)c2c(c1O)C(=O)C1=C(O)[C@]3(O)C(=O)C(C(N)=O)=C(O)[C@H](N(C)C)[C@@H]3C[C@@H]1C2] | >32 |
| 40 | 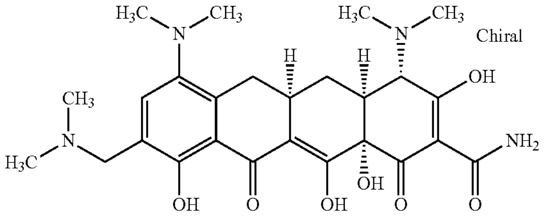 [SMILES: CN(C)Cc1cc(N(C)C)c2c(c1O)C(=O)C1=C(O)[C@]3(O)C(=O)C(C(N)=O)=C(O)[C@@H](N(C)C)[C@@H]3C[C@@H]1C2] | 32<br>32 |
| 41 | 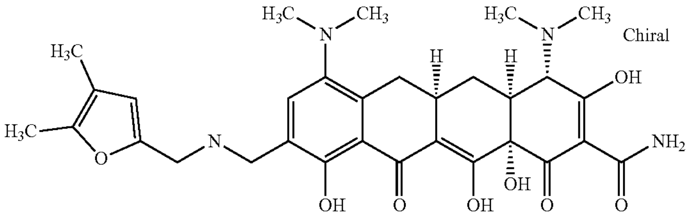 [SMILES: Cc1cc(CNCc2cc(N(C)C)c3c(c2O)C(=O)C2=C(O)[C@]4(O)C(=O)C(C(N)=O)=C(O)[C@@H](N(C)C)[C@@H]4C[C@@H]2C3)oc1C] | >32<br>>32 |
| 42 | 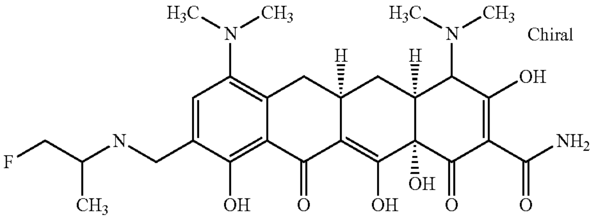 [SMILES: CC(CF)NCc1cc(N(C)C)c2c(c1O)C(=O)C1=C(O)[C@]3(O)C(=O)C(C(N)=O)=C(O)C(N(C)C)[C@@H]3C[C@@H]1C2] | 32<br>32 |

TABLE 8-continued
MIC of tetracycline compounds against H37Rv strain of *Mycobacteirum tuberculosis*.
| Compound number | Structure | MIC (μg/mL) |
|---|---|---|
| 43 | 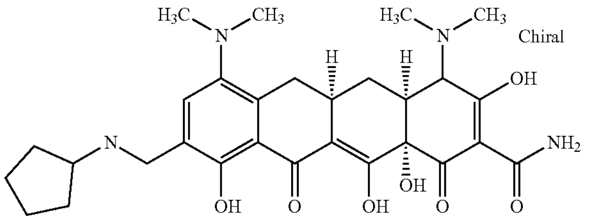 [SMILES: CN(C)c1cc(CNC2CCCC2)c(O)c2c1C[C@H]1C[C@H]3C(N(C)C)C(O)=C(C(N)=O)C(=O)[C@@]3(O)C(O)=C1C2=O] | >32<br>>32 |
| 44 | 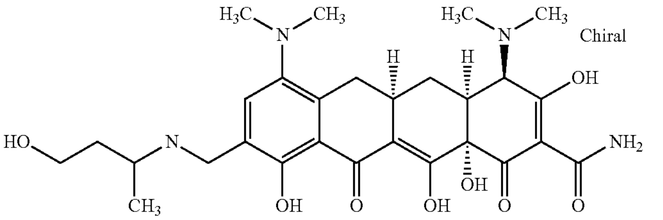 [SMILES: CC(CCO)NCc1cc(N(C)C)c2c(c1O)C(=O)C1=C(O)[C@]3(O)C(=O)C(C(N)=O)=C(O)[C@H](N(C)C)[C@@H]3C[C@@H]1C2] | >32<br>>32 |
| 45 | 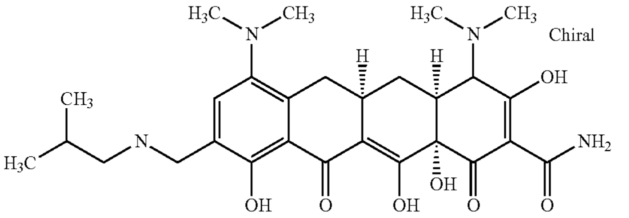 [SMILES: CC(C)CNCc1cc(N(C)C)c2c(c1O)C(=O)C1=C(O)[C@]3(O)C(=O)C(C(N)=O)=C(O)C(N(C)C)[C@@H]3C[C@@H]1C2] | 32<br>32 |
| 46 | 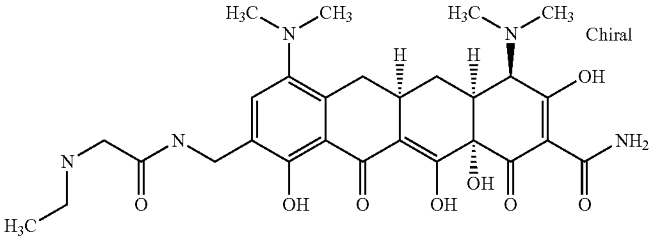 [SMILES: CCNCC(=O)NCc1cc(N(C)C)c2c(c1O)C(=O)C1=C(O)[C@]3(O)C(=O)C(C(N)=O)=C(O)[C@H](N(C)C)[C@@H]3C[C@@H]1C2] | 32<br>32 |
| 47 | 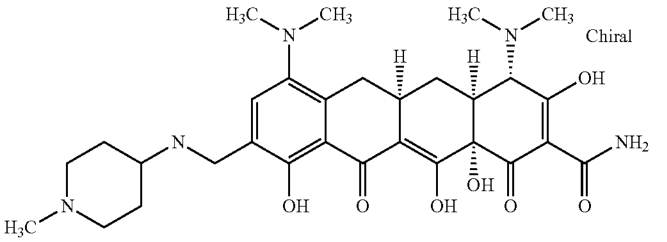 [SMILES: CN1CCC(NCc2cc(N(C)C)c3c(c2O)C(=O)C2=C(O)[C@]4(O)C(=O)C(C(N)=O)=C(O)[C@@H](N(C)C)[C@@H]4C[C@@H]2C3)CC1] | >32<br>>32 |
| 48 | 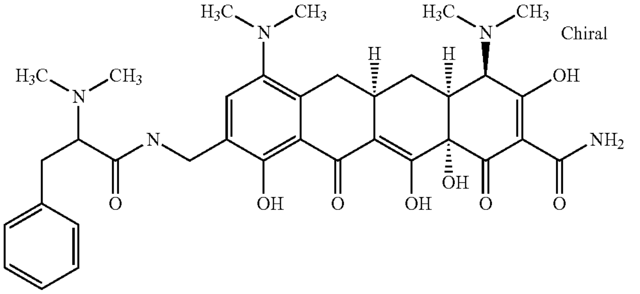 [SMILES: CN(C)c1cc(CNC(=O)C(Cc2ccccc2)N(C)C)c(O)c2c1C[C@H]1C[C@H]3[C@@H](N(C)C)C(O)=C(C(N)=O)C(=O)[C@@]3(O)C(O)=C1C2=O] | >32<br>>32 |

TABLE 8-continued
MIC of tetracycline compounds against H37Rv strain of *Mycobacteirum tuberculosis*.
| Compound number | Structure | MIC (μg/mL) |
| --- | --- | --- |
| 49 | 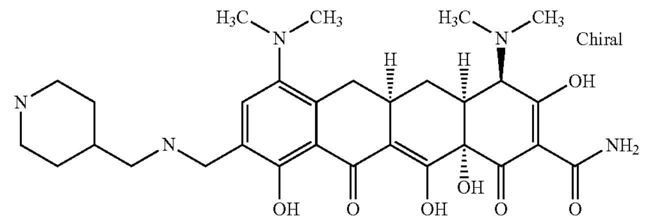 [SMILES: CN(C)c1cc(CNCC2CCNCC2)c(O)c2c1C[C@H]1C[C@H]3[C@@H](N(C)C)C(O)=C(C(N)=O)C(=O)[C@@]3(O)C(O)=C1C2=O] | >32<br>>32 |
| 50 | 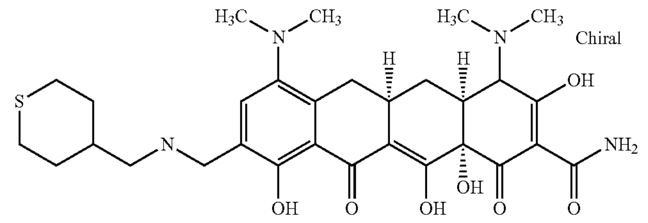 [SMILES: CN(C)c1cc(CNCC2CCSCC2)c(O)c2c1C[C@H]1C[C@H]3C(N(C)C)C(O)=C(C(N)=O)C(=O)[C@@]3(O)C(O)=C1C2=O] | >32<br>>32 |
| 51 | 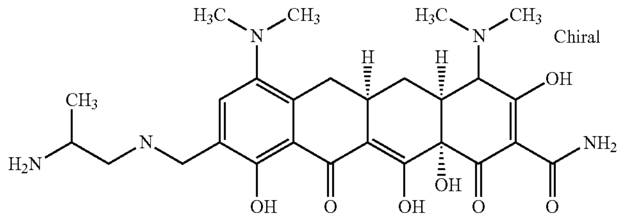 | >32<br>>32 |
| 52 | 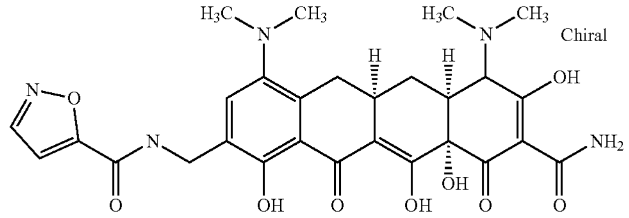 [SMILES: CN(C)c1cc(CNC(=O)c2ccno2)c(O)c2c1C[C@H]1C[C@H]3C(N(C)C)C(O)=C(C(N)=O)C(=O)[C@@]3(O)C(O)=C1C2=O] | 16<br>16 |
| 53 | 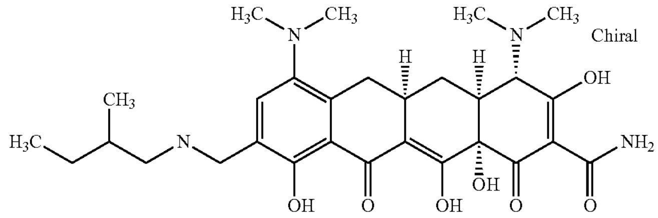 [SMILES: CCC(C)CNCc1cc(N(C)C)c2c(c1O)C(=O)C1=C(O)[C@]3(O)C(=O)C(C(N)=O)=C(O)[C@@H](N(C)C)[C@@H]3C[C@@H]1C2] | 16<br>16 |
| 54 | 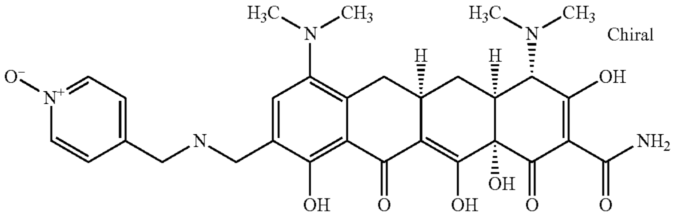 [SMILES: CN(C)c1cc(CNCc2cc[n+]([O-])cc2)c(O)c2c1C[C@H]1C[C@H]3[C@H](N(C)C)C(O)=C(C(N)=O)C(=O)[C@@]3(O)C(O)=C1C2=O] | 32<br>32 |

TABLE 8-continued
MIC of tetracycline compounds against H37Rv strain of *Mycobacteirum tuberculosis.*
| Compound number | Structure | MIC (μg/mL) |
| --- | --- | --- |
| 55 | 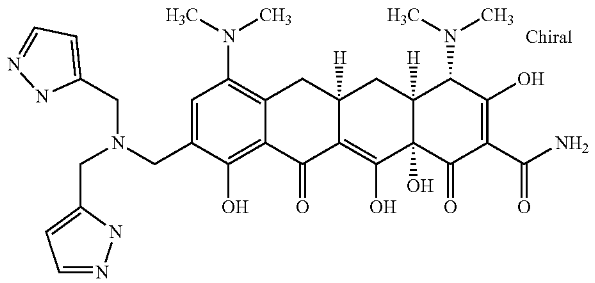 [SMILES: CN(C)c1cc(CN(Cc2ccn[nH]2)Cc2ccn[nH]2)c(O)c2c1C[C@H]1C[C@H]3[C@H](N(C)C)C(O)=C(C(N)=O)C(=O)[C@@]3(O)C(O)=C1C2=O] | >32<br>>32 |
| 56 | 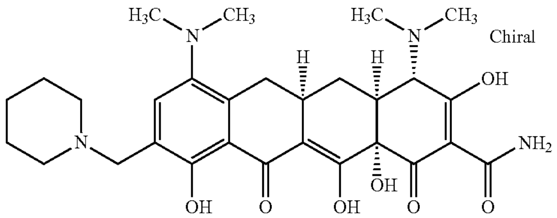 [SMILES: CN(C)c1cc(CN2CCCCC2)c(O)c2c1C[C@H]1C[C@H]3[C@H](N(C)C)C(O)=C(C(N)=O)C(=O)[C@@]3(O)C(O)=C1C2=O] | 16<br>16 |
| 57 | 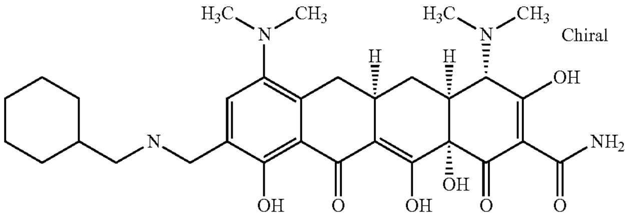 [SMILES: CN(C)c1cc(CNCC2CCCCC2)c(O)c2c1C[C@H]1C[C@H]3[C@H](N(C)C)C(O)=C(C(N)=O)C(=O)[C@@]3(O)C(O)=C1C2=O] | 32<br>32 |
| 58 | 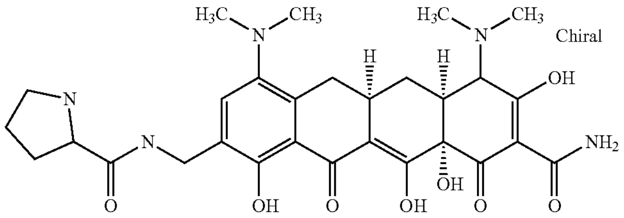 [SMILES: CN(C)c1cc(CNC(=O)C2CCCN2)c(O)c2c1C[C@H]1C[C@H]3C(N(C)C)C(O)=C(C(N)=O)C(=O)[C@@]3(O)C(O)=C1C2=O] | 16<br>16 |
| 59 | 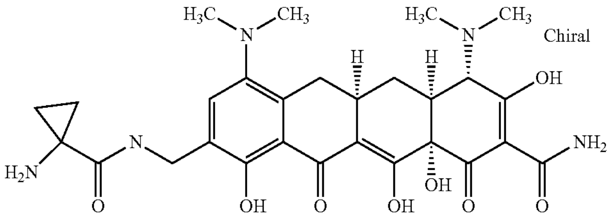 [SMILES: CN(C)c1cc(CNC(=O)C2(N)CC2)c(O)c2c1C[C@H]1C[C@H]3[C@H](N(C)C)C(O)=C(C(N)=O)C(=O)[C@@]3(O)C(O)=C1C2=O] | 16<br>16 |
| 60 | 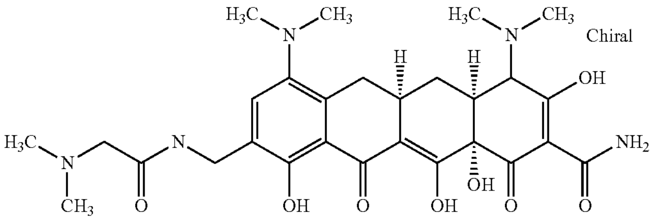 [SMILES: CN(C)CC(=O)NCc1cc(N(C)C)c2c(c1O)C(=O)C1=C(O)[C@]3(O)C(=O)C(C(N)=O)=C(O)C(N(C)C)[C@@H]3C[C@@H]1C2] | 16<br>16 |

TABLE 8-continued
MIC of tetracycline compounds against H37Rv strain of *Mycobacteirum tuberculosis*.
| Compound number | Structure | MIC (μg/mL) |
| --- | --- | --- |
| 61 | 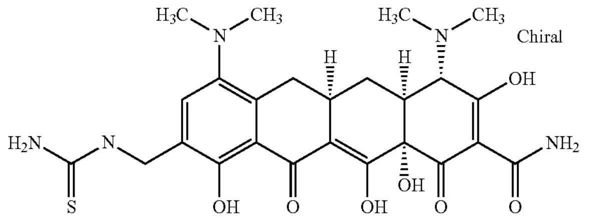 | >32<br>>32 |
| 62 | 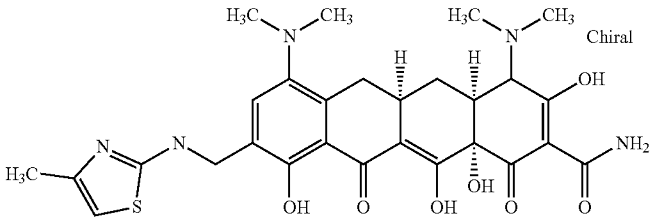 [SMILES: Cc1csc(NCc2cc(N(C)C)c3c(c2O)C(=O)C2=C(O)[C@]4(O)C(=O)C(C(N)=O)=C(O)C(N(C)C)[C@@H]4C[C@@H]2C3)n1] | >32<br>>32 |
| 63 | 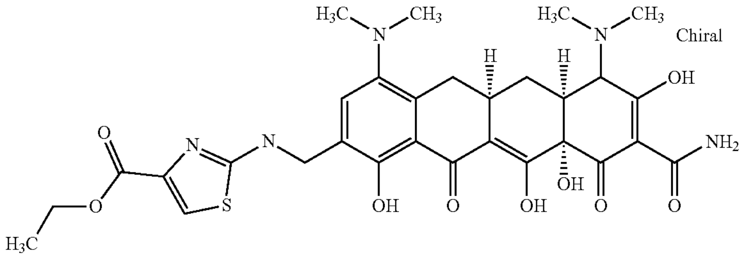 [SMILES: CCOC(=O)c1csc(NCc2cc(N(C)C)c3c(c2O)C(=O)C2=C(O)[C@]4(O)C(=O)C(C(N)=O)=C(O)C(N(C)C)[C@@H]4C[C@@H]2C3)n1] | >32<br>>32 |
| 64 | 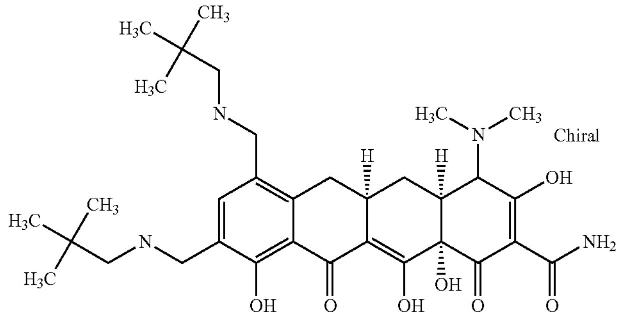 [SMILES: CN(C)C1C(O)=C(C(N)=O)C(=O)[C@@]2(O)C(O)=C3C(=O)c4c(O)c(CNCC(C)(C)C)cc(CNCC(C)(C)C)c4C[C@H]3C[C@@H]12] | 32<br>32 |
| 65 | 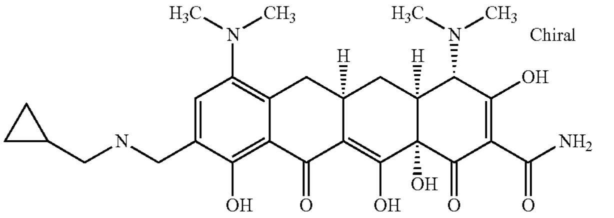 [SMILES: CN(C)c1cc(CNCC2CC2)c(O)c2c1C[C@H]1C[C@H]3[C@H](N(C)C)C(O)=C(C(N)=O)C(=O)[C@@]3(O)C(O)=C1C2=O] | 16<br>16 |
| 66 | 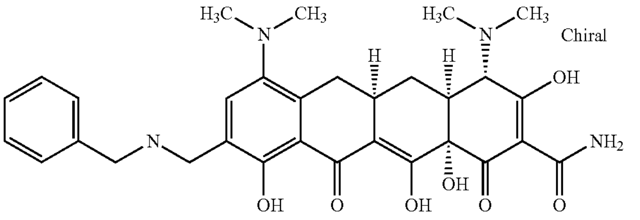 [SMILES: CN(C)c1cc(CNCc2ccccc2)c(O)c2c1C[C@H]1C[C@H]3[C@H](N(C)C)C(O)=C(C(N)=O)C(=O)[C@@]3(O)C(O)=C1C2=O] | >32<br>>32 |

TABLE 8-continued
MIC of tetracycline compounds against H37Rv strain of *Mycobacteirum tuberculosis*.
| Compound number | Structure | MIC (μg/mL) |
|---|---|---|
| 67 | 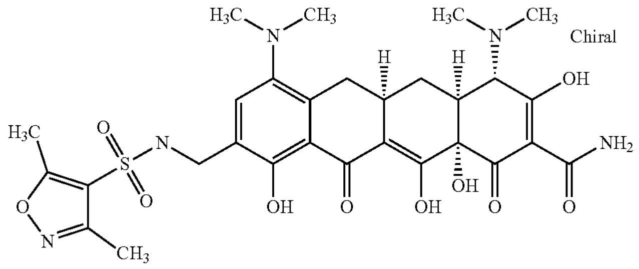 [SMILES: Cc1noc(C)c1S(=O)(=O)NCc1cc(N(C)C)c2c(c1O)C(=O)C1=C(O)[C@]3(O)C(=O)C(C(N)=O)=C(O)[C@@H](N(C)C)[C@@H]3C[C@@H]1C2] | >32<br>>32 |
| 68 | 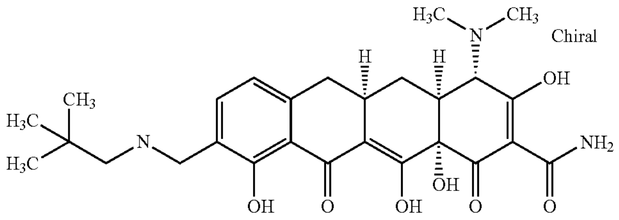 [SMILES: CN(C)[C@@H]1C(O)=C(C(N)=O)C(=O)[C@@]2(O)C(O)=C3C(=O)c4c(ccc(CNCC(C)(C)C)c4O)C[C@H]3C[C@@H]12] | >32<br>32 |
| 69 | 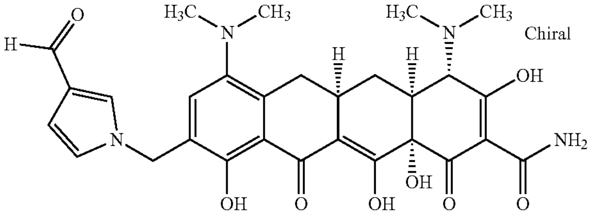 [SMILES: CN(C)c1cc(Cn2ccc(C=O)c2)c(O)c2c1C[C@H]1C[C@H]3[C@H](N(C)C)C(O)=C(C(N)=O)C(=O)[C@@]3(O)C(O)=C1C2=O] | >32<br>>32 |
| 70 | 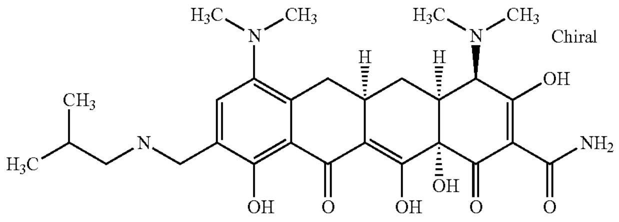 [SMILES: CC(C)CNCc1cc(N(C)C)c2c(c1O)C(=O)C1=C(O)[C@]3(O)C(=O)C(C(N)=O)=C(O)[C@H](N(C)C)[C@@H]3C[C@@H]1C2] | 16<br>16 |
| 71 | 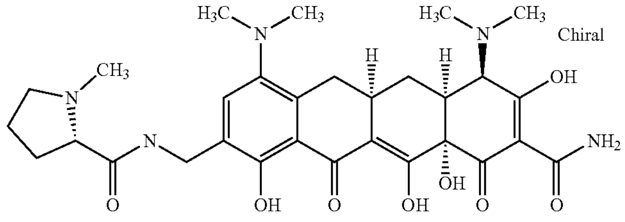 [SMILES: CN(C)c1cc(CNC(=O)[C@@H]2CCCN2C)c(O)c2c1C[C@H]1C[C@H]3[C@@H](N(C)C)C(O)=C(C(N)=O)C(=O)[C@@]3(O)C(O)=C1C2=O] | 16<br>16 |
| 72 | 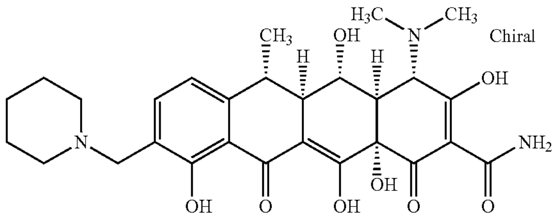 [SMILES: C[C@H]1c2ccc(CN3CCCCC3)c(O)c2C(=O)C2=C(O)[C@]3(O)C(=O)C(C(N)=O)=C(O)[C@@H](N(C)C)[C@@H]3[C@@H](O)[C@@H]21] | 32<br>32 |

TABLE 8-continued
MIC of tetracycline compounds against H37Rv strain of *Mycobacteirum tuberculosis.*
| Compound number | Structure | MIC (μg/mL) |
|---|---|---|
| 73 | 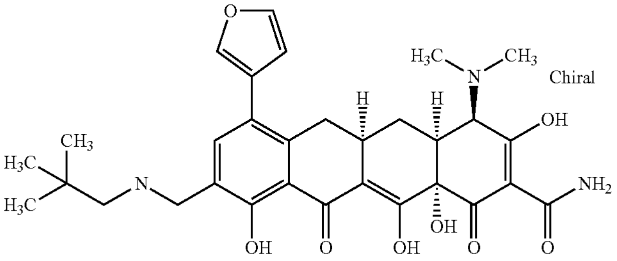 [SMILES: CN(C)[C@H]1C(O)=C(C(N)=O)C(=O)[C@@]2(O)C(O)=C3C(=O)c4c(O)c(CNCC(C)(C)C)cc(-c5ccoc5)c4C[C@H]3C[C@@H]12] | >32<br>>32 |
| 74 | 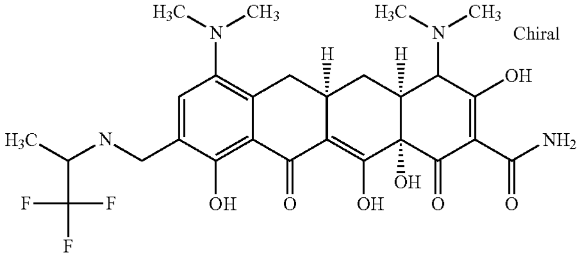 [SMILES: CC(NCc1cc(N(C)C)c2c(c1O)C(=O)C1=C(O)[C@]3(O)C(=O)C(C(N)=O)=C(O)C(N(C)C)[C@@H]3C[C@@H]1C2)C(F)(F)F] | >32<br>>32 |
| 75 | 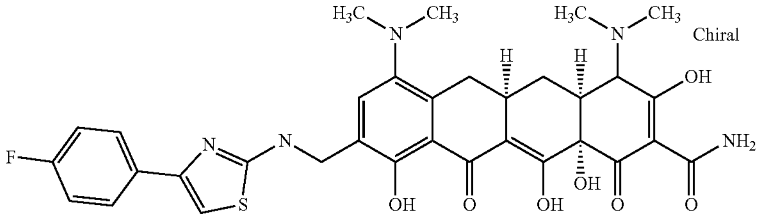 [SMILES: CN(C)c1cc(CNc2nc(-c3ccc(F)cc3)cs2)c(O)c2c1C[C@H]1C[C@H]3C(N(C)C)C(O)=C(C(N)=O)C(=O)[C@@]3(O)C(O)=C1C2=O] | >32<br>>32 |
| 76 | 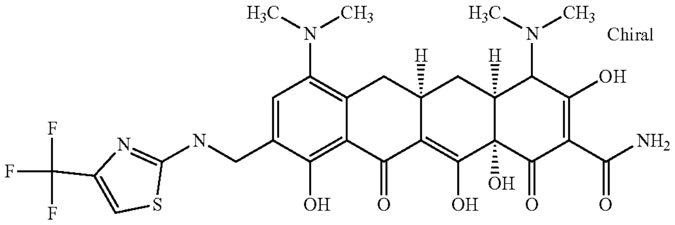 [SMILES: CN(C)c1cc(CNc2nc(C(F)(F)F)cs2)c(O)c2c1C[C@H]1C[C@H]3C(N(C)C)C(O)=C(C(N)=O)C(=O)[C@@]3(O)C(O)=C1C2=O] | >32<br>>32 |
| 77 | 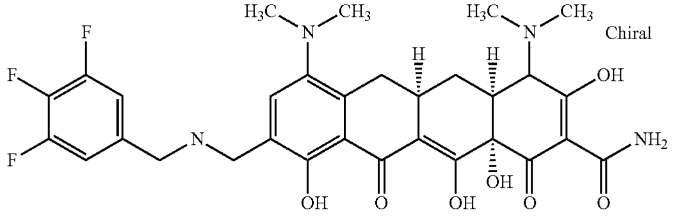 [SMILES: CN(C)c1cc(CNCc2cc(F)c(F)c(F)c2)c(O)c2c1C[C@H]1C[C@H]3C(N(C)C)C(O)=C(C(N)=O)C(=O)[C@@]3(O)C(O)=C1C2=O] | >32<br>>32 |
| 78 | 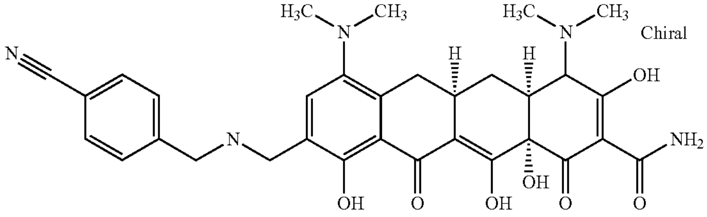 [SMILES: CN(C)c1cc(CNCc2ccc(C#N)cc2)c(O)c2c1C[C@H]1C[C@H]3C(N(C)C)C(O)=C(C(N)=O)C(=O)[C@@]3(O)C(O)=C1C2=O] | 32<br>32 |

TABLE 8-continued

MIC of tetracycline compounds against H37Rv strain of *Mycobacteirum tuberculosis*.

| Compound number | Structure | MIC (μg/mL) |
|---|---|---|
| 79 | 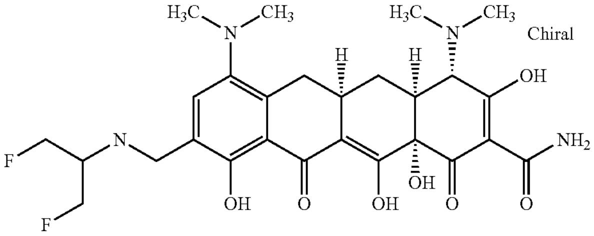 [SMILES: CN(C)c1cc(CNC(CF)CF)c(O)c2c1C[C@H]1C[C@H]3[C@H](N(C)C)C(O)=C(C(N)=O)C(=O)[C@@]3(O)C(O)=C1C2=O] | 32<br>32 |
| 80 | 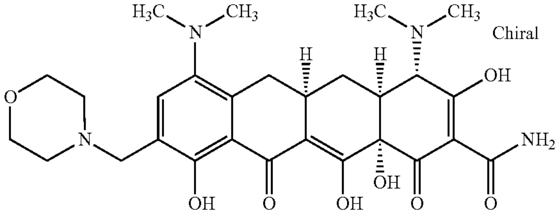 [SMILES: CN(C)c1cc(CN2CCOCC2)c(O)c2c1C[C@H]1C[C@H]3[C@H](N(C)C)C(O)=C(C(N)=O)C(=O)[C@@]3(O)C(O)=C1C2=O] | 16<br>16 |
| 81 | 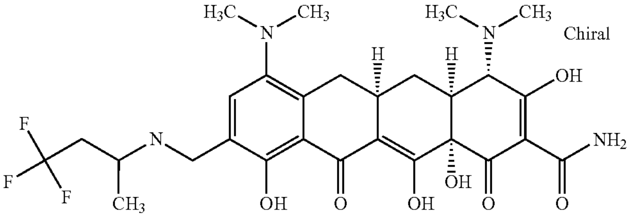 [SMILES: CC(CC(F)(F)F)NCc1cc(N(C)C)c2c(c1O)C(=O)C1=C(O)[C@]3(O)C(=O)C(C(N)=O)=C(O)[C@@H](N(C)C)[C@@H]3C[C@@H]1C2] | 32<br>32 |
| 82 | 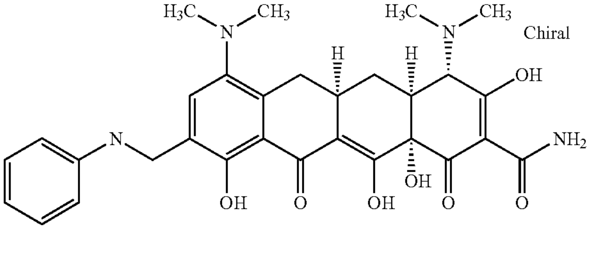 [SMILES: CN(C)c1cc(CNc2ccccc2)c(O)c2c1C[C@H]1C[C@H]3[C@H](N(C)C)C(O)=C(C(N)=O)C(=O)[C@@]3(O)C(O)=C1C2=O] | >32<br>>32 |
| 83 | 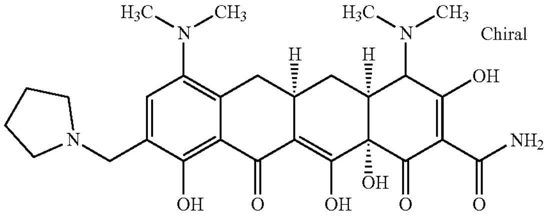 [SMILES: CN(C)c1cc(CN2CCCC2)c(O)c2c1C[C@H]1C[C@H]3C(N(C)C)C(O)=C(C(N)=O)C(=O)[C@@]3(O)C(O)=C1C2=O] | 32<br>32 |

The results presented in Table 8 indicate that certain tetracycline compounds can inhibit growth of the H37Rv strain of *Mycobacterium tuberculosis*.

Example 4. In Vitro Activity of Omadacycline in Combination with Linezolid or Clarithromycin Against BCG The purpose of this study was to evaluate the in vitro activity of omadacycline (OMC) in combination with either linezolid (LZD) or clarithromycin (CLA) against Bacille Calmette Guerin (BCG). BCG is an attenuated version of *Mycobacterium bovis*, which is a species that is closely related to *Mycobacterium tuberculosis*.

Methods

The in vitro activity of omadacycline in combination with linezolid or clarithromycin was evaluated using disk diffusion assay. The BCG cell suspension at a density of 3 McFarland units was plated on agar plates, and antibiotic-containing disks were also added. The antibiotic-containing disks contained antibiotics as follows: 15 μg of omadacycline; 15 μg of clarithromycin; 30 μg of linezolid; a combination of 15 μg of clarithromycin and 15 μg of omadacycline; a combination of 30 μg of linezolid and 15 μg of omadacycline; and a combination of 5 μg of linezolid and 5 μg of omadacycline. The plates were incubated at 37° C. in ambient air for about one month. Subsequently, the plates were evaluated for bacterial growth.

Results

The results of the disk diffusion assay is shown in Table 9 below.

TABLE 9

Results of disk diffusion assay.

| Antibiotic | Results/Observations |
|---|---|
| 15 µg of omadacycline | Markedly decreased growth around disk and clear zone |
| 15 µg of clarithromycin | 45 mm clear zone |
| 30 µg of linezolid | No growth on plate |
| 15 µg of clarithromycin<br>15 µg of omadacycline | ~55 mm clear zone; little growth at periphery |
| 30 µg of linezolid<br>15 µg of omadacycline | ~55 mm clear zone; little growth at periphery |
| 5 µg of linezolid<br>5 µg of omadacycline | 45 mm clear zone |

Conclusions

The results presented in Table 9 indicate that omadacycline has promising activity against BCG, either alone or in combination with clarithromycin or linezolid. Based on this results, it is also expected that omadacycline will have activity against *Mycobacterium tuberculosis.*

Example 5. An Open-Label, Parallel Group, Multiple IV Dose Study to Assess Intra-Pulmonary Steady-State Concentrations of Omadacycline and Tigecycline in Healthy Adult Subjects Introduction To be effective in treating respiratory infections, an antibiotic, when administered, must attain adequate concentrations in respiratory tissues to affect respiratory pathogens. The pathogens causing the infections may be extracellular or intracellular, and, therefore, both extracellular and intracellular concentrations of the antibiotic must be adequate in order for the antibiotic to be active against the extracellular and intracellular pathogens in vivo. The concentration of antibiotic in bronchial mucosa provides a reliable guide to bronchial penetration of the antibiotic and may be a better predictor of clinical efficacy than serum levels.

Epithelial lining fluid (ELF) and alveolar cells (AC), including mostly alveolar macrophages (AM), are important infection sites for common extracellular and intracellular pathogens, respectively. For example, it is known that mycobacteria infecting the lungs, such as *M. tuberculosis* or NTM, may persist as intracellular infection within macrophages. It is also known that mycobacteria, such as NTM, may persist extracellularly as biofilms.

Direct measurement of the concentration of antimicrobial agents in the ELF allows to determine appropriate dosing of an antibiotic, and to evaluate the pharmacokinetic (PK) and exposure-response targets of the drug for respiratory infections. Bronchoalveolar lavage (BAL) that involves collecting respiratory tract fluid and tissue has become a standard method of ascertaining both extracellular and intracellular antibiotic concentrations after systemic administration of the antibiotic. Extracellular concentrations are calculated from fluid reflecting ELF, and intracellular concentrations are measured in ACs, including macrophages.

It was previously shown that the in vitro activity of omadacycline was not affected by serum or lung surfactant, an important characteristic that is consistent with potential utility of omadacycline in treating respiratory infections. Further, omadacycline has been shown to be effective in treating mouse models of respiratory infections. In mice, omadacycline concentrations in lung tissue exceed plasma concentrations by 3.7 to 4.4 fold. In vitro results against intracellular bacteria and tissue culture experiments indicate that omadacycline concentrates within mammalian cells.

The purpose of the study was to determine the concentration of omadacycline in pulmonary compartments (ELF and in pulmonary ACs, including AMs) and define time course of pulmonary distribution in comparison with the plasma pharmacokinetic (PK) profile. Tigecycline has a similar PK profile to omadacycline, and with its documented concentration levels achieved in human ELF, the inclusion of tigecycline was intended to provide assay sensitivity in the study.

Methods

The study was designed as a single-center, multiple-dose, open-label study to determine concentrations of omadacycline and tigecycline in pulmonary compartments (ELF and AC) in healthy adult subjects after administration of omadacycline and tigecycline to steady state levels of dosing. A total of 62 healthy volunteers participated in the study, who were randomized in a 2:1 ratio to receive either omadacycline or tigecycline. Of these, 42 received omadacycline as 5 intravenous doses of 100 mg administered as 30 minute infusions at t=0, 12, 24, 48 and 72 hours. The remaining 20 subjects received tigecycline as 1 intravenous dose of 100 mg administered as a 30 minute infusion at t=0, followed by 6 intravenous doses of 50 mg administered as 30 minute infusions at t=12, 24, 36, 48, 60, and 72 hours. A study completion visit was conducted on the day following the final test article dose. There was a final follow-up assessment 7 to 14 days following the subject's last dose of test article which may be completed by telephone contact or other interactive technology unless an examination was needed to evaluate adverse events or abnormalities noted at the study completion visit.

Plasma PK samples were collected pre-dose and at 0.5, 1, 1.5, 2, 3, 4, 6, 8, 12 and 24 hours post-dose on day 4. A sample for 24 hours was collected only for omadacycline. One BAL sample was collected from each subject on day 4. Subjects were randomized to one of the following collection times: 0.5, 1, 2, 4, 8, 12 or 24 hours post-dose. A sample for 24 hours was collected only for omadacycline.

A previously developed omadacycline population PK model was utilized to describe omadacycline plasma PK (Van Wart et al., ECCMID 2015. Abstr. 1739). In addition, linear three- and two-compartment models with ELF incorporated into the first peripheral compartment were used to model the PK data for omadacycline and tigecycline and to compute ratios of total-drug ELF to total-drug plasma AUC and total-drug ELF AUC to free-drug plasma AUC for both omadacycline and tigecycline.

Results

Parameters Calculated Using Previously Developed Omadacycline Population PK Model For subjects who received omadacycline, the mean (t SD) plasma PK parameters after the fifth omadacycline dose were as follows:

$C_{max}$: 2.26±0.76 µg/mL
volume of distribution: 165±58 L
clearance: 8.03±1.43 L/h; and
elimination half-life of 14.7±4.2 h.

Mean (±SD) concentrations of omadacycline (µg/mL) measured at the time of bronchoscopy and BAL in different compartments are shown in Table 10 below.

TABLE 10

Mean (± SD) concentrations of omadacycline (μg/mL) measured in plasma, epithelial lining fluid and alveolar cells (mostly alveolar macrophages).

| Sampling Time (hours) | Plasma (μg/mL) | Epithelial lining fluid (ELF) (μg/mL) | Alveolar Macrophages (AM) (μg/mL) |
|---|---|---|---|
| 0.5 | 1.80 ± 0.13 | 1.73 ± 1.01 | 14.26 ± 9.30 |
| 1 | 0.89 ± 0.19 | 2.25 ± 0.72 | 12.80 ± 8.48 |
| 2 | 0.93 ± 0.33 | 1.51 ± 0.94 | 10.77 ± 7.59 |
| 4 | 0.59 ± 0.15 | 0.95 ± 0.33 | 17.99 ± 7.17 |
| 8 | 0.56 ± 0.12 | 0.58 ± 0.19 | 12.27 ± 4.70 |
| 12 | 0.42 ± 0.07 | 0.61 ± 0.29 | 12.29 ± 4.61 |
| 24 | 0.27 ± 0.05 | 0.41 ± 0.13 | 10.36 ± 4.04 |

Figure 3:
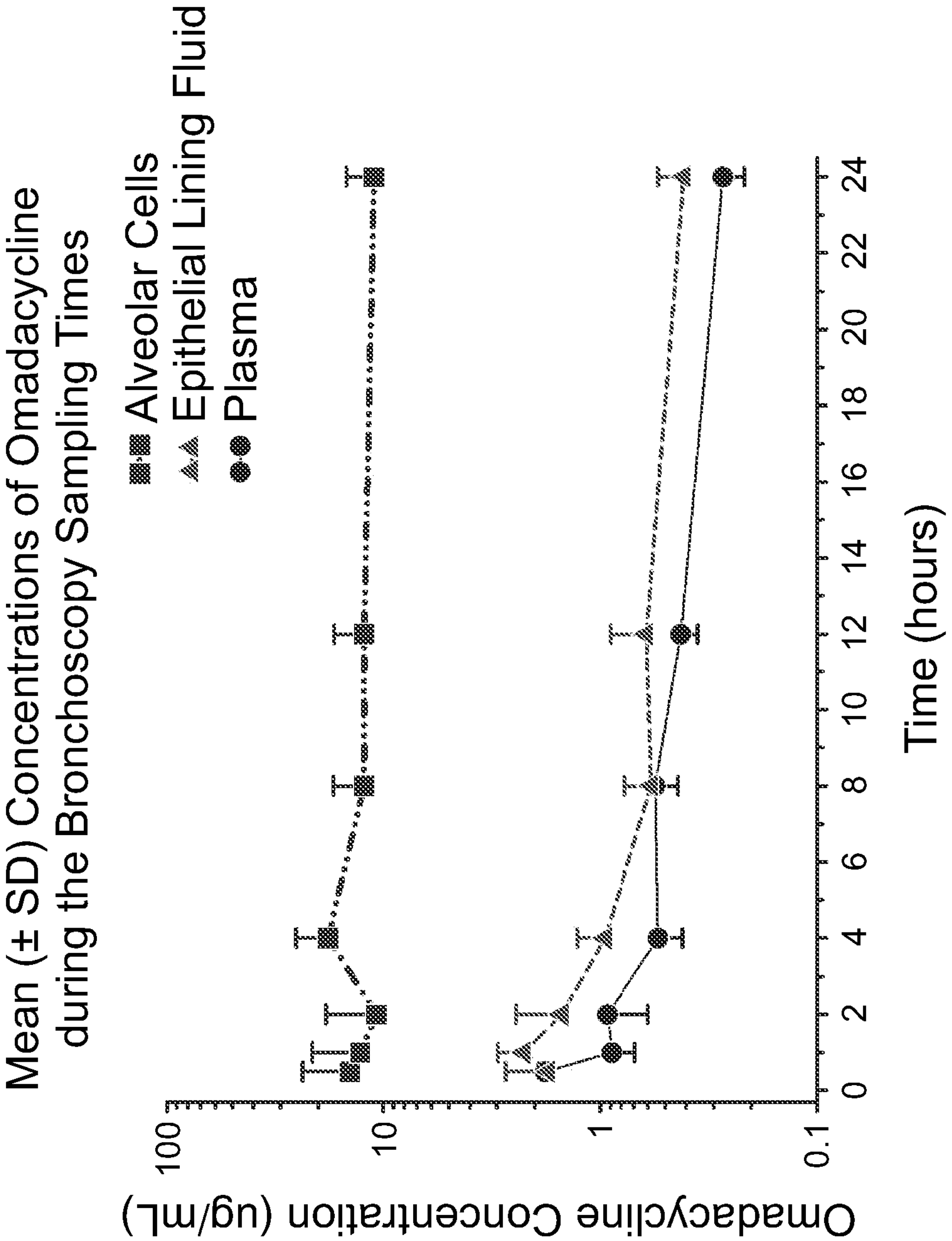
FIG. 3 is a graph showing mean concentration of omadacycline over time in plasma, epithelial lining fluid and alveolar cells after administration of omadacycline to healthy volunteers.

The data presented in Table 10 is also presented graphically in FIG. 3. Specifically, FIG. 3 shows omadacycline concentration over time in plasma, epithelial lining fluid and in alveolar cells. The data indicates that the mean omadacycline concentration in alveolar cells is at least an order of magnitude higher (about 25-fold higher) than that in plasma, while the mean omadacycline concentration in the epithelial lining fluid is at least about 40% higher than that in plasma. See ratios of omadacycline concentrations at different times presented in Table 11 below.

TABLE 11

Ratio of omadacycline concentration in Epithelial Lining Fluid and in alveolar cells to omadacycline concentration in plasma at different time points.

| Sampling Time (hours) | Ratio of Omadacycline Concentrations in Epithelial Lining Fluid to Plasma (Mean, SD) | Ratio of Omadacycline Concentrations in Alveolar Cells to Plasma (Mean, SD) |
|---|---|---|
| 0.5[a] | 0.95 ± 0.56 | 8.12 ± 5.95 |
| 1[a] | 2.72 ± 1.26 | 13.85 ± 7.38 |
| 2[b] | 1.50 ± 0.61 | 12.29 ± 6.57 |
| 4[a] | 1.79 ± 0.49 | 34.72 ± 15.14 |
| 8[a] | 1.07 ± 0.45 | 23.12 ± 11.17 |
| 12[a] | 1.44 ± 0.57 | 28.97 ± 8.78 |
| 24[a] | 1.65 ± 0.86 | 40.33 ± 10.29 |

[a]6 reported plasma, ELF, and AM concentrations at this sampling time
[b]5 samples plasma, ELF, and AM concentrations at this sampling time Penetration ratios based on $AUC_{0-2}$ values of mean and median omadacycline concentrations in the epithelial lining fluid and in plasma were 1.47 and 1.42, respectively, whereas the penetration ratios based on $AUC_{0-24}$ values of mean and median omadacycline concentrations in the alveolar cells and in plasma were 25.8 and 24.8, respectively. See Table 12 below, in which "$AUC_{mean}$" refers to area-under-the-curve based on mean concentration at each BAL sampling time and "$AUC_{median}$" refers to area-under-the-curve based on median concentration at each BAL sampling time.

TABLE 12

Penetration ratios based on $AUC_{mean}$ and $AUC_{median}$ of omadacycline in different compartments.

| | Plasma | Epithelial Lining Fluid (ELF) | Ratio ELF:Plasma | Alveolar Cells (AC) | Ratio AC:Plasma |
|---|---|---|---|---|---|
| $AUC_{mean}$ (μg*h/mL) | 11.73 | 17.23 | 1.47 | 302.5 | 25.8 |
| $AUC_{median}$ (μg*h/mL) | 11.80 | 16.74 | 1.42 | 292.3 | 24.8 |

-

Parameters Calculated Using Linear Three- and Two-Compartment Models with ELF Incorporated into the First Peripheral Compartment Model-computed total-drug ELF AUC to free-drug plasma AUC ratios are presented in Table 13 below.

TABLE 13

Free-drug plasma and total-drug ELF concentrations and penetration ratios for omadacycline and tigecycline.

| Drug | Exposure Matrix | Exposure Measure | Median | Interquartile Range |
|---|---|---|---|---|
| Omadacycline | Plasma | Free-drug $AUC_{72-96}$ (mg*h/L) | 9.61 | 8.07-11.3 |
| | ELF | Total-drug $AUC_{72-96}$ (mg*h/L) | 18.5 | 15.5-21.8 |
| | ELF | Penetration Ratio[a] | 1.93 | — |
| Tigecycline | Plasma | Free-drug $AUC_{72-96}$ (mg*h/L) | 1.38 | 1.14-1.59 |
| | ELF | Total-drug $AUC_{72-96}$ (mg*h/L) | 2.59 | 1.97-3.33 |
| | ELF | Penetration Ratio[b] | 1.87 | — |

[a]Represents the ratio of total-drug ELF $AUC_{72-96}$ to free-drug plasma $AUC_{72-96}$.
[b]Represents the ratio of total-drug ELF $AUC_{72-84}$ to free-drug plasma $AUC_{72-84}$.

Conclusions

The experimental data obtained in this study indicates that intravenous administration of omadacycline produces both extracellular and intracellular concentrations of omadacycline in the lungs that are higher than those in plasma. Specifically, extracellular concentration of omadacycline achieved in the lungs, i.e., in the epithelial lining fluid, is more than 1.4 times higher than the plasma concentration of omadacycline. Intracellular concentration of omadacycline achieved in the lungs, i.e., in the alveolar cells, such as macrophages, is, remarkably, about 25 times higher than the plasma concentration of omadacycline. Thus, the results demonstrate that omadacycline, when administered to the subject, concentrates in the alveolar cells of the lungs, such as macrophages. Because these cells are also often sites of mycobacterial infection, omadacycline is well suited for treating mycobacterial infections in the lungs.

Example 6. Comparison of In Vitro Susceptibility of Omadacycline with Tigecycline, Minocycline, Doxycycline and Other Comparator Antimicrobials Against Isolates of Nontuberculous Mycobacteria Introduction The aim of this study was to compare in vitro susceptibility of isolates of nontuberculous mycobacteria (NTM) recovered in the USA to treatment with omadacycline, and using tigecycline, minocycline, doxycycline and other antimicrobials as comparators.

Materials and Methods

A total of 65 NTM isolates were tested. Of the tested isolates, 50 were rapid-growing mycobacteria (RGM) isolates and 15 were slow-growing mycobacteria (SGM) isolates. Isolates were identified to species by gene sequencing (including erm gene sequencing) for determination of inducible macrolide susceptibility and tested for other antimicrobial susceptibility when received into the laboratory. Erythromycin resistance methylase (erm) gene confers inducible resistance to macrolides. For less commonly encountered species, isolates were supplemented by using stocks of well characterized U.S. isolates from diverse geographic sites collected within the last 5 years. The antimicrobials that were tested against RGM included amikacin, ciprofloxacin; clarithromycin, doxycycline, cefoxitin, imipenem, linezolid, minocycline, moxifloxacin, omadacycline, trimethoprim-sulfamethoxazole and tigecycline. The antimicrobials tested against RGM also included and tobramycin, which was tested only against *M. chelonae*. The antimicrobials tested against SGM included amikacin, ciprofloxacin, doxycycline, linezolid, minocycline, moxifloxacin, omadacycline, rifampin, rifabutin and trimethoprim-sulfamethoxazole.

MIC values were determined using two-fold serial dilutions of Mueller Hinton Broth following Clinical and Laboratory Standards Institute (CLSI) methodology (*Performance Standards for Susceptibility Testing of Mycobacteria, Norcadia* spp., and *Other Aerobic Actinomycetes*; M62, $1^{st}$ Edition).

Results

MIC values measured for RGM isolates are presented in Table 14 below.

TABLE 14

MIC values of different antimicrobials against RGM isolates.

| | SPECIES/ GROUP | SPEC. ID/ erm gene type | MIC μg/mL OMC | DOX | TGC | MIN | CIP |
|---|---|---|---|---|---|---|---|
| 1 | *M. abscessus* complex | MAB30 | 0.25 | >8 | 0.12 | >8 | 4 |
| 2 | *M. abscessus* complex | MAB30 | 0.25 | >8 | 0.12 | 8 | 4 |
| 3 | *M. abscessus* complex | MAB30 | 0.25 | >8 | 0.25 | >8 | >4 |
| 4 | *M. abscessus* complex | *massiliense* | 0.12 | >8 | 0.25 | 4 | >4 |
| 5 | *M. abscessus* complex | *massiliense*/ subsp. abs hybrid | 0.25 | >8 | 0.25 | >8 | >4 |
| 6 | *M. abscessus* complex | Type 1 *abscessus* | 0.12 | >8 | 0.12 | >8 | 4 |
| 7 | *M. abscessus* complex | Type 1 *abscessus* | 0.12 | >8 | 0.25 | 8 | 4 |
| 8 | *M. abscessus* complex | Type 1 *abscessus* | 0.12 | >8 | 0.12 | >8 | >4 |
| 9 | *M. abscessus* complex | Type 1 *abscessus* | 0.12 | >8 | 0.25 | >8 | 4 |
| 10 | *M. abscessus* complex | Type 1 *abscessus* | 0.12 | >8 | 0.12 | >8 | 4 |
| 11 | *M. abscessus* complex | Type 6 *abscessus* | 0.12 | >8 | 0.06 | 4 | >4 |
| 12 | *M. abscessus* complex | Type 6 *abscessus* | 0.12 | >8 | 0.12 | >8 | 4 |
| 13 | *M. abscessus* complex | Type 6 *abscessus* | 0.25 | >8 | 0.25 | >8 | >4 |
| 14 | *M. abscessus* complex | Type 6 *abscessus* | 0.12 | 8 | 0.12 | 4 | 4 |
| 15 | *M. abscessus* complex | Type 7 *abscessus* | 0.12 | >8 | 0.06 | 8 | 4 |
| 16 | *M. abscessus* complex | Type 7 *abscessus* | 0.25 | >8 | 0.12 | >8 | >4 |
| 17 | *M. abscessus* complex | Type 8 *abscessus* | 0.06 | >8 | 0.12 | 4 | 4 |

TABLE 14-continued

MIC values of different antimicrobials against RGM isolates.

| | | | | | | | |
|---|---|---|---|---|---|---|---|
| 18 | *M. chelonae* | *M. chelonae* | 0.12 | >8 | 0.12 | >8 | >4 |
| 19 | *M. chelonae* | *M. chelonae* | 0.25 | >8 | 0.25 | >8 | >4 |
| 20 | *M. chelonae* | *M. chelonae* | 0.12 | >8 | 0.12 | >8 | 2 |
| 21 | *M. chelonae* | *M. chelonae* | 0.12 | >8 | 0.5 | >8 | >4 |
| 22 | *M. chelonae* | *M. chelonae* | 0.25 | >8 | 0.25 | >8 | 2 |
| 23 | *M. fortuitum* group | *M. fortuitum* | 0.12 | ≤0.12 | 0.03 | ≤0.5 | ≤0.12 |
| 24 | *M. fortuitum* group | *M. fortuitum* | 0.12 | 0.25 | 0.12 | ≤0.5 | ≤0.12 |
| 25 | *M. fortuitum* group | *M. fortuitum* | 0.12 | >8 | ≤0.015 | >8 | ≤0.12 |
| 26 | *M. fortuitum* group | *M. porcinum* | 0.06 | 4 | ≤0.015 | 1 | 0.25 |
| 27 | *M. fortuitum* group | *M. porcinum* | 0.12 | 8 | 0.03 | 4 | 0.25 |
| 28 | *M. fortuitum* group | *M. porcinum/ M. boenickei* | 0.25 | 2 | 0.03 | 1 | 0.25 |
| 29 | *M. fortuitum* group | *M. porcinum/ M. boenickei* | 0.25 | >8 | 0.03 | 4 | 0.5 |
| 30 | *M. fortuitum* group | *M. porcinum/ M. boenickei* | 0.12 | >8 | 0.03 | 8 | 0.25 |
| 31 | *M. fortuitum* group | *M. senegalense* | 0.25 | ≤0.12 | 0.06 | ≤0.5 | 0.5 |
| 32 | *M. fortuitum* group | *M. senegalense* | 0.12 | ≤0.12 | 0.03 | ≤0.5 | 0.5 |
| 33 | *M. fortuitum* group | *M. senegalense* | 0.12 | ≤0.12 | 0.03 | ≤0.5 | 0.5 |
| 34 | *M. fortuitum* group | *M. senegalense* | 0.12 | ≤0.12 | 0.03 | ≤0.5 | 0.5 |
| 35 | *M. immunogenum* group | *M. immunogenum* | 0.5 | >8 | 0.5 | >8 | 1 |
| 36 | *M. immunogenum* group | *M. immunogenum* | 0.25 | 1 | 0.12 | ≤0.5 | 2 |
| 37 | *M. immunogenum* group | *M. immunogenum* | 0.5 | >8 | 0.5 | >8 | >4 |
| 38 | *M. immunogenum* group | *M. immunogenum* | 0.5 | >8 | 0.5 | >8 | >4 |
| 39 | *M. mucogenicum* group | *M. mucogenicum* | 0.25 | 0.25 | 0.12 | ≤0.5 | ≤0.12 |
| 40 | *M. mucogenicum* group | *M. mucogenicum* | 0.25 | ≤0.12 | 0.06 | ≤1 | 0.5 |
| 41 | *M. mucogenicum* group | *M. mucogenicum* | 1 | ≤0.12 | 0.06 | ≤0.5 | 0.25 |
| 42 | *M. mucogenicum* group | *M. mucogenicum* | 0.5 | ≤0.12 | 0.12 | ≤0.5 | 0.5 |
| 43 | *M. mucogenicum* group | *M. phocaicum* | 1 | ≤0.12 | 0.12 | ≤0.5 | 0.25 |
| 44 | *M. mucogenicum* group | *M. phocaicum* | 0.5 | >8 | 0.06 | >8 | 2 |
| 45 | *M. mucogenicum* group | *M. phocaicum* | 0.5 | >8 | 0.25 | >8 | 2 |
| 46 | *M. mucogenicum* group | *M. phocaicum* | 1 | >8 | 0.06 | 8 | 2 |
| 47 | *M. mucogenicum* group | *M. phocaicum* | 1 | 0.25 | 0.25 | ≤0.5 | 0.25 |
| 48 | *M. mucogenicum* group | *M. phocaicum* | 0.25 | 4 | 0.03 | 2 | 2 |
| 49 | *M. smegmatis* group | *M. goodii* | 0.06 | ≤0.12 | ≤0.015 | ≤0.5 | ≤0.12 |
| 50 | *M. smegmatis* group | *M. wolinskyi* | 0.5 | 1 | 0.03 | ≤0.5 | 1 |
| | | $MIC_{50}$ | 0.25 | >8 | 0.125 | 8 | 2 |
| | | $MIC_{90}$ | 0.5 | >8 | 0.25 | >8 | >4 |

| | MIC µg/mL | | | | | | | | |
|---|---|---|---|---|---|---|---|---|---|
| | MXF | AMK | IPM | FOX | LZD | SXT | CLA Initial [1] | CLA Extended[2] | TOB |
| 1 | 8 | 8 | 8 | 32 | 16 | 4/76 | ≤0.06 | 1 | — |
| 2 | 8 | 4 | 16 | 32 | 16 | 4/76 | ≤0.06 | 2 | — |
| 3 | 16 | 16 | 8 | 32 | 32 | >4/76 | 0.5 | 2 | — |
| 4 | 16 | 8 | 8 | 32 | 16 | >4/76 | 0.12 | 2 | — |
| 5 | 4 | 32 | 16 | 32 | 4 | 4/76 | ≤0.06 | ≤0.06 | — |
| 6 | 16 | 8 | 8 | 32 | 32 | 4/76 | 0.25 | N/A | — |
| 7 | 8 | 8 | 8 | 32 | 16 | >4/76 | 0.12 | >32 (10 d) | — |
| 8 | 16 | 8 | 8 | 32 | 16 | >4/76 | 0.12 | >32 (11 d) | — |
| 9 | 8 | >64 | 16 | 32 | 32 | 4/76 | 2 | >32 (10 d) | — |

TABLE 14-continued

MIC values of different antimicrobials against RGM isolates.

| | | | | | | | | | |
|---|---|---|---|---|---|---|---|---|---|
| 10 | 4 | 16 | 16 | 32 | 16 | 4/76 | 0.25 | 32 (11 d) | — |
| 11 | 8 | 16 | 8 | 32 | 8 | >4/76 | 0.12 | >32 (10 d) | — |
| 12 | 4 | 8 | 16 | 32 | 8 | 4/76 | 0.25 | >32 (7 d) | — |
| 13 | 8 | 4 | 8 | 32 | 16 | >4/76 | 0.25 | >32 (11 d) | — |
| 14 | 8 | 16 | 8 | 64 | ≤2 | 4/76 | ≤0.06 | >32 (14 d) | — |
| 15 | 8 | 8 | 8 | 32 | 16 | 4/76 | 0.5 | >32 (10 d) | — |
| 16 | 4 | 16 | 8 | 32 | ≤2 | 4/76 | ≤0.06 | >32 (10 d) | — |
| 17 | 4 | 4 | 8 | 32 | 16 | ≥4/76 | 0.25 | >32 (10 d) | — |
| 18 | 4 | 8 | 16 | >64 | 16 | 4/76 | 0.25 | 2 | ≤2 |
| 19 | 8 | 16 | 16 | >64 | 8 | >4/76 | 0.25 | 0.5 | ≤2 |
| 20 | 2 | 16 | 16 | >64 | 4 | 2/38 | 0.5 | 0.5 | ≤2 |
| 21 | >16 | 16 | 32 | >64 | 16 | 4/76 | 0.5 | 2 | ≤2 |
| 22 | 2 | 16 | 16 | >64 | 16 | >4/76 | 1 | 2 | ≤2 |
| 23 | ≤0.06 | ≤2 | ≤2 | 32 | ≤2 | ≤1/19 | 1 | >32 (7 d) | — |
| 24 | ≤0.06 | ≤2 | 4 | >64 | 4 | ≤1/19 | 0.5 | >32 (10 d) | — |
| 25 | ≤0.06 | ≤2 | ≤2 | 32 | 4 | ≤1/19 | 2 | >32 (7 d) | — |
| 26 | ≤0.06 | ≤2 | ≤2 | 32 | ≤2 | ≤1/19 | 0.5 | >32 | — |
| 27 | 0.12 | ≤2 | 4 | 32 | 4 | 2/38 | 2 | >32 (10 d) | — |
| 28 | 0.25 | ≤2 | 8 | 32 | ≤2 | 1/19 | 8 | >32 (10 d) | — |
| 29 | 0.12 | ≤2 | 4 | 32 | 4 | 2/38 | 4 | >32 (7 d) | — |
| 30 | ≤0.06 | ≤2 | ≤2 | ≤16 | ≤2 | 1/19 | 1 | >32 | — |
| 31 | 0.12 | ≤2 | ≤2 | 32 | ≤2 | 2/38 | 0.12 | 0.5 | — |
| 32 | 0.12 | ≤2 | ≤2 | 32 | ≤2 | 1/19 | 0.12 | 0.5 | — |
| 33 | 0.12 | ≤2 | ≤2 | <16 | ≤2 | 2/38 | 0.12 | 1 | — |
| 34 | 0.12 | ≤2 | ≤2 | 32 | ≤2 | 2/38 | ≤0.06 | 1 | — |
| 35 | 8 | 16 | 16 | >64 | 32 | 4/76 | 0.25 | 1 | — |
| 36 | 4 | 4 | 32 | >64 | 8 | 4/76 | 0.12 | 2 | 8 |
| 37 | 16 | 8 | 16 | >64 | 32 | >4/76 | 1 | 2 | >8 |
| 38 | 16 | 8 | 32 | >64 | 32 | >4/76 | 0.5 | 2 | >8 |
| 39 | 0.12 | ≤2 | ≤2 | ≤16 | ≤2 | ≤1/19 | ≤0.06 | 0.12 | — |
| 40 | 0.25 | ≤2 | ≤2 | ≤16 | ≤2 | ≤1/19 | 0.25 | 1 | — |
| 41 | 0.25 | ≤2 | ≤2 | ≤16 | ≤2 | ≤1/19 | 0.5 | 1 | — |
| 42 | 0.5 | ≤2 | ≤2 | ≤16 | ≤2 | ≤1/19 | ≤0.06 | 0.12 | — |
| 43 | 0.25 | ≤2 | ≤2 | ≤16 | ≤2 | ≤1/19 | 0.25 | 1 | — |
| 44 | 0.5 | ≤2 | ≤2 | ≤16 | ≤2 | ≤1/19 | 0.25 | 1 | — |
| 45 | 1 | ≤2 | ≤2 | ≤16 | ≤2 | ≤1/19 | 0.25 | 1 | — |
| 46 | 1 | ≤2 | ≤2 | ≤16 | ≤2 | ≤1/19 | ≤0.06 | 0.12 | — |
| 47 | 0.5 | ≤2 | ≤2 | ≤16 | 4 | ≤1/19 | 0.25 | 0.5 | — |
| 48 | 1 | ≤2 | ≤2 | ≤16 | ≤2 | ≤1/19 | 0.12 | 0.5 | — |
| 49 | ≤0.06 | ≤2 | 4 | >64 | ≤2 | ≤1/19 | 16 | >32 (6 d) | — |
| 50 | 0.25 | ≤2 | 4 | 64 | 4 | 2/38 | >32 | N/A | — |
| | 2 | 4 | 8 | 32 | 4 | 2/28 | 0.25 | 2 | N/A |
| | 16 | 16 | 16 | >64 | 32 | >4/76 | 2 | >32 | N/A |

[1] Initial reading for clarithromycin is generally 3-4 days

[2]Extended reading for clarithromycin is up to/including 14 days unless resitant before 14 days AMK = amikacin; CIP = ciprofloxacin; CLA = clarithromycin; DOX = doxycycline; FOX = cefoxitin; IPM = imipenem; LZD = linezolid; MIN = minocycline; MXF = moxifloxacin; N/A = not applicable (not enough data points for calculation); OMC = omadacycline; SXT = trimethoprim-sulfamethoxazole; TGC = tigecycline; TOB = tobramcyin MIC values measured for slow-growing NTM isolates are presented in Table 15 below.

TABLE 15

MIC values of different antimicrobials against slow-growing NTM isolates.

| SPECIES/ | | MIC μg/mL | | | | | | | | | |
|---|---|---|---|---|---|---|---|---|---|---|---|
| GROUP | Species | OMC | DOX | MIN | CIP | MXF | AMK | RIF | RFB | LZD | SXT |
| 1 MAC | *M. avium* | >16 | — | — | — | 2 | 32 | — | — | 32 | — |
| 2 MAC | *M. avium* | >16 | — | — | — | 0.25 | 16 | — | — | 32 | — |
| 3 MAC | *M. avium* | >16 | — | — | — | 4 | 8 | — | — | >32 | — |
| 4 MAC | *M. chimaera* | >16 | — | — | — | 4 | 8 | — | — | 16 | — |
| 5 MAC | *M. chimaera* | >16 | — | — | — | 2 | 8 | — | — | 32 | — |
| 6 MAC | *M. intracellulare* | >16 | — | — | — | 2 | 8 | — | — | 32 | — |
| 7 MAC | *M. intracellulare* | >16 | — | — | — | 1 | 8 | — | — | 16 | — |
| 8 MAC | *M. intracellulare* | >16 | — | — | — | 2 | 16 | — | — | 32 | — |
| 9 MAC | *M. intracellulare* | >16 | — | — | — | 2 | 16 | — | — | 32 | — |
| 10 MAC | *M. intracellulare* | >16 | — | — | — | 0.5 | 16 | — | — | >32 | — |
| 11 Other | *M. arupense* | >16 | 16 | 8 | >4 | >16 | 8 | >2 | ≤0.25 | 32 | 4/76 |
| 13 Other | *M. simiae* | >16 | >16 | 4 | >4 | 4 | 32 | >2 | ≤0.25 | >32 | 4/76 |
| 14 Other | *M. simiae* | >16 | >16 | >8 | 2 | 2 | 16 | >2 | >2 | 32 | 4/76 |

TABLE 15-continued

MIC values of different antimicrobials against slow-growing NTM isolates.

| SPECIES/ GROUP | Species | MIC µg/mL OMC | DOX | MIN | CIP | MXF | AMK | RIF | RFB | LZD | SXT |
|---|---|---|---|---|---|---|---|---|---|---|---|
| 15 Other | *M. simiae* | >16 | >16 | >8 | >4 | 8 | 16 | >2 | >2 | >32 | 4/76 |
| | $MIC_{50}$ | >16 | N/A | N/A | N/A | 2 | 16 | N/A | N/A | 32 | N/A |
| | $MIC_{90}$ | >16 | N/A | N/A | N/A | 8 | 32 | N/A | N/A | >32 | N/A |

AMK = amikacin; CIP = ciprofloxacin; DOX = doxycycline; LZD = linezolid; MAC = Mycobacterium avium complex; MIN = minocycline; MXF = moxifloxacin; N/A = not applicable (not enough data points for calculation) OMC = omadacycline; RIF = rifampin; RFB = rifabutin; SXT = trimethoprim-sulfamethoxazole Conclusions Omadacycline demonstrated activity against a variety of RGM species, including *M. abscessus* complex, *M. chelonae, M. fortuitum* group, *M. immunogenum* group, *M. mucogenium* group, and *M. smegmatis* group clinical isolates with an $MIC_{50}$ value of 0.25 and an $MIC_{90}$ value of 0.5 µg/mL. Omadacycline was less active against the small number of SGM isolates tested with MIC values above the highest concentration evaluated.

EQUIVALENTS

Those skilled in the art will recognize, or be able to ascertain using no more than routine experimentation, many equivalents to the specific embodiments and methods described herein. Such equivalents are intended to be encompassed by the scope of the present invention. All patents, patent applications, and literature references cited herein are hereby expressly incorporated by reference.

What is claimed is:

1. A method of treating or preventing a mycobacterial infection in a subject in need thereof, said method comprising administering to said subject an effective amount of a tetracycline compound, or a pharmaceutically acceptable salt or ester thereof, wherein said tetracycline compound is omadacycline represented by formula (5):

(5)

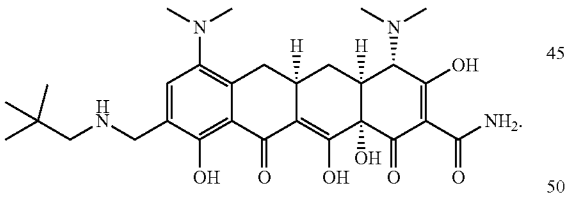

such that said mycobacterial infection in said subject is treated or prevented.

2. The method of claim 1, wherein the mycobacterial infection is caused by a slow-growing *mycobacterium.*

3. The method of claim 2, wherein the slow-growing *mycobacterium* belongs to Terrae clade, Triviale clade, Tuberculosis-Simiae clade, or a *Mycobacterium tuberculosis* complex (MTBC).

4. The method of claim 3, wherein the slow-growing *mycobacterium* belongs to a mycobacterial species selected from the group consisting of the following species: *M. terrae, M. algericus, M. arupensis, M. engbaekii, M. heraklionensis, M. hiberniae, M. icosiumassiliensis, M. kumamotonensis, M. longobardus, M. minnesotensis, M. nonchromogenicus, M. paraterrae, M. senuense, M. sinensis M. virginiensis, M. trivialis, M. koreensis* and *M. parakoreensis, M. tuberculosis, M. tuberculosis* subsp. tuberculosis, *M. africanum, M. alsense, M. angelicum, M. arosiense, M. asiaticum, M. avium, M. avium* subsp. *avium, M. avium* subsp. paratuberculosis, *M. avium* subsp. *silvaticum, M. avium* subsp. hominissuis, *M. bohemicum, M. botniense, M. bouchedurhonense, M. bourgelatii, M. bovis, M. bovis* subsp. *bovis, M. bovis* subsp. *caprae, M. branderi, M. canettii, M. caprae, M. celatum, M. chimaera, M. colombiense, M. conspicuum, M. cookii, M. europaeum, M. florentinum, M. fragae, M. gastri, M. genavsnse, M. gordonae, M. haemophiluseckshornense, M. heidelbergense, M. indicus pranii, M. interjectum, M. intermedium, M. intracellulare, M. kansasii, M. kubicae, M. kyorinense, M. lacus, M. lentiflavum, M. leprae, M. lepraemurium, M. lepromatosis, M. liflandii, M. malmoense, M. mantenii, M. marinum, M. marseillense, M. microti, M. monteriorense, M. mungi, M. nebraskense, M. novomagense, M. orygis, M. palustre, M. paraense, M. parraffinicum, M. paragordonae, M. paraintracellulare, M. parascrofulaceum, M. paraseculense, M. parmense, M. perscum, M. pinnipedii, M. pseudoshotsii, M. riyadhense, M. saskatchewanense, M. scrofulaceum, M. seculense, M. sherrisii, M. shimoidei, M. shinjukuense, M. shottsii, M. simiae, M. stomatepiae, M. szulgai, M. timonense, M. triplex, M. ulcerans, M. xenopi* and *M. yongonense, M. africanum, M. bovis, M. bovis* BCG, *M. canetti, M. caprae, M. microti, M. mungi, M. orygis, M. pinnipedii, M. suricattae* and *M. tuberculosis.*

5. The method of claim 4, wherein the slow-growing *mycobacterium* belongs to a mycobacterial species *M. tuberculosis.*

6. The method of claim 2, wherein the slow-growing *mycobacterium* is a nontuberculous *mycobacterium* (NTM).

7. The method of claim 6, wherein the NTM belongs to a *Mycobacterium avium* complex (MAC).

8. The method of claim 7, wherein the NTM belongs to a mycobacterial species selected from the group consisting of the following species: *M. avium, M. avium* paratuberculosis, *M. avium* silvaticum, *M. avium* "hominissuis", *M. colombiense, M. chimaera, M. indicus* pranii and *M. intracellulare.*

9. The method of claim 1, wherein the mycobacterial infection is caused by a rapid-growing *mycobacterium.*

10. The method of claim 9, wherein the rapid-growing *mycobacterium* is NTM.

11. The method of claim 9, wherein the rapid-growing *mycobacterium* belongs to an Abscessus-Chelonae clade.

12. The method of claim 11, wherein the rapid-growing *mycobacterium* belongs to a mycobacterial species selected from the group consisting of the following species: *M. abscessus, M. abscessus* subsp. *abscessus, M. abscessus* subsp. bolletii, *M. abscessus* subsp. massiliense, *M. chelonae, M. chelonae* subsp. chelonae, *M. immunogenum, M. salmoniphilum, M. franklinii* and *M. saopaulense.*

13. The method of claim 12, wherein the rapid-growing *mycobacterium* belongs to a mycobacterial species *M. abscessus.*

14. The method of claim 12, wherein the rapid-growing *mycobacterium* belongs to a mycobacterial species *M. chelonae.*

15. The method of claim 9, wherein the rapid-growing *mycobacterium* belongs to a Fortuitum-Vaccae clade.

16. The method of claim 15, wherein the rapid-growing *mycobacterium* belongs to a mycobacterial species selected from the group consisting of the following species: *M. fortuitum, M. fortuitum* subsp. fortuitum, *M. fortuitum* subsp. acetamidolyticum, *M. acapulcense, M. agri, M. aichiense, M. alvei, M. anyangense, M. arabiense, M. arcueilence, M. aromaticivorans, M. aubagnense, M. aurum, M. austroafrinacum, M. bacteremicum, M. boenickei, M. brisnanense, M. brumae, M. canariasense, M. celeriflavum, M. chitae, M. chlorophenolicum, M. chubuense, M. conceprionense, M. confluentis, M. cosmeticum, M. crocinum, M. diernhoferi, M. doricum, M. duvalii, M. elephantis, M. fallax, M. facinogenes, M. flavescens, M. fluoranthenivorans, M. frederikspergense, M. gadium, M. gilvum, M. goodii, M. hassiacum, M. helvum, M. hippocampi, M. hodieri, M. holsaticum, M. houstonense, M. insubricum, M. iranicum, M. komanii, M. komossense, M. litorale, M. llatzerense, M. lutetiense, M. madagascariense, M. mageritense, M. malmesburyense, M. monacense, M. montmartrense, M. moriokaense, M. mucogenicum, M. murale, M. neoaurum, M. neworleansense, M. novocastrense, M. obuense, M. oryzae, M. pallens, M. parafortuitum, M. peregrinum, M. phlei, M. phocaicum, M. porcinum, M. ponferae, M. psychrotolerans, M. pulvens, M. pyrenivorans, M. rhodesiae, M. rufum, M. rutilum, M. sarraceniae, M. sediminis, M. senegalense, M. septicum, M. setense, M. smegmatis, M. sphagni, M. thermoresistibile, M. tokaiense, M. tusciae, M. vaccae, M. vanbaalenii, M. vulneris* and *M. wolinskyi.*

17. The method of claim 16, wherein the rapid-growing *mycobacterium* belongs to a mycobacterial species *M. fortuitum.*

18. The method of claim 1, wherein the mycobacterial infection is in the lungs of the subject.

19. The method of claim 18, wherein the subject additionally has a disease of the lungs or has undergone lung transplantation.

20. The method of claim 1, wherein the mycobacterial infection is:

in a lymph node of the subject; or an osteoarticular infection; or a skin or a soft tissue infection (SSTI); or involves a foreign object disposed in the subject.

21. The method of claim 20, wherein the foreign object is selected from the group consisting of a medical device, an implant and a tattoo ink.

22. A method of treating or preventing a mycobacterial disease in a subject in need thereof, said method comprising administering to said subject an effective amount of a tetracycline compound, or a pharmaceutically acceptable salt or ester thereof, wherein said tetracycline compound is omadacycline represented by formula (5):

(5)

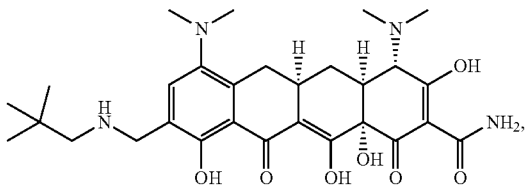

such that said mycobacterial disease in said subject is treated or prevented.

23. A method of controlling or reducing the advancement, severity or effects of a mycobacterial disease in a subject in need thereof, said method comprising administering to said subject an effective amount of a tetracycline compound, or a pharmaceutically acceptable salt or ester thereof, wherein said tetracycline compound is omadacycline represented by formula (5):

(5)

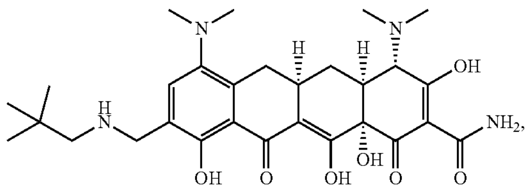

such that said mycobacterial disease in said subject is controlled, or the advancement, severity or effects of said mycobacterial disease in said subject are reduced.

24. The method of claim 22, wherein said mycobacterial disease is caused by an infection with a slow-growing *mycobacterium.*

25. The method of claim 24, wherein the slow-growing *mycobacterium* belongs to a *Mycobacterium tuberculosis* complex (MTBC).

26. The method of claim 24, wherein the slow-growing *mycobacterium* belongs to a mycobacterial species *M. tuberculosis.*

27. The method of claim 26, wherein said mycobacterial disease is tuberculosis.

28. The method of claim 22, wherein said mycobacterial disease is caused by an infection with a rapid-growing *mycobacterium.*

29. The method of claim 22, wherein said mycobacterial disease is caused by an infection with NTM.

30. The method of claim 29, wherein said NTM belongs to a mycobacterial species selected from the group consisting of the following species: *M. avium, M. kansasii, M. scrofulaceum, M. xenopi, M. simiae, M. habana, M. szulgai, M. fortuitum, M. vaccae, M. malmoense, M. heckeshornense, M. chelonae* and *M. abscessus.*

31. The method of claim 30, wherein said NTM belongs to a mycobacterial species selected from the group consisting of the following species: *M. abscessus, M. chelonae* and *M. fortuitum.*

32. The method of claim 22, wherein said mycobacterial disease is selected from the group consisting of tuberculosis, leprosy, a pulmonary disease, lymphadenitis, a skin disease, an eye disease, a soft tissue disease, a bone disease, a fish tank granuloma and a Buruli ulcer.

33. The method of claim 32, wherein said pulmonary disease is selected from the group consisting of bronchiectasis and pulmonary infection.

34. The method of claim 22, wherein said mycobacterial disease is associated with a mycobacterial infection in a lymph node, a joint, a bone, a skin, a soft tissue of the subject.

35. The method of claim 22, wherein said mycobacterial disease is associated with a mycobacterial infection involving a foreign object disposed in the subject.

36. A method of treating or preventing a mycobacterial infection in a subject in need thereof, said method comprising administering to said subject an effective amount of a tetracycline compound, or a pharmaceutically acceptable salt or ester thereof, wherein said tetracycline compound is omadacycline represented by formula (5):

(5)

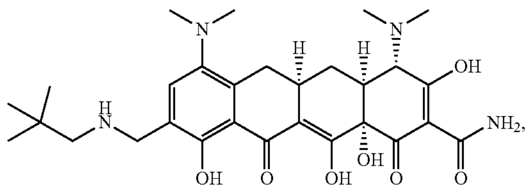

wherein said mycobacterial infection is caused by a nontuberculous *mycobacterium* (NTM).

37. The method of claim 36, wherein the NTM is a slow-growing *mycobacterium*.

38. The method of claim 37, wherein the NTM belongs to a *Mycobacterium avium* complex (MAC).

39. The method of claim 36, wherein the NTM is a rapid-growing *mycobacterium*.

40. The method of claim 39, wherein the NTM belongs to a mycobacterial species selected from the group consisting of the following species: *M. abscessus, M. chelonae* and *M. fortuitum*.

41. The method of claim 1, wherein said tetracycline compound is administered as a monotherapy.

42. The method of claim 1, wherein said tetracycline compound is administered in combination with at least one additional anti-mycobacterial agent.

43. The method of claim 42, wherein said at least one additional anti-mycobacterial agent is selected from the group consisting of diarylquinolone, rifapentine, rifalazil, a nitroimidazole, a benzothiazinone, capreomycin, clofazimine, cycloserine, dapsone, a thiocarbamide, ethambutol, DC-159a, a nitrobenzthiazole, sutezolid (PNU-100480), AZD-5847, posizolid (AZD-2563), para-aminosalicylic acid, SQ-109, SQ-609, a capuramycin, a caprazene nucleoside, an isothiazoloquinolone, thioridazine, thiacetazone, dirithromycin, roxithromycin, telithromycin, azithromycin, clarithromycin, erythromycin, amikacin, kanamycin, streptomycin, levofloxacin, moxifloxacin, gatifloxacin, linezolid, rifalazil, imipenem, meropenem, clavulanate and isoniazid.

* * * * *